(12) United States Patent
Streeter et al.

(10) Patent No.: US 11,137,778 B2
(45) Date of Patent: *Oct. 5, 2021

(54) DYNAMIC SUPPORT APPARATUS AND SYSTEM

(71) Applicant: DEKA Products Limited Partnership, Manchester, NH (US)

(72) Inventors: Alexander D. Streeter, Concord, NH (US); David E. Altobelli, Hollis, NH (US); N. Christopher Perry, Manchester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/579,186

(22) Filed: Sep. 23, 2019

(65) Prior Publication Data

US 2020/0019193 A1 Jan. 16, 2020

Related U.S. Application Data

(60) Division of application No. 14/499,823, filed on Sep. 29, 2014, now Pat. No. 10,423,171, which is a (Continued)

(51) Int. Cl.
*A61F 2/78* (2006.01)
*A61F 2/68* (2006.01)
(Continued)

(52) U.S. Cl.
CPC ......... *G05D 7/0623* (2013.01); *A61F 2/7843* (2013.01); *A61F 5/012* (2013.01); *A61F 5/024* (2013.01); *A61F 5/34* (2013.01); *F16L 39/00* (2013.01); *G05B 15/02* (2013.01); *A61F 2002/5083* (2013.01);
(Continued)

(58) Field of Classification Search
CPC .......... A61F 2/68; A61F 2/78; A61F 2002/74; A61F 2/7843; A61F 5/34; A61F 5/012
See application file for complete search history.

(56) References Cited

U.S. PATENT DOCUMENTS 6,685,661 B2 * 2/2004 Peled ................. A43B 7/00
601/149
8,177,734 B2 * 5/2012 Vess ................ A61H 23/04
601/149

(Continued)

*Primary Examiner* — Bruce E Snow
(74) *Attorney, Agent, or Firm* — Reid Knott Cunningham

(57) ABSTRACT

A control unit system. The system includes a control unit which includes a control unit charging interface, at least one magnet located proximate to the control unit charging interface, at least one actuator, a detachable manifold including at least one magnet, fluidly coupled to the at least one actuator, a pump connected to the at least one actuator for causing actuation thereof, and a control system for controlling the pump, wherein the control system controls the pump to actuate the at least one actuator at least in response to a signal received by the control system. The system also includes a recharging device configured to receive the control unit, the recharging device including a reed switch, wherein when the magnet in the control unit is located proximate to the reed switch, the switch is activated.

10 Claims, 66 Drawing Sheets

Related U.S. Application Data continuation of application No. 13/461,336, filed on May 1, 2012, now Pat. No. 8,845,754, which is a continuation-in-part of application No. 13/088,035, filed on Apr. 15, 2011, now Pat. No. 8,956,421, which is a continuation-in-part of application No. 12/706,340, filed on Feb. 16, 2010, now Pat. No. 8,074,559, which is a continuation-in-part of application No. 12/026,971, filed on Feb. 6, 2008, now Pat. No. 8,870,970.

(60) Provisional application No. 61/168,793, filed on Apr. 13, 2009, provisional application No. 60/899,835, filed on Feb. 6, 2007, provisional application No. 61/376,924, filed on Aug. 25, 2010, provisional application No. 61/504,034, filed on Jul. 1, 2011.

(51) Int. Cl.
| | | |
|---|---|---|
| *G05D 7/06* | (2006.01) | |
| *A61F 5/02* | (2006.01) | |
| *A61F 5/34* | (2006.01) | |
| *F16L 39/00* | (2006.01) | |
| *A61F 5/01* | (2006.01) | |
| *G05B 15/02* | (2006.01) | |
| *A61F 2/50* | (2006.01) | |
| *A61F 2/70* | (2006.01) | |
| *A61F 2/74* | (2006.01) | |
| *A61F 2/76* | (2006.01) | |
| *A61F 7/00* | (2006.01) | |

(52) U.S. Cl.
CPC ... *A61F 2002/704* (2013.01); *A61F 2002/741* (2013.01); *A61F 2002/745* (2013.01); *A61F 2002/7635* (2013.01); *A61F 2002/7655* (2013.01); *A61F 2007/006* (2013.01); *A61F 2007/0063* (2013.01)

(56) References Cited

U.S. PATENT DOCUMENTS

| | | | |
|---|---|---|---|
| 8,956,421 B2* | 2/2015 | Streeter | A61F 2/54 623/26 |
| 10,423,171 B2* | 9/2019 | Streeter | A61F 5/34 |
| 2003/0181990 A1* | 9/2003 | Phillips | A61F 2/7843 623/37 |
| 2015/0359644 A1* | 12/2015 | Sanders | A61F 2/80 623/34 |
| 2020/0060926 A1* | 2/2020 | Douglas | A61H 9/0078 |

* cited by examiner

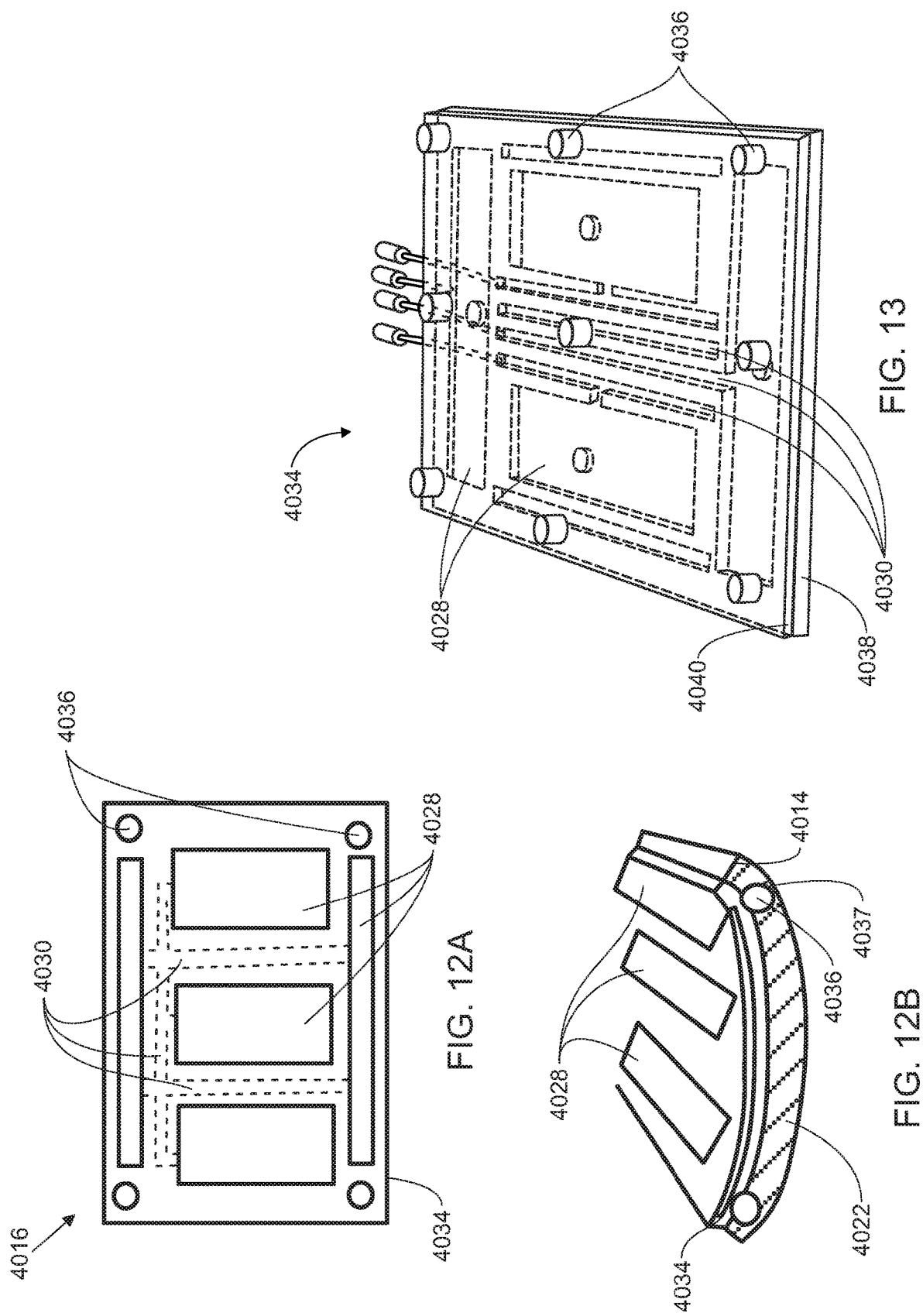

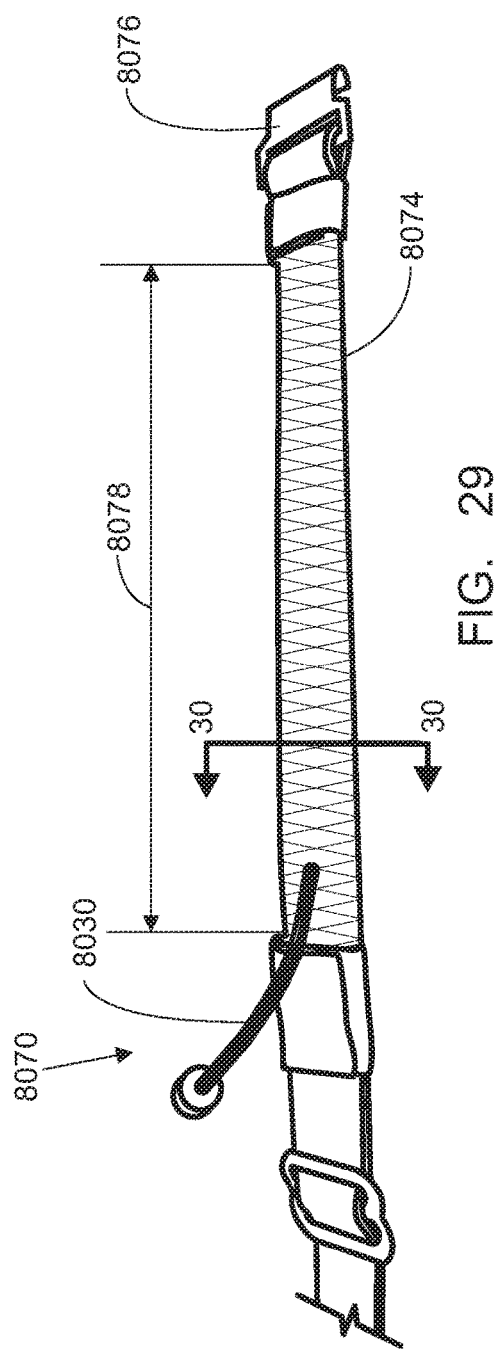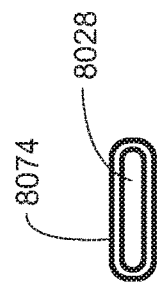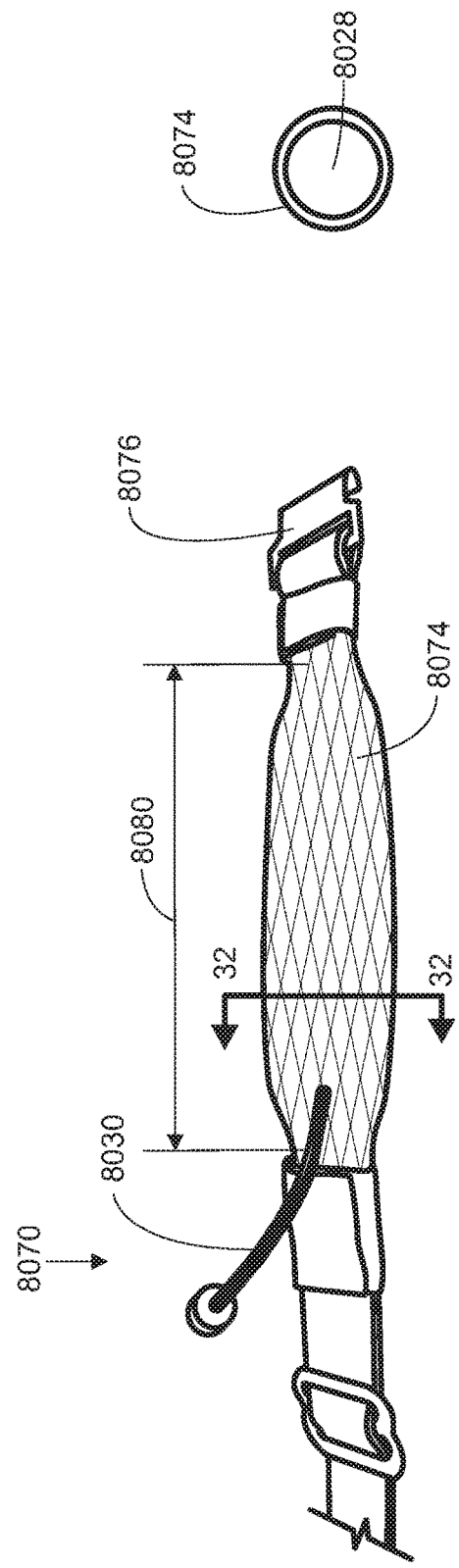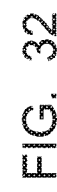

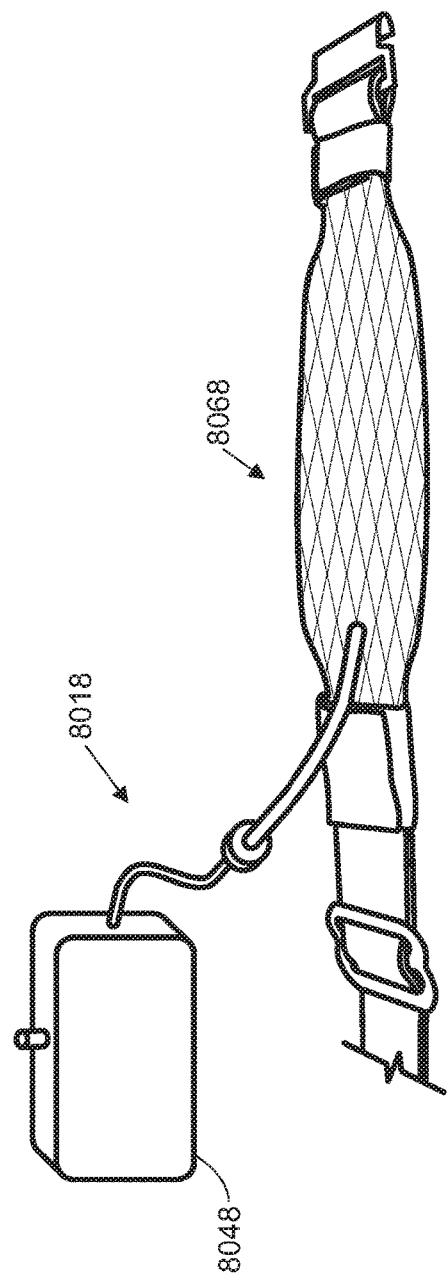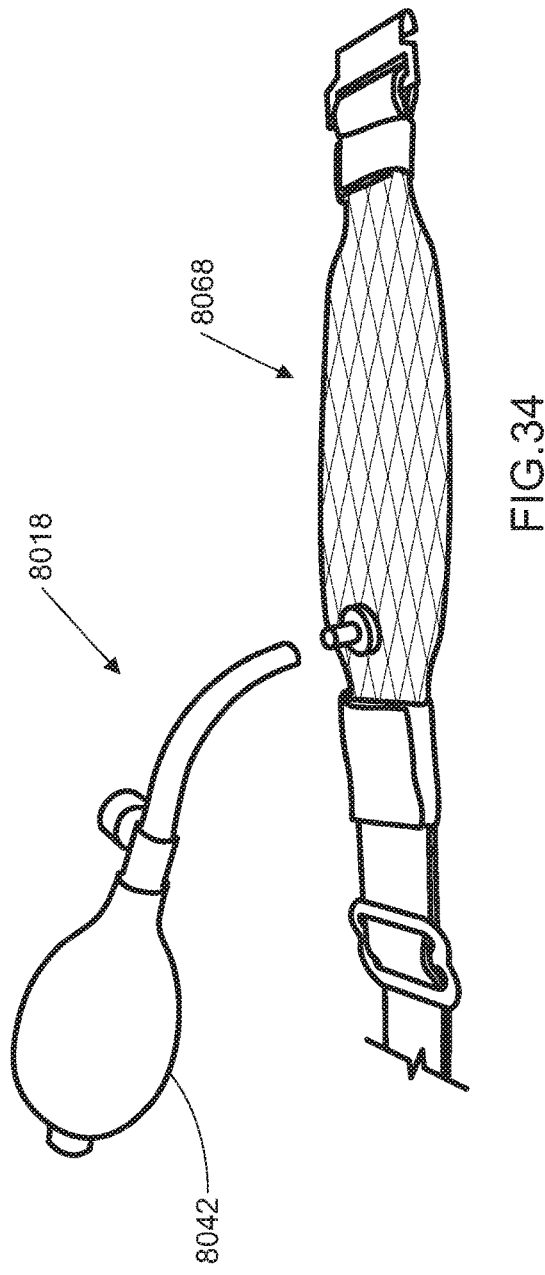

DYNAMIC SUPPORT APPARATUS AND SYSTEM

CROSS-REFERENCE TO RELATED APPLICATIONS

This application is a divisional of U.S. patent application Ser. No. 14/499,823, filed Sep. 29, 2014 and entitled Dynamic Support Apparatus and System, now U.S. Pat. No. 10,423,171, issued Sep. 24, 2019, which is a continuation of U.S. patent application Ser. No. 13/461,336, filed May 1, 2012 and entitled Dynamic Support Apparatus and System, now U.S. Pat. No. 8,845,754, issued Sep. 30, 2014, which is a continuation-in-part of U.S. patent application Ser. No. 13/088,035, filed Apr. 15, 2011 and entitled Dynamic Support Apparatus and System, now U.S. Pat. No. 8,956,421, issued Feb. 17, 2015, which is a continuation-in-part of U.S. patent application Ser. No. 12/706,340, filed Feb. 16, 2010 and entitled Dynamic Support Apparatus and System, now U.S. Pat. No. 8,074,559, issued Dec. 13, 2011, which claims priority to U.S. Provisional Patent Application Ser. No. 61/168,793, filed Apr. 13, 2009 and entitled Dynamic Support Apparatus, all of which are hereby incorporated herein by reference in their entireties.

U.S. patent application Ser. No. 12/706,340 is also a continuation-in-part of U.S. patent application Ser. No. 12/026,971, filed Feb. 6, 2008 and entitled Dynamic Support Apparatus, which is now U.S. Pat. No. 8,870,970 issued Oct. 28, 2014, which claims priority from U.S. Provisional Patent Application Ser. No. 60/899,835, filed Feb. 6, 2007 and entitled Dynamic Support Apparatus, both of which are hereby incorporated herein by reference in their entireties.

U.S. patent application Ser. No. 13/088,035 also claims priority to U.S. Provisional Patent Application Ser. No. 61/376,924, filed Aug. 25, 2010 and entitled Dynamic Support Apparatus and System, which is also hereby incorporated by reference in its entirety.

U.S. patent application Ser. No. 13/461,336 also claims the benefit of U.S. Provisional Application No. 61/504,034, filed Jul. 1, 2011 and entitled Dynamic Support Apparatus and System, which is hereby incorporated herein by reference in its entirety.

STATEMENT OF GOVERNMENT INTEREST

This invention was made with Government support under Contract Number W911NF-09-C-0035 awarded by the U.S. Army RDECOM ACQ CTR. The Government has certain rights in the invention.

TECHNICAL FIELD

The present invention relates to support apparatuses and more specifically to dynamic support apparatuses.

BACKGROUND INFORMATION

This support apparatus may be used for upper-limb and lower-limb prosthetic devices, or any device with interaction with the body, but for exemplary purposes, the present apparatus will be described in the context of prostheses for upper-limb amputees.

Accordingly, there is a need for a dynamic support apparatus that accommodates users' needs in the interaction with the user. A device that can, in addition to other features, include changing geometry in response to a user, including, but not limited to, residuum morphing or external mechanical prosthesis loading to maintain a secure, comfortable fit with the users body, and/or maintain a comfortable temperature and moisture environment between the support apparatus and the users body is desired.

SUMMARY OF THE INVENTION

In accordance with another aspect of the invention, a control unit system is disclosed. The system includes a control unit which includes a control unit charging interface, at least one magnet located proximate to the control unit charging interface, at least one actuator, a detachable manifold including at least one magnet, fluidly coupled to the at least one actuator, a pump connected to the at least one actuator for causing actuation thereof, and a control system for controlling the pump, wherein the control system controls the pump to actuate the at least one actuator at least in response to a signal received by the control system. The system also includes a recharging device configured to receive the control unit, the recharging device including a reed switch, wherein when the magnet in the control unit is located proximate to the reed switch, the switch is activated.

Some embodiments of this aspect of the present invention may include one or more of the following features. Wherein the detachable manifold fluidly couples a plurality of actuators to the pump through a plurality of interior channels. Wherein the system further includes a valve in fluid communication with each interior channel for controlling flow therethrough. Wherein the control system controls activation of the valves. Wherein the system further includes at least a first magnet disposed within at least one of the control unit and the detachable manifold and wherein the first magnet interacts with the other of the control unit and the detachable manifold to secure the detachable manifold to the control unit. Wherein the other of the control unit and the detachable manifold includes at least a second magnet for interacting with the first magnet to secure the detachable manifold to the control unit. Wherein the other of the control unit and the detachable manifold includes a metal feature for interacting with the first magnet to secure the detachable manifold to the control unit. Wherein the control system commands the pump to increase the pressure of the at least one actuator if the pressure detected by a sensor drops below a current pressure setpoint by more than a prescribed deadband. Wherein the control system commands venting of the at least one actuator if the pressure detected by the sensor exceeds the current pressure setpoint by more than the prescribed deadband. Wherein the control system commands the pump at a fixed time interval.

In accordance with one aspect of the present invention, a system for providing support to a user is disclosed. The system includes at least two groups of at least one bladder, a control unit including at least one actuator, a detachable manifold comprising at least one magnet, fluidly coupling the at least two groups of at least one bladder to the at least one actuator, a pump connected to the at least one actuator for causing actuation thereof, a control system for controlling the pump, wherein the control system controls the pump to actuate the at least one actuator at least in response to a signal received by the control system, and a switch configured to toggle the pump actuation between a first group and a second group of at least one bladder.

Some embodiments of this aspect of the present invention may include one or more of the following features. Wherein the detachable manifold fluidly couples a plurality of actuators to the pump through a plurality of interior channels. Wherein the system further includes a valve in fluid communication with each interior channel for controlling flow therethrough. Wherein the control system controls activation of the valves. Wherein the system further includes at least a first magnet disposed within at least one of the control unit and the detachable manifold, wherein the first magnet interacts with the other of the control unit and the detachable manifold to secure the detachable manifold to the control unit. Wherein the other of the control unit and the detachable manifold includes at least a second magnet for interacting with the first magnet to secure the detachable manifold to the control unit. Wherein the other of the control unit and the detachable manifold includes a metal feature for interacting with the first magnet to secure the detachable manifold to the control unit. Wherein the control system commands the pump to increase the pressure of the at least one actuator if the pressure detected by a sensor drops below a current pressure setpoint by more than a prescribed deadband. Wherein the control system commands venting of the at least one actuator if the pressure detected by the sensor exceeds the current pressure setpoint by more than the prescribed deadband. Wherein the control system commands the pump at a fixed time interval.

In accordance with one aspect of the present invention, a control unit for a dynamic support apparatus having at least one actuator includes a pump connected to the at least one actuator for causing actuation thereof. The control unit also includes a sensor detecting a pressure of the at least one actuator and a control system for controlling the pump to actuate the at least one actuator at least in response to the pressure detected by the sensor.

In accordance with another aspect of the invention, the control unit includes a detachable manifold fluidly coupling the at least one actuator to the pump to control the distribution of air to the at least one actuator. In some embodiments, the detachable manifold may be attached to the control unit using magnetic force. The control unit may also include at least one valve allowing the control system to control airflow through the detachable manifold.

In accordance with another aspect of the present invention, at least one sensor provides information on the stability and fit of the support apparatus to the control system. In accordance with a further aspect of the present invention, the at least one sensor is a pressure transducer. In accordance with another aspect of the present invention, the control system maintains a constant pressure measured by the pressure transducer. In accordance with another aspect of the present invention, the control system increases the pressure of at least one actuator if the pressure detected by the sensor drops below a current pressure setpoint by more than a pre-determined error threshold.

In accordance with a further aspect of the present invention, the control system actuates a change in geometry of the dynamic interface based on the information provided by the at least one sensor. In one aspect of the present invention, the control system evaluates a user activity level based at least on the information provided by the at least one sensor. In another aspect of the present invention, the evaluation of the user activity level is also based on a pressure variability and a duration of the pressure variability. According to another aspect of the present invention, the control system increases the pressure of at least one actuator if a high activity threshold is exceeded and decreases the pressure of at least one actuator if a low activity threshold is exceeded.

In yet another aspect of the present invention, the control system evaluates whether a safety threshold has been exceeded based at least on the information provided by the at least one sensor. In another aspect of the present invention, the evaluation of whether the safety threshold has been exceeded is also based on a temperature. In one aspect of the present invention, the control system enters an auto-relief mode if the safety threshold has been exceeded.

In another aspect of the present invention, a method for control of at least one actuator of a dynamic support apparatus includes monitoring a pressure of the at least one actuator and altering the pressure of the at least one actuator based at least in part on the monitored pressure. According to some aspects of the present invention, the method includes increasing the pressure of the at least one actuator if the monitored pressure drops below a current pressure setpoint by more than a pre-determined error threshold. In another aspect of the present invention, the method includes evaluating a user activity level based at least on the pressure of the at least one actuator. In yet another aspect of the present invention, the method includes evaluating whether the safety threshold has been exceeded based at least on the pressure of the at least one actuator.

These aspects of the invention are not meant to be exclusive and other features, aspects, and advantages of the present invention will be readily apparent to those of ordinary skill in the art when read in conjunction with the appended claims and accompanying drawings.

BRIEF DESCRIPTION OF THE DRAWINGS

These and other features and advantages of the present invention will be better understood by reading the following detailed description, taken together with the drawings wherein:

FIG. 12A is a top view of one embodiment of the dynamic interface of a dynamic support apparatus;

FIG. 12B is a side view of the dynamic interface of FIG. 12A with respect to the frame of an embodiment of a dynamic interface;

FIG. 13 is a bottom view of one embodiment of the dynamic interface of a dynamic support apparatus;

FIG. 29 is a perspective view of one embodiment of an un-actuated active strap of a dynamic support apparatus;

FIG. 30 is a cross-sectional view of the active strap of FIG. 29;

FIG. 31 is a perspective view of the active strap of FIGS. 29 and 30 when actuated;

FIG. 32 is a cross sectional view of the actuated active strap of FIG. 31;

FIG. 33 is a perspective view of one embodiment of an active strap and control system of a dynamic support apparatus;

FIG. 34 is a perspective view of an alternative embodiment of an active strap and control system of a dynamic support apparatus;

DETAILED DESCRIPTION OF EXEMPLARY EMBODIMENTS

Figure 1:
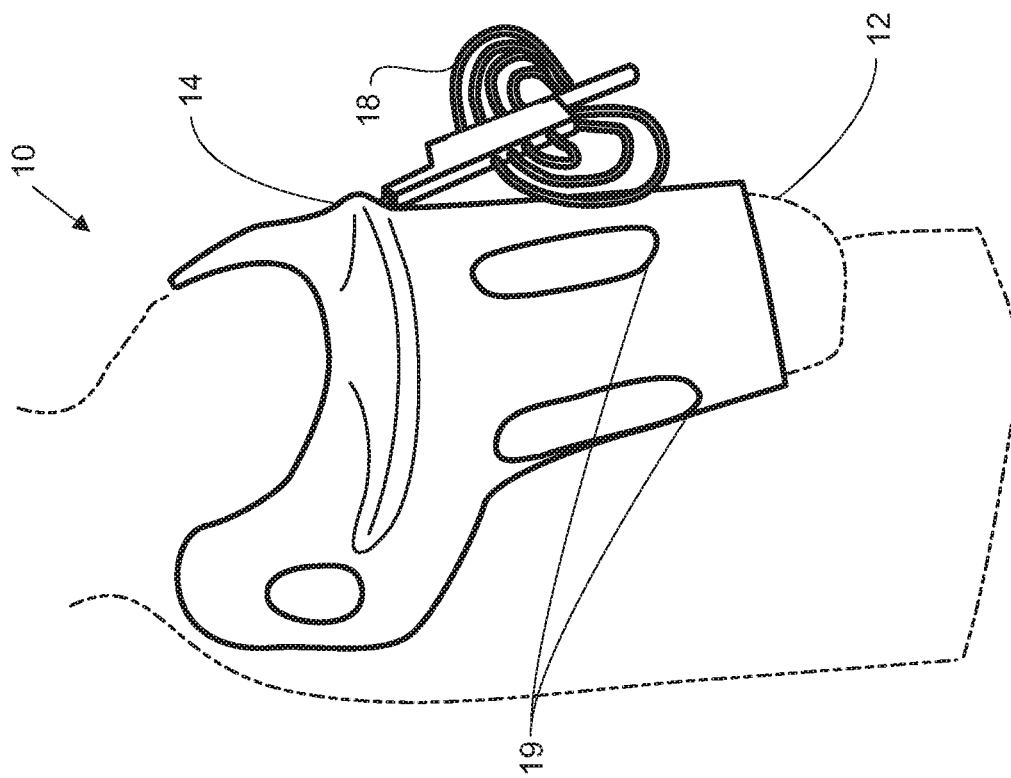
FIG. 1 is a perspective view of one embodiment of a dynamic support apparatus representative of a transhumeral configuration.

For exemplary purposes, the support apparatus will be described in the embodiment of a support apparatus 10 for an upper-limb trans-humeral (TH) prosthesis, as seen in FIG. 1, such as the various prosthetic arms described in U.S. patent application Ser. No. 12/027,141, filed Feb. 6, 2008 and entitled Arm Prosthetic Device, now U.S. Publication No. US-2008-0288088-A1, published Nov. 20, 2008, U.S. patent application Ser. No. 12/706,609, filed Feb. 16, 2010 and entitled Arm Prosthetic Device, now U.S. Publication No. US-2010-0274365-A1, published Oct. 28, 2010, and U.S. patent application Ser. No. 13/088,063, filed Apr. 15, 2011 and entitled Arm Prosthetic Device, now U.S. Publication No. US-2011-0257765-A1, published Oct. 20, 2011, each of which is hereby incorporated by reference in its entirety. However, in various embodiments, the support apparatus, as well as the various embodiments of the control unit, may be used with various other apparatus and is not limited to use with an arm prosthetic device.

Figure 2:
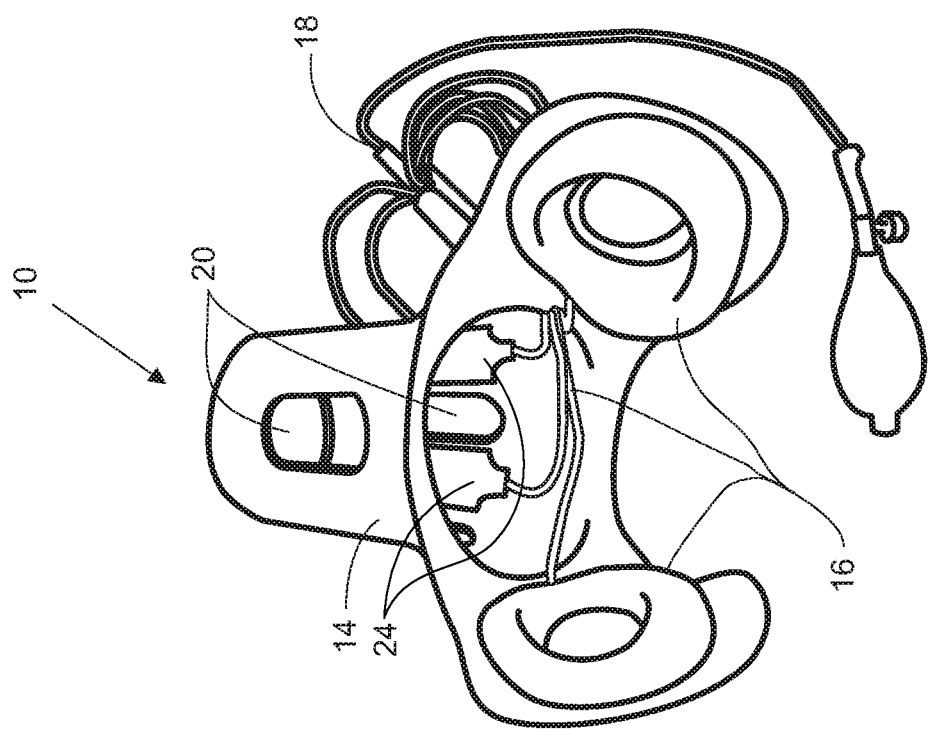
FIG. 2 is a top view of the embodiment of the dynamic support apparatus of FIG. 1.
Figure 63:
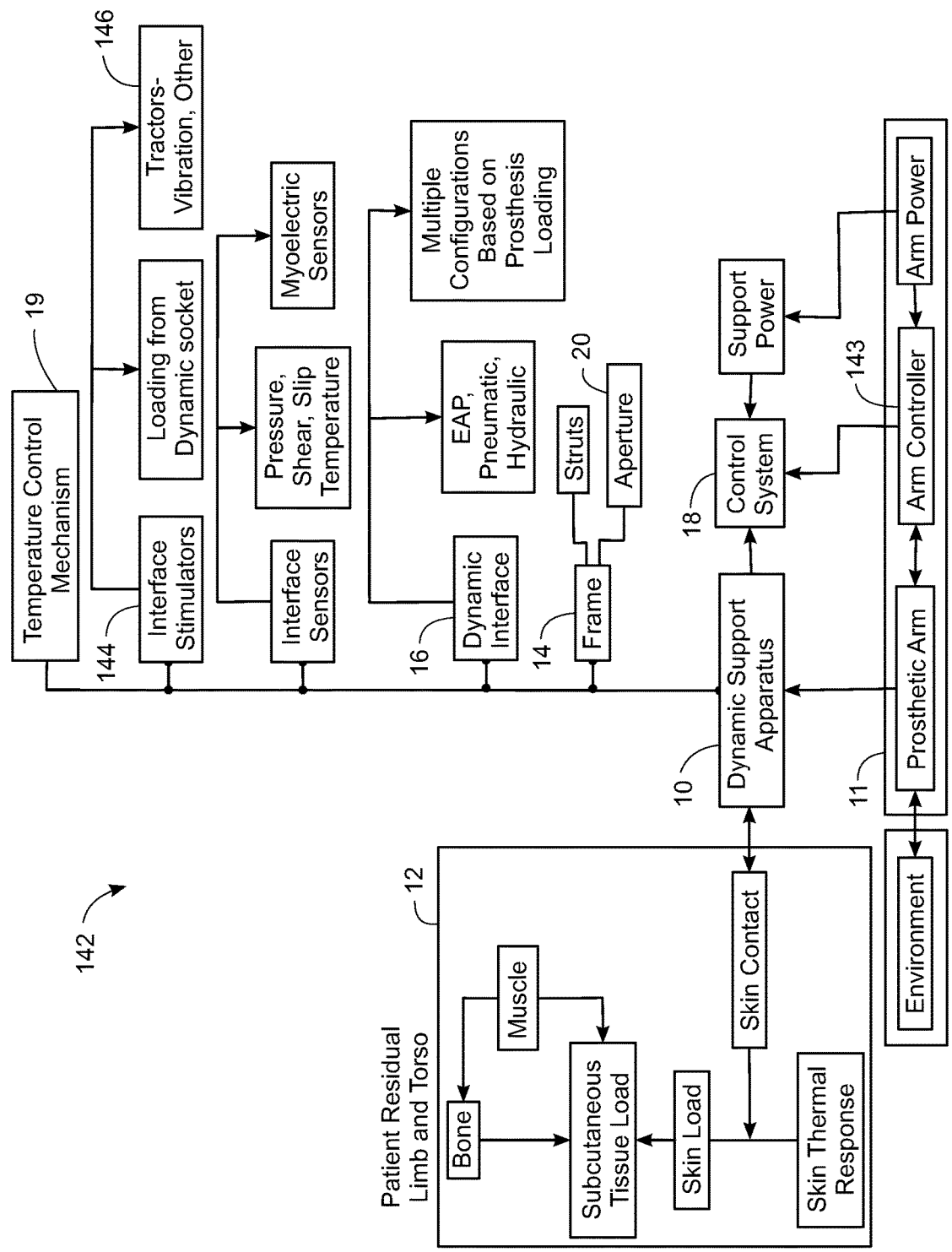
FIG. 63 is a schematic diagram of a dynamic support system according to an embodiment of the present invention.

Referring to FIG. 2, the support apparatus 10, which is utilized to removably adhere to prosthesis 11, shown in FIG. 63, to an upper-limb residuum 12 (FIG. 1), includes a frame 14, a dynamic interface 16, a control system 18, and a temperature control mechanism 19. The frame is generally rigid and may be made of high tech composite material such as carbon fiber.

In one embodiment, the frame 14 may be open and have a plurality of apertures 20. The structural members of the frame of this embodiment may be strategically placed to maximize the openness of the apparatus. Additionally, the plurality of apertures 20 may be the temperature control mechanism or function as a part of the temperature control mechanism.

The dynamic interface 16 is disposed on a top surface 22 of the frame closest to the upper-limb residuum 12. The dynamic interface 16 includes one or more actuators 24 of various shapes and sizes that can be positioned either longitudinally and/or circumferentially along the frame 14. The actuators 24 are capable of changing their geometry and volume to secure the support apparatus 10 to the residuum 12, shown in FIG. 1, and to account for morphing in the residuum 12.

As discussed above, the support apparatus 10 includes apertures 20 to address both structural and temperature concerns. In addition, the apertures 20 may be designed to provide relief to the residuum 12, shown in FIG. 1, when the support apparatus 10 is secured thereonto. For instance, the apertures 20 may provide space to allow the soft tissue of the residuum 12, shown in FIG. 1, to move away from the actuators 24, thereby minimizing the amount of soft tissue between the load bearing surfaces of the support apparatus 10, i.e. the actuators 24, and the bone within the residuum 12, shown in FIG. 1. Thus, the apertures 20 allow the soft tissue of the residuum 12 to escape the areas of contact with the actuators 24, thereby providing relief to the user and allowing the actuators 24 to engage to bone within the residuum 12, shown in FIG. 1.

Although described as apertures 20, in some embodiments, the support apparatus 10 may additionally include at least one hollow cavity to provide another means for soft tissue escape. Thus, as the actuators 24 change their geometry to secure the support apparatus 10 to the residuum 12, shown in FIG. 1, the soft tissue may be displaced into the hollow cavities during actuation to provide relief to the user.

Figure 3:
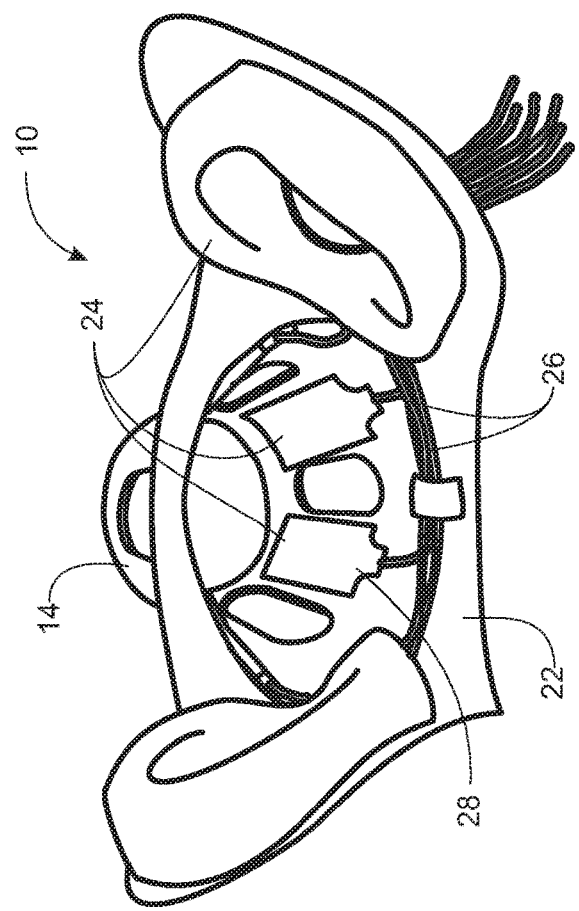
FIG. 3 is an internal view of the embodiment of the dynamic support apparatus of FIGS. 1 and 2.

Referring to FIG. 3, the actuators 24 may be bladders 28 filled with air, gas or incompressible liquid, electroactive polymers (EAPs), or other types of actuators capable of changing their geometry. The dynamic interface also includes one or more connectors 26 that connect the actuator(s) 24 to the control system 18. The connector(s) may be fluid paths, tubes, wires, or other similar channels.

Figure 4:
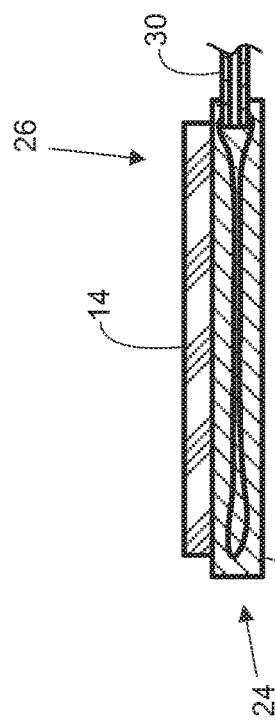
FIG. 4 is a cross-sectional view of one embodiment of an actuator of the dynamic support apparatus in an inactuated state.
Figure 5:
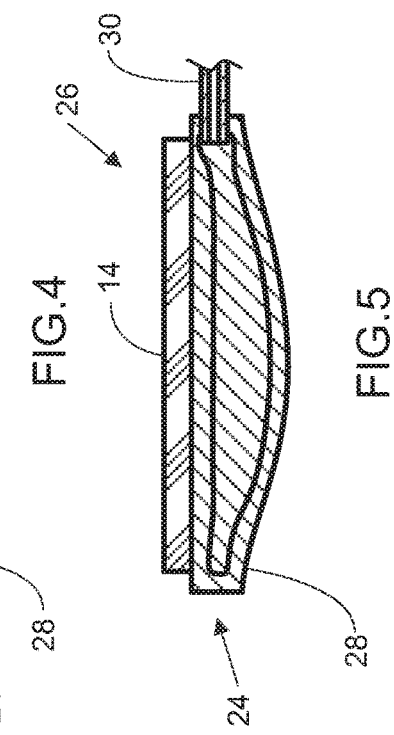
FIG. 5 is a cross-sectional view of the actuator of FIG. 4 of the dynamic support apparatus in an actuated state.
Figure 6:
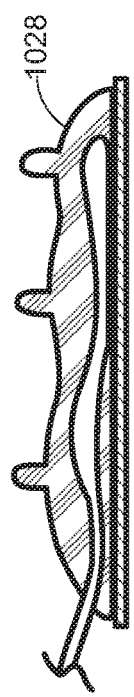
FIG. 6 is a cross-sectional view of another embodiment of an actuator of the dynamic support apparatus in an inactuated state.
Figure 7:
FIG. 7 is a cross-sectional view of the actuator of FIG. 6 of the dynamic support apparatus in an actuated state.

Referring to FIGS. 4 and 5, in an embodiment having bladders 28 for actuators 24 and fluid path connectors 30 for connectors 26, the bladder 28 will change geometry from an inactuated position shown in FIG. 4 to the actuated position shown in FIG. 5 when filled with air. Although the bladder 28 is shown with a substantially uniform cross section in FIGS. 4 and 5, the same functionality may be obtained from the bladder 1028 having a non-uniform cross-section shown inactuated in FIG. 6 and actuated in FIG. 7, wherein the like numerals represent the like elements.

Figure 10:
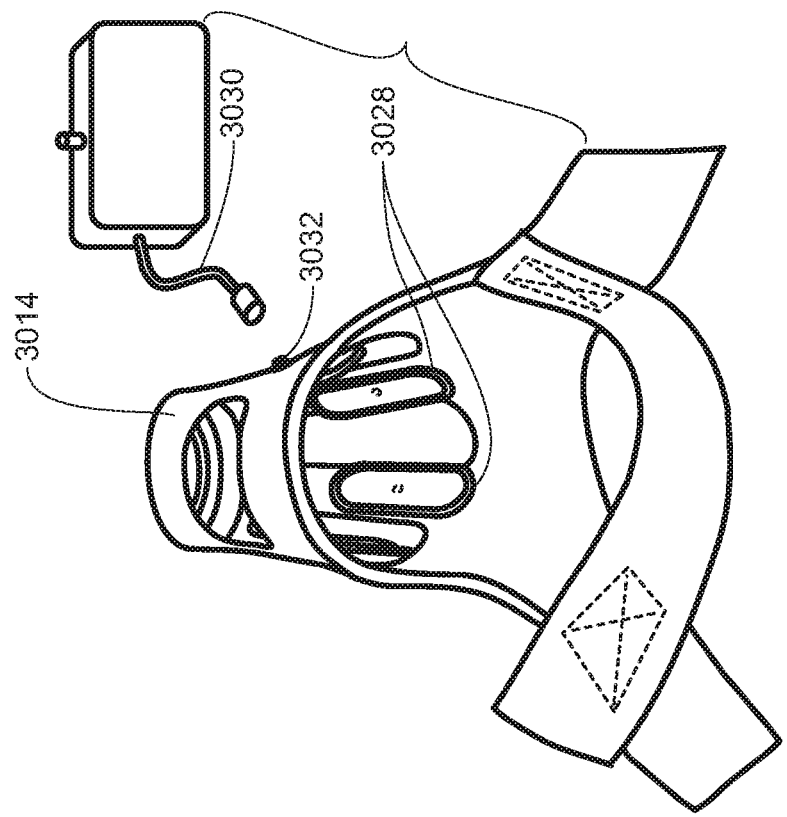
FIG. 10 is a perspective view of a dynamic support apparatus with the actuators of FIG. 9 installed.
Figure 8:
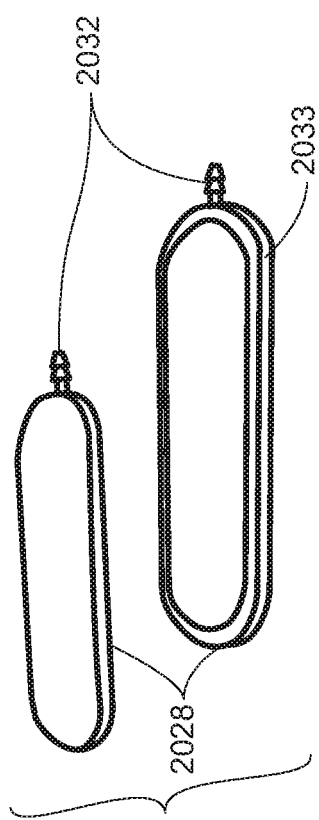
FIG. 8 is a perspective view showing the top and bottom of one embodiment of an actuator of the dynamic support apparatus.
Figure 9:
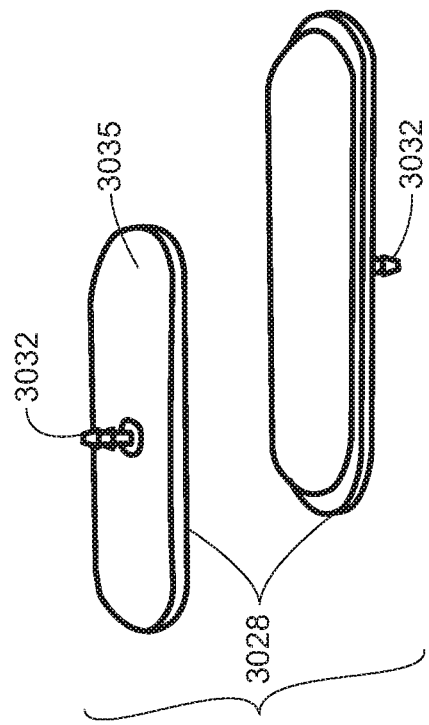
FIG. 9 is a perspective view showing the top and bottom of another embodiment of an actuator of the dynamic support apparatus.

Referring to FIG. 8, in a further embodiment, the bladders 2028 may have bladder inlets 2032 to facilitate the connection of the fluid path connectors 30, shown in FIGS. 4 and 5. The bladder inlets 2032 may be located at any position on a periphery 2033 of each bladder 2028 to accommodate the desired fluid path connector routing configuration. Referring to FIG. 9, an alternative embodiment positions the bladder inlet 3032 on a body 3035 of the bladder 3028. In this embodiment, as seen in FIG. 10, the bladder inlet 3032 may pass through the frame 3014 to facilitate connection to the fluid path connectors 3030.

In one embodiment, the frame has an outer shell and an inner shell. Here, the dynamic interface may be disposed between the outer shell and the inner shell. The inner shell may also have apertures to dictate the shape the actuator(s).

For example, if the actuator(s) are bladders, the inner shell apertures would dictate the shape of the bladder as it is inflated.

Figure 11:
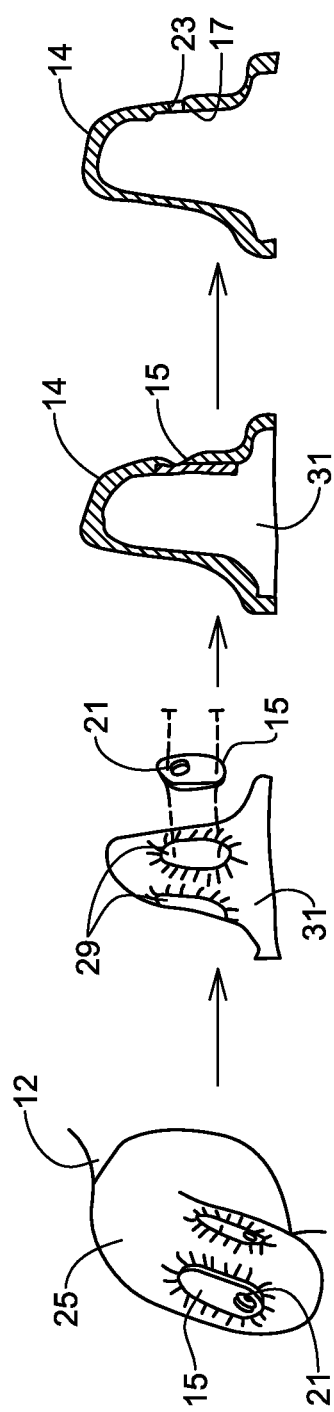
FIG. 11 is an illustration of a technique for fabricating a portion of a dynamic interface according to an embodiment of the present invention.

Referring to FIG. 11, in some embodiments the frame 14 may be formed according to a casting process using one or more casting blanks 15 to provide bladder accommodations 17 within the frame 14 that have planar surfaces upon which the bladders 28, shown in FIG. 3, may sit. The planar surfaces of these bladder accommodations 17 advantageously prevent the bladders 28, shown in FIG. 3, from un-adhering thereto, which is more likely with curved surfaces. The one or more casting blanks 15 are formed to have a size and shape that is substantially the same as the bladders 28, shown in FIG. 3, and any fastening mechanism that will fasten the bladders 28, shown in FIG. 3, to the frame 14, such as Velcro and/or glue. Additionally, each casting blank 15 has a tapered hole 21 formed therein to facilitate the formation of holes 23 for allowing the bladders 28, shown in FIG. 3, to be connected to connectors 26, shown in FIG. 3.

During the casting process, a prosthesist or clinician forming the frame 14 covers the portion of the residuum 12 that is being cast with one or more plaster wraps 25. The prosthesist presses the one or more casting blanks 15 into the outer surface of the plaster wraps 25 at locations where bladders 28, shown in FIG. 3, are to contact the residuum 12 within the fully formed dynamic support apparatus 10, shown in FIG. 3. The prosthesist allows the plaster wraps 25 to cure with the casting blanks 15 pressed therein such that bladder impressions 27 are formed within the fully cured plaster wraps 25. While allowing the plaster wraps 25 to cure, the prosthesist preferably ensures that the casting blanks 15 remain parallel to the bone within the residuum 12. The cured plaster wraps 25 may then be filled to form a plaster positive 31, which will also have the bladder impressions 29 formed therein. The casting blanks 15 may then be secured to the plaster positive 31 and the frame 14 may be cast therearound to form the bladder accommodates 17 on the inner surface of the frame 14. In some embodiments, the casting blanks 15 may include one or more tack holes for allowing one or more tacks to pass therethrough to secure to the casting blanks 15 to the plaster positive 31. As discussed above, the tapered holes 21 of the casting blanks 15 form dimpled impressions in the outer surface of the frame 14, thereby advantageously locating the drilling locations for the holes 23.

The casting blanks 15 and the casting process discussed in connection with FIG. 11, advantageously allows for the formation of bladder accommodations 17 that are straight and parallel to the bone within the residuum 12, rather than following the curved outer surface of the residuum 12. This allows the bladders 28, shown in FIG. 3, positioned within the bladder accommodations 17 to better engage the residuum 12, and the bone therein, to provide a more secure and better load bearing fit for the dynamic support apparatus 10, shown in FIG. 3, as compared to a support formed with the curved outer surface of the residuum 12, which would tend to push the residuum 12 out of the socket when actuated.

In another alternative embodiment, referring to FIGS. 12A and 12B, the dynamic interface 4016 is a single integrated layer 4034 disposed on the top surface 4022 of the frame 4014. For example, in an embodiment having bladders 4028 with fluid path connectors 4030, the bladders 4028 and fluid paths connectors 4030 are embedded into a single layer of material that is placed on top of the frame 4014. The single integrated layer 4034 may be made of any material that allows for morphable chambers that can house or act as actuators of variable geometry. Such material may be silicone or rapid prototype molding material covered with a layer of silicone. The single integrated layer 4034 may also have nodules 4036 to attach to the frame 4014 having corresponding apertures 4037 for the nodules 4036. In some embodiments, the nodules 4036 are protrusions. The nodules 4036 do not have to be round bumps as depicted in one embodiment of the apparatus.

Figure 14:
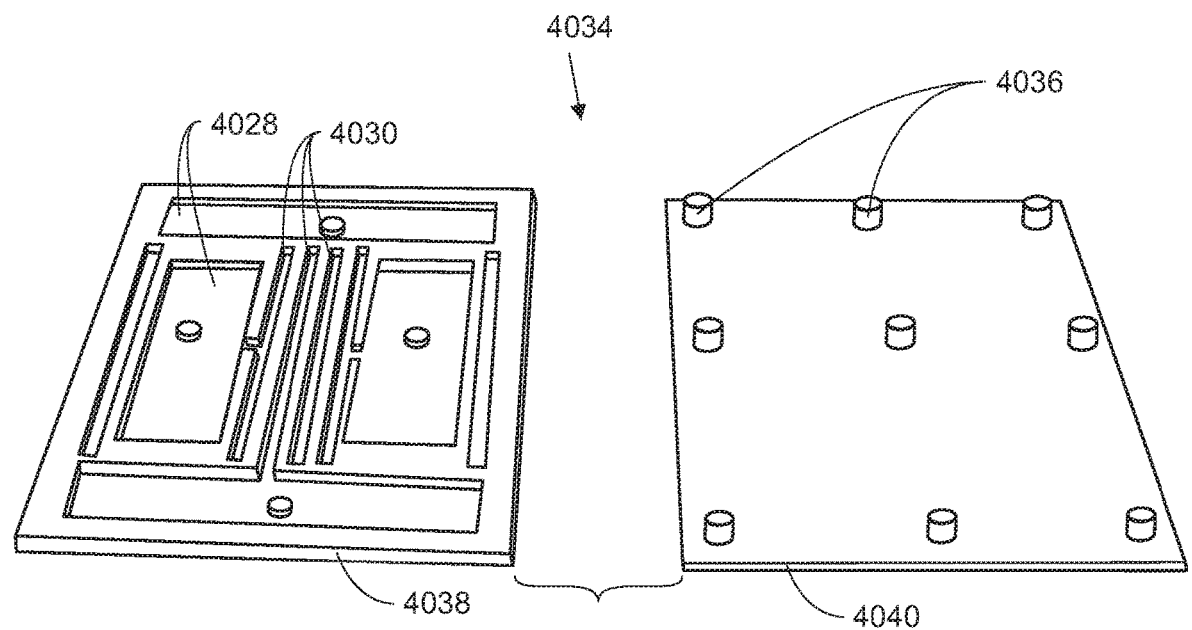
FIG. 14 is an exploded view of the dynamic interface of FIG. 13.

Referring to FIG. 13, the bladders 4028 and fluid path connectors 4030 may be molded as a part of the single integrated layer 4034, such that the layer itself contains internal paths and compartments that serve as the fluid path connectors 4030 and bladders 4028, respectively. The molded single integrated layer 4034 may also have nodules 4036 to attach to a frame having corresponding apertures 4037. As seen in FIG. 14, the single integrated layer 4034 may be constructed by molding an actuation layer 4038, containing the necessary bladders 4028 and fluid path connectors 4030, and a connection layer 4040, containing nodules 4036 for attaching the single integrated layer 4034 to the frame. The actuation layer 4038 and the connection layer 4040 can then be bonded together to form the single integrated layer 4034, as seen in FIG. 13. The molded single integrated layer 4034 may be fabricated from any material that allows morphable chambers that can act as actuators of variable geometry. Such material may be silicone or rapid prototype molding material covered in a layer of silicone. Additionally, bladders, such as the bladders 2028, shown in FIG. 8, or the bladders 3028, shown in FIG. 9, with their unique characteristics, may also be embedded in the molded single integration layer 4034, which may provide the dynamic interface 4016 with characteristics of both the bladders and the molded single integration layer 4034, for example, to increase actuation while increasing stability.

The dynamic interface 16 allows the support apparatus 10 to morph and adapt to the function of the residuum 12. For example, in an embodiment having actuators 24 that are bladders 28 filled with gas, when the residuum 12 morphs, possibly due to tissue volume variation or loading, the bladders 28 either inflate or deflate to adjust to the residuum 12 morphing and to maintain a secure and comfortable fit on the residuum 12.

The control system 18 controls the changing geometry of the actuators 24. The control system 18 may be hydraulic, pneumatic, electromechanical, mechanical, or any other actuator type mechanism that allows the actuators 24 to change geometry. In our exemplary embodiment, the bladders 28 are controlled by a pneumatic system and connected to the system by the fluid paths connectors 30.

Figure 15:
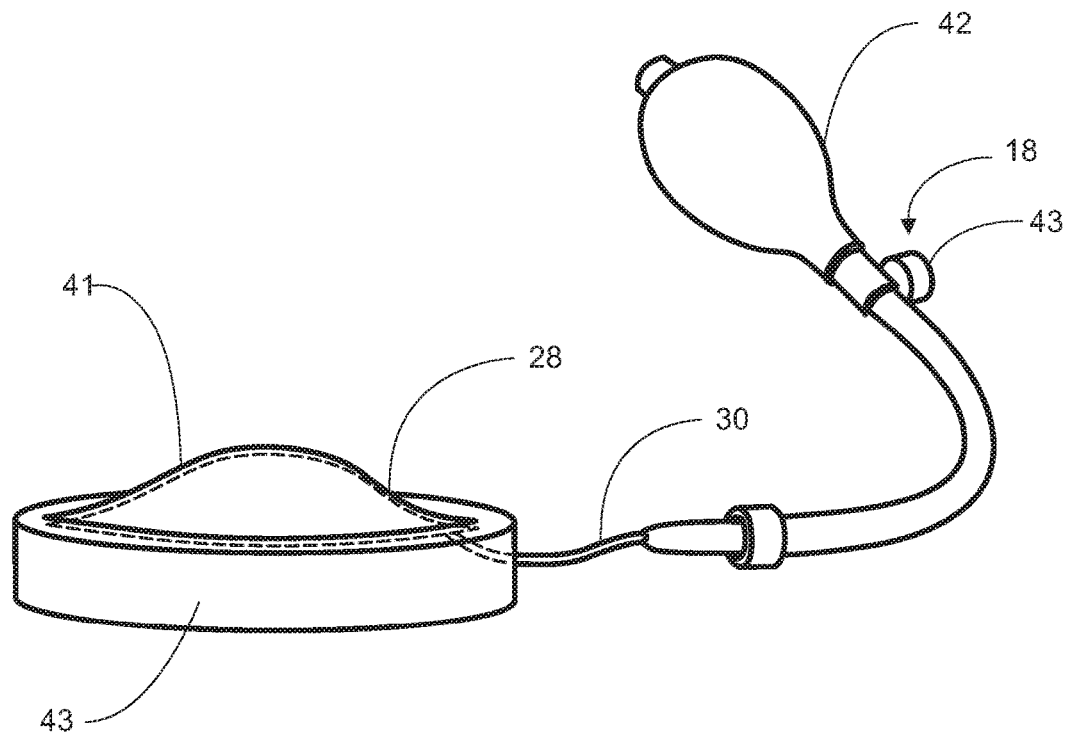
FIG. 15 is a perspective view of one embodiment of an actuator and control system of a dynamic support apparatus.

Referring now to FIG. 15, one embodiment of the control system 18 is shown as a manual system with a pressure bulb 42 that is connected to the bladder 28 by one or more fluid path connectors 30 and one or more valves 43. When the user begins to feel instability with the fit of the support apparatus 10, the user squeezes the pressure bulb 42 to increase the air or liquid pressure in the bladder 28, thus adjusting the fit of the support apparatus 10 to the user's liking. The user may also decrease the pressure in the bladder 28 by opening the valve 43. If more than one bladder 28 is used, the user may be able to adjust the pressure in each individual bladder 28.

Still referring to FIG. 15, in this embodiment, the bladder 28 is laser welded. By laser welding a thin sheet 41 of bladder material to a substantially thicker sheet 45 of bladder material or a stable base material, such as an injection molded flexible plastic, the actuation can be isolated to a desired direction. As seen in FIG. 15, the bladder 28 deforms in the direction of the thin sheet 41 of material, while the remainder of the bladder 28 remains substantially unchanged.

Figure 16:
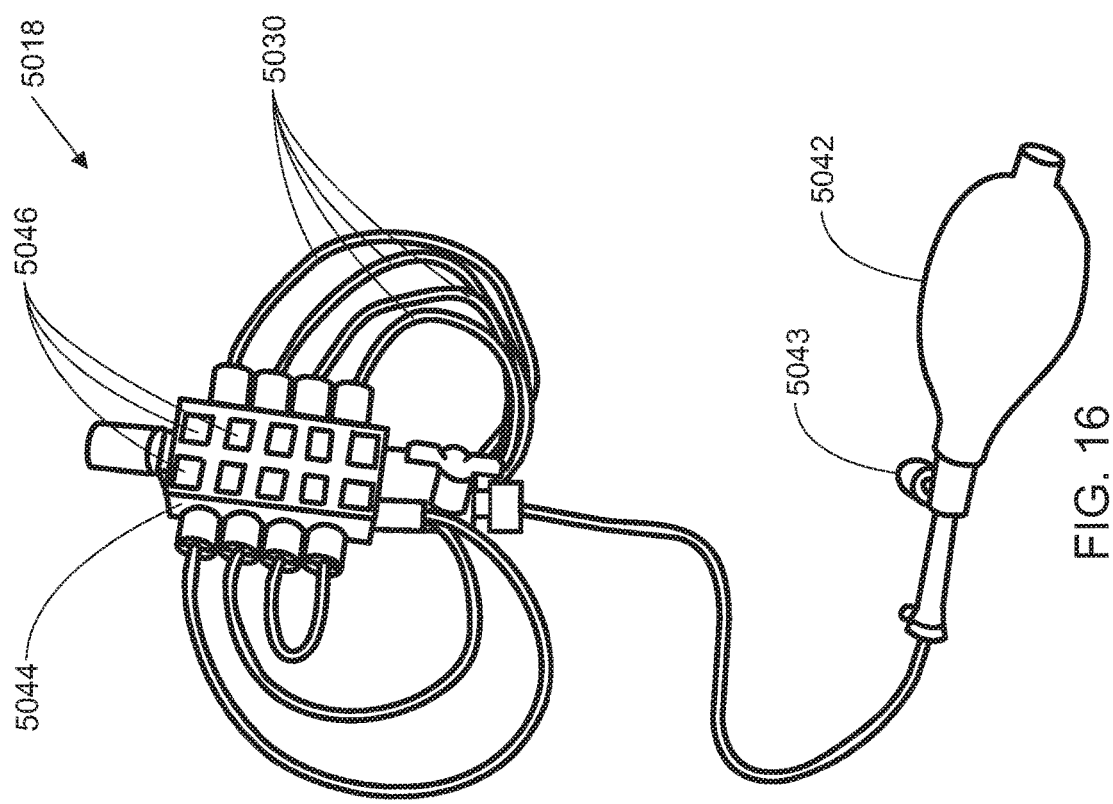
FIG. 16 is one embodiment of a manual control system of a dynamic support apparatus.

Referring now to FIG. 16, in an alternative embodiment of the control system 5018, the pressure bulb 5042 is connected to a plurality of bladders by one or more fluid path connectors 5030 and valves 5043 through a manifold 5044. The manifold may have pressure selectors 5046 allowing the user to adjust the pressure in the plurality of bladders by different amounts with the pressure bulb 5042. The user may thus preset the pressure selectors 5046 to provide optimal adjustment of the support apparatus. Additionally, the pressure selectors 5046 also allow the user to target one or more specific bladder(s) of the plurality of bladders, such that pressure can be adjusted solely in the targeted bladders) while pressure in the rest of the plurality of bladders remains unchanged. This targeting capability permits pinpoint adjustment based on localized instability or discomfort.

Figure 17:
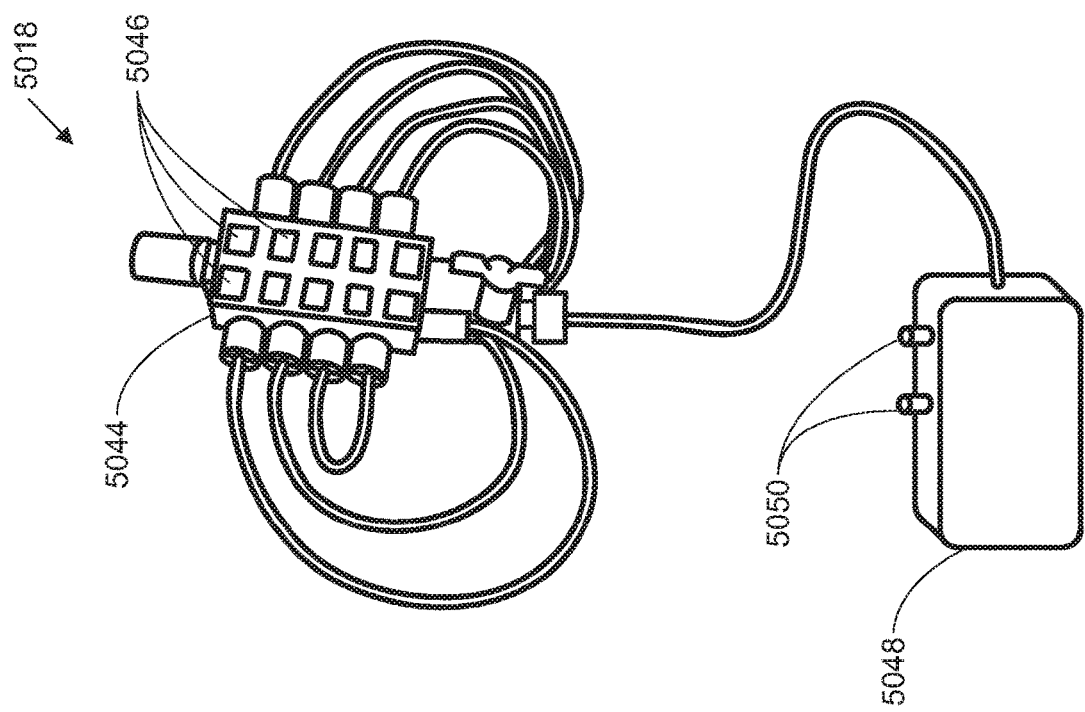
FIG. 17 is one embodiment of a manual control system of a dynamic support apparatus.

Referring now to FIG. 17, the control system 5018 includes an electric pump 5048 in place of the pressure bulb 5042 for adjusting the pressure in the plurality of bladders. Pump control 5050 allows the user to either increase or decrease the pressure in the bladders.

Figure 18A:
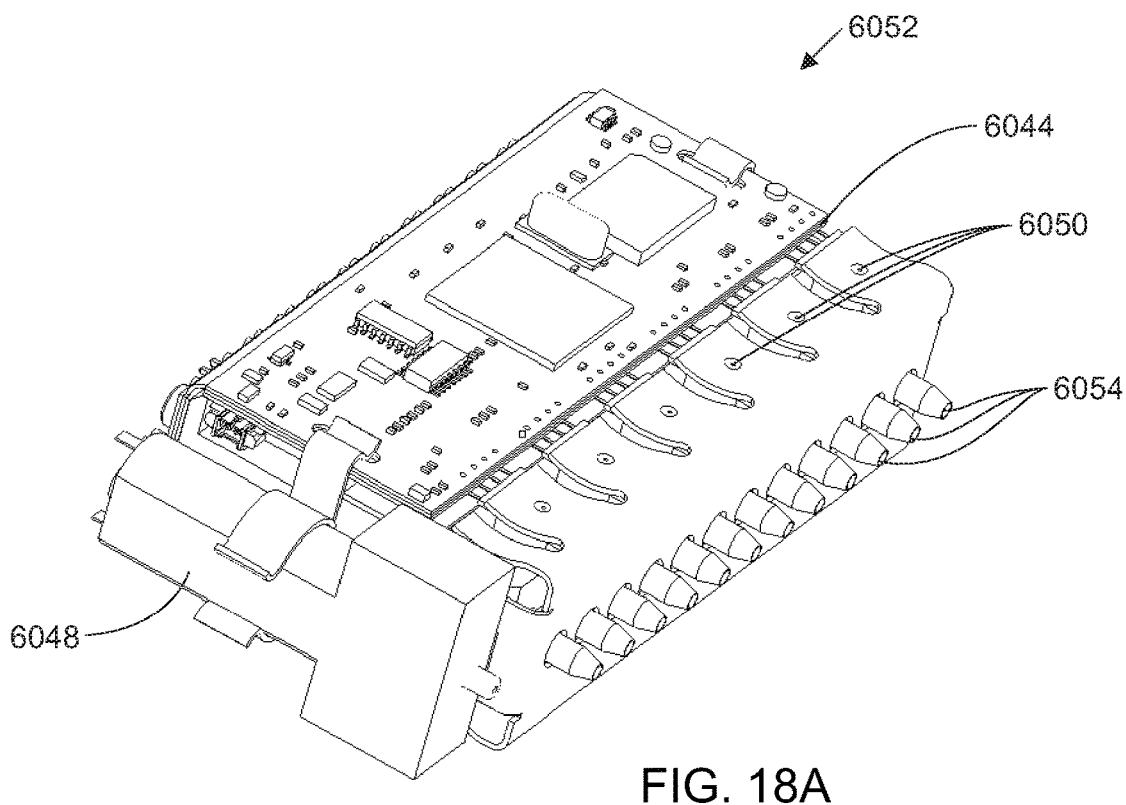
FIG. 18A is an internal perspective view of one embodiment of a control unit of a dynamic support apparatus.
Figure 18B:
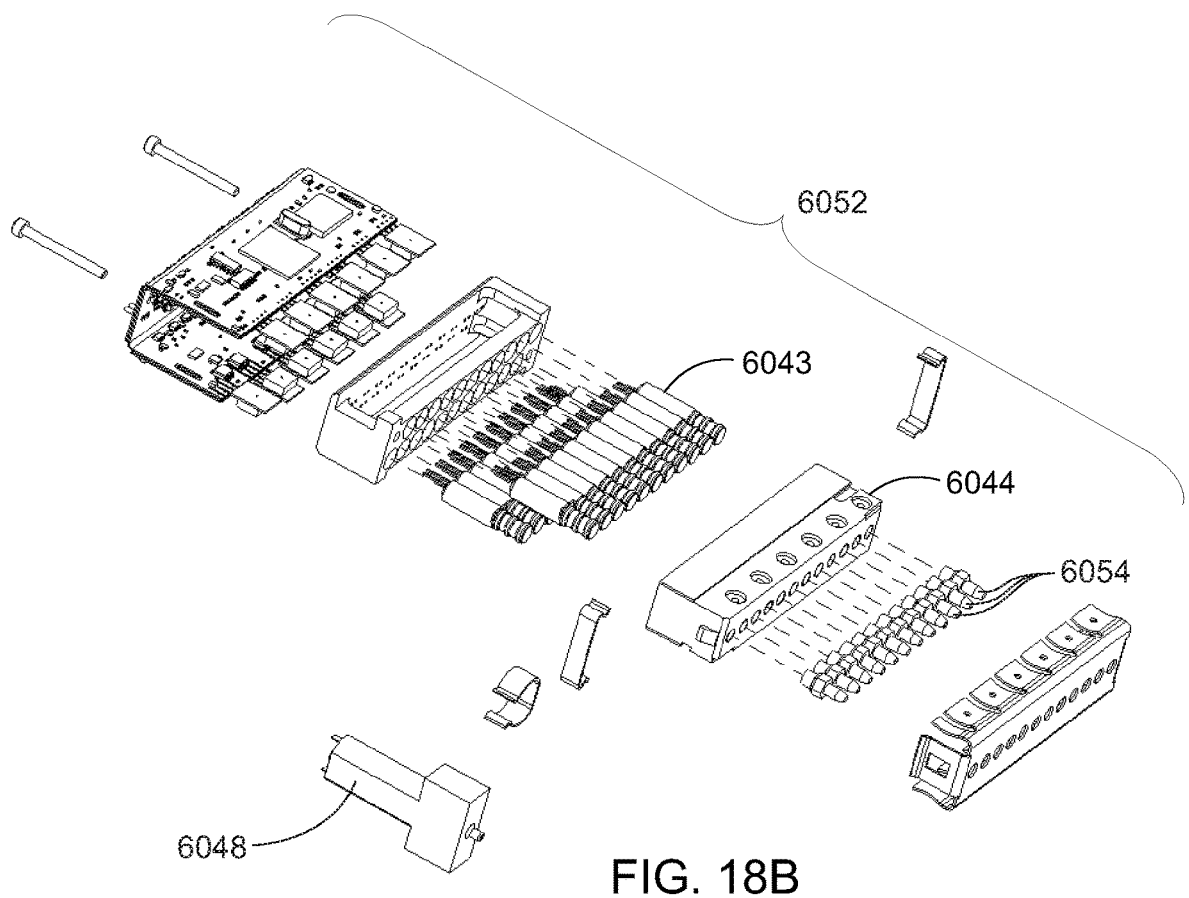
FIG. 18B is an exploded view of the control unit of FIG. 18A.

Referring to FIGS. 18A and 18B, an alternate embodiment incorporates the electric pump 6048, the pump control 6050, one or more valves 6043 and the manifold 6044 into a control unit 6052. The fluid path connectors are attached to manifold outlets 6054, allowing adjustment of each bladder using the pump control 6050. In some embodiments, each manifold outlet 6054 is in fluid communication with the manifold 6044 through at least one valve 6043 such that the user may control inflation and deflation of each bladder individually through activation of the pump 6048 and/or the valves 6043. In some embodiments the manifold 6044, may be located in an accessible location, such as attached to the user's belt, or attached to the support apparatus itself.

Figure 20:
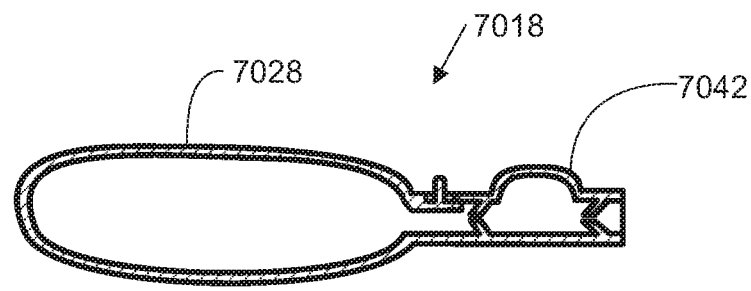
FIG. 20 is a cross-sectional view of one embodiment of an actuator and control system.
Figure 21:
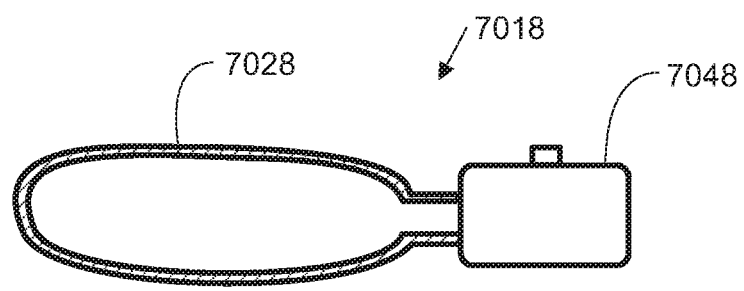
FIG. 21 is a cross-sectional view of one embodiment of an actuator and control system.

Referring now to FIGS. 20 and 21, an alternate embodiment integrates each bladder 7028 and its control system 7018. In the embodiment shown in FIG. 20, the control system 7018 is a pressure bulb 7042. In the embodiment shown in FIG. 21, the control system 7018 is an electric pump 7048. In such an embodiment, the patient would adjust the pressure of each bladder 7028 by actuating its integrated control system 7018.

Figure 19A:
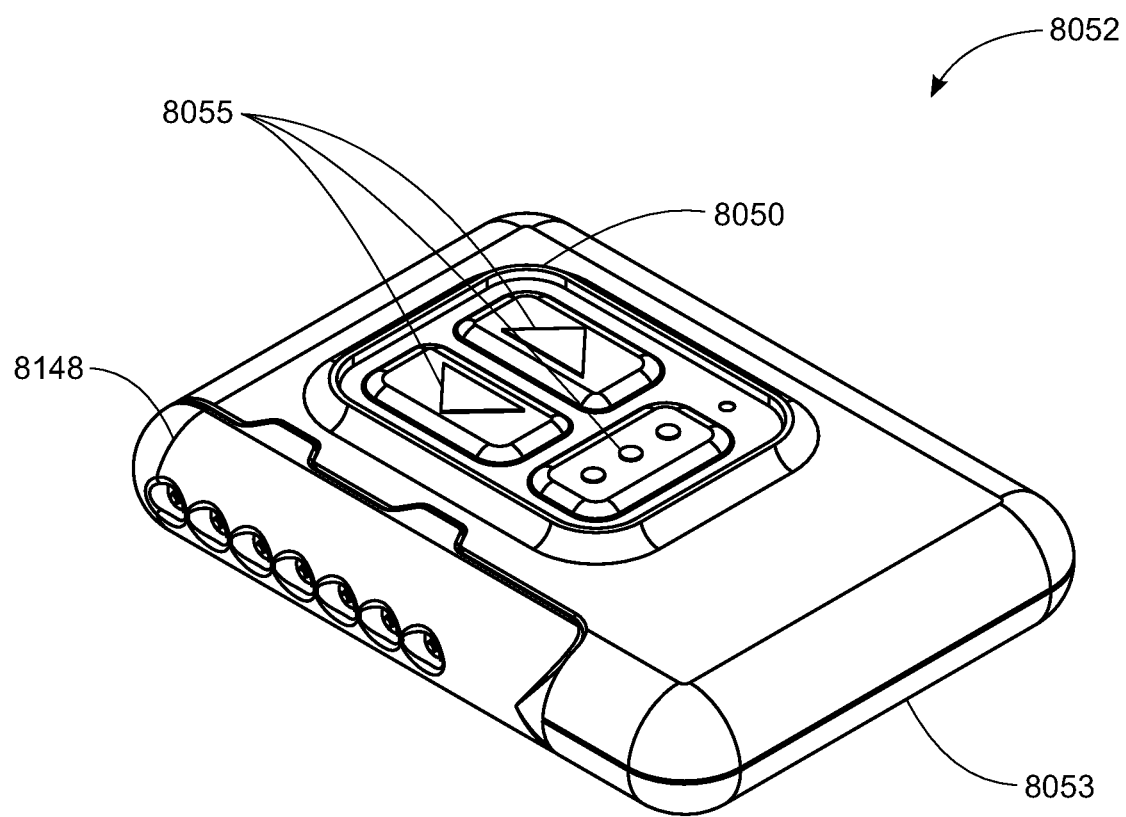
FIG. 19A is a top perspective view of an embodiment of a control unit for a dynamic support apparatus.
Figure 19B:
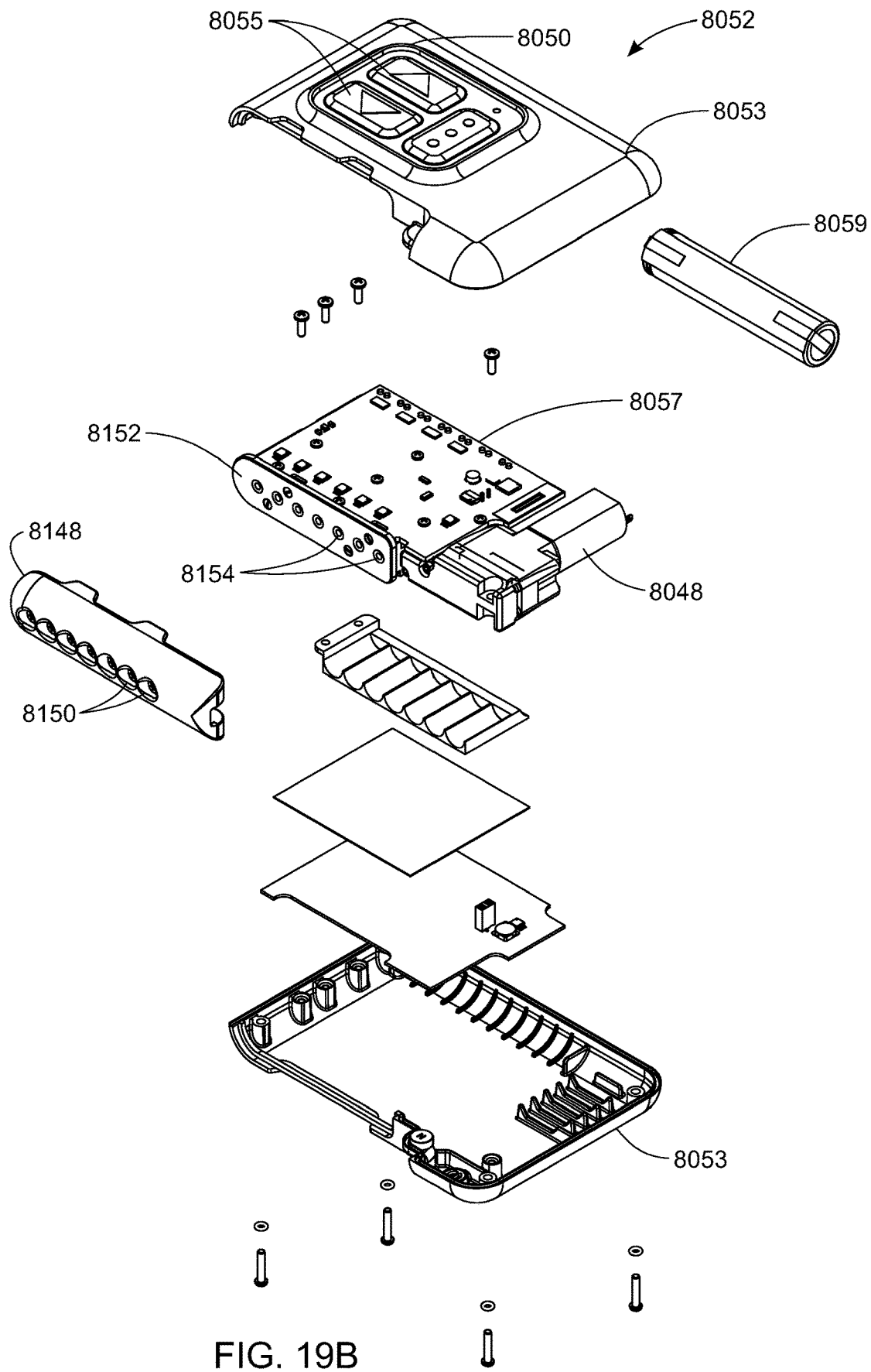
FIG. 19B is a partially exploded view of the control unit of FIG. 19A.
Figure 19C:
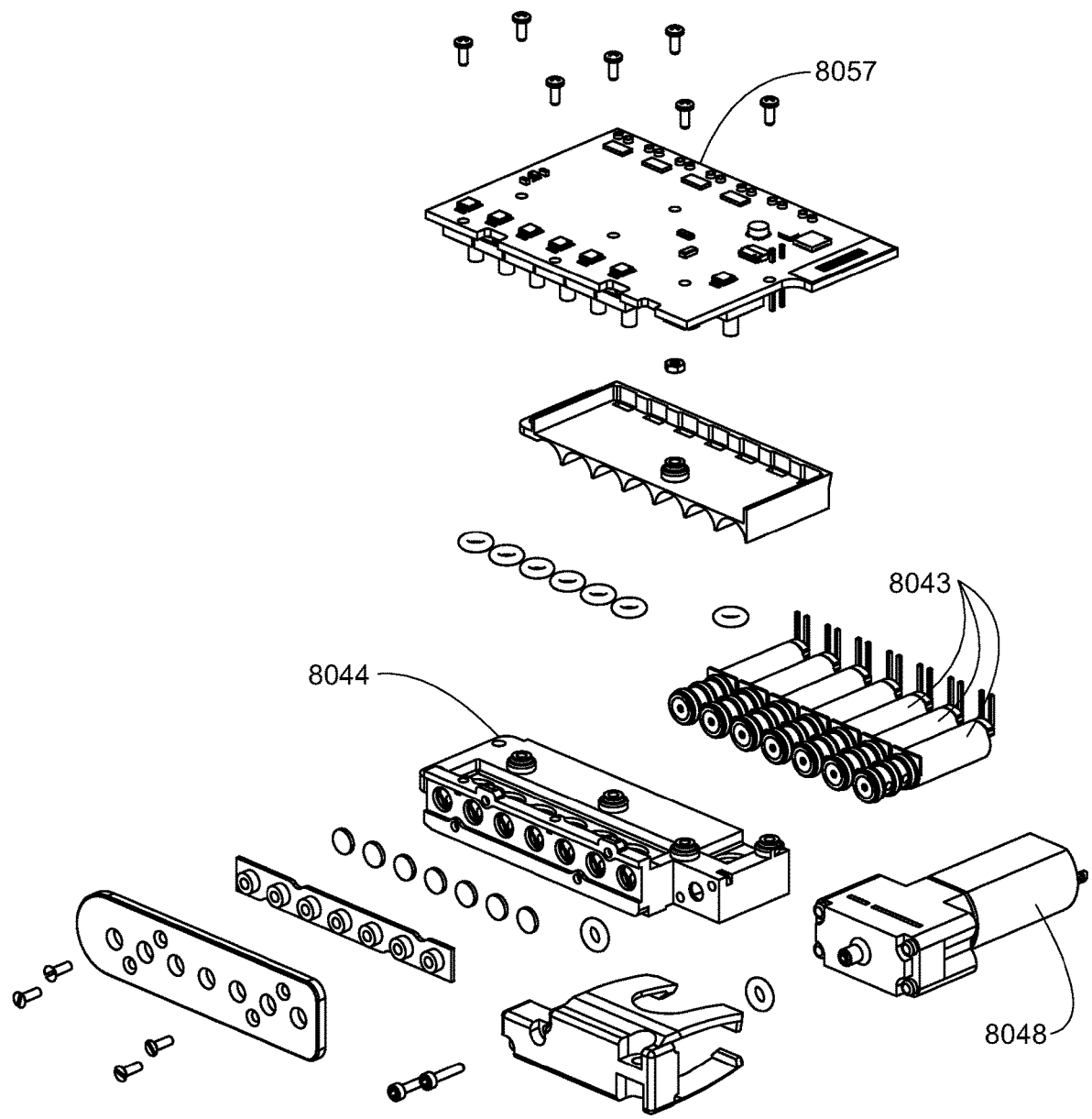
FIG. 19C is an exploded view of an interior of the control unit of FIG. 19B.

Referring to FIG. 19A-19C, in some embodiments, the control unit 8052 includes a housing 8053 having the pump control 8050 integrated therein. Disposed within the housing are the electric pump 8048, shown in FIG. 19B, the one or more valves 8043, shown in FIG. 19C and the manifold 8044, shown in FIG. 19C, as well as electrical connections, such as circuit board 8057, shown in FIG. 19B, one or more processors (not shown), a power supply 8059, shown in FIG. 19B, and the like for connecting the pump control 8050 to the electric pump 8048 and the one or more valves 8043 to allow the user to control the operation thereof. The pump control 8050 may include one or more user inputs 8055 that may include, for example, buttons, each to activate a particular/specific support apparatus control mode, as will be discussed in greater detail below. In some embodiments, the one or more user inputs 8055 may include a "function" or "toggle" switch so as to use the same button or user input 8055 for multiple functionalities. In some embodiments, the power supply 8059 for the control unit 8052 may advantageously include a rechargeable lithium battery.

Figure 19D:
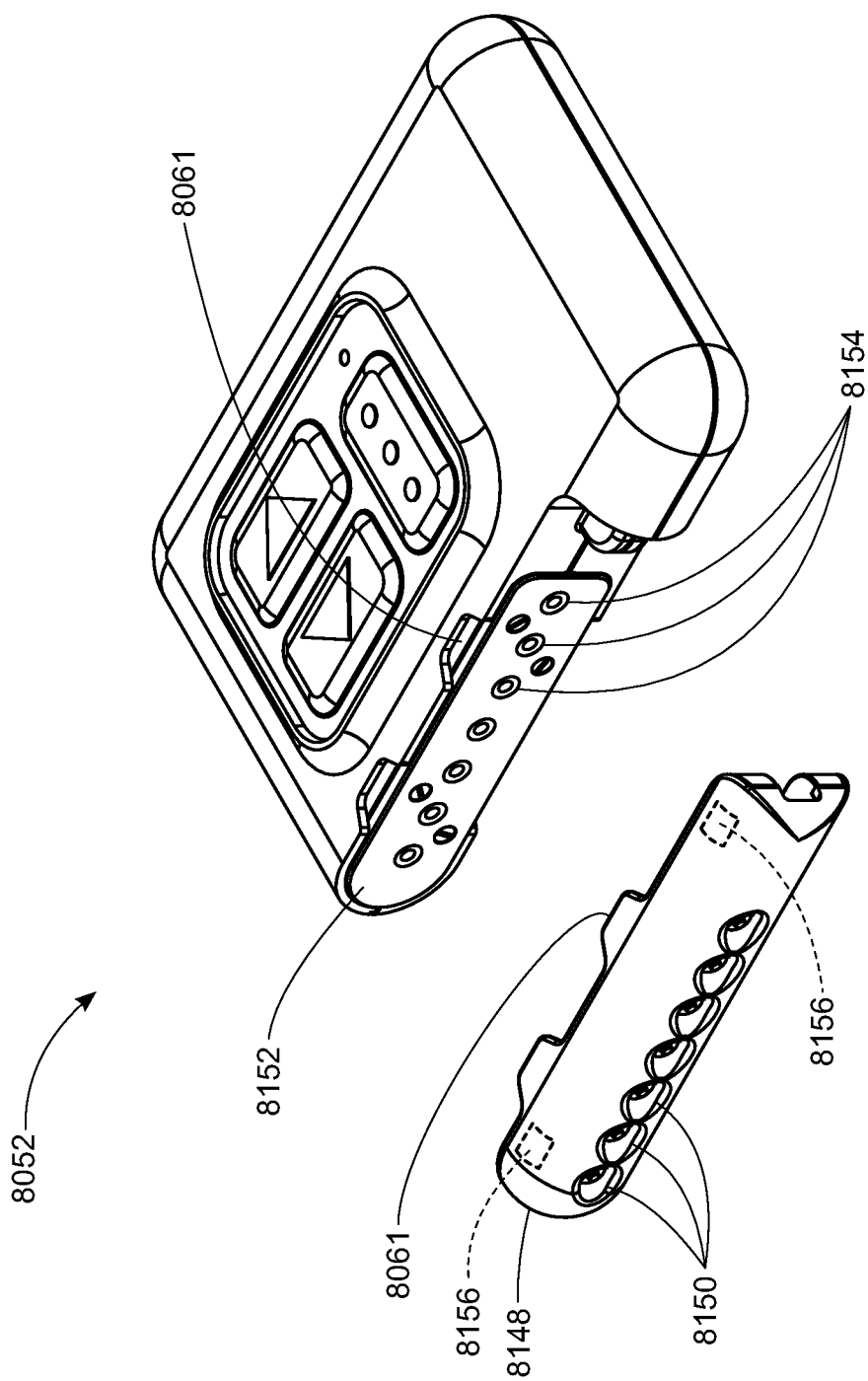
FIG. 19D is a top perspective view of the control unit of FIG. 19A with a detachable manifold removed therefrom.

Referring to FIG. 19D, the control unit 8052 may include a detachable manifold 8148 to facilitate connection of the connectors 26, shown in FIG. 3, such as flexible tubing, to the control unit 8052. The detachable manifold 8148 may include a plurality of interior channels 8150 extending therethrough to which the connectors 26 may be coupled. The detachable manifold 8148 mates with a gasket 8152 of the control unit 8052 such that the interior channels 8150 align and communicate with fluid channels 8154 of the control unit 8052. The gasket 8152 may be a planar gasket that prevents leakage at the interface between the fluid channels 8154 and the interior channels 8150 or may include, in various embodiments, a sealing element such as a silicone sheet, an o-ring surrounding each fluid channel 8154 or the like. In some embodiments, the detachable manifold 8148 and/or the control unit 8052 may include one or more magnets 8156 that align to facilitate the connection between the detachable manifold 8148 and the control unit 8052 and that hold the detachable manifold 8148 in position with the gasket 8152. In some embodiments, only one of the detachable manifold 8148 and the control unit 8052 is provided with one or more magnets 8156, while the other of the detachable manifold 8148 and the control unit 8052 is provided with one or more metal features for attracting the one or more magnets 8156. For instance, in an embodiment where the detachable manifold 8148 includes one or more magnets 8156, the control unit 8052 may be provided with a metal face plate that forms at least a portion of the gasket 8152 for contacting the detachable manifold 8148. In other embodiments, the detachable manifold 8148 may be attached through other known fastening means such as a latch or the like. Additionally, in some embodiments, the detachable manifold 8148 may be connected to the control unit 8052 through a hinged connection that allows the detachable manifold 8148 to pivot relative to the gasket 8152 or a partial hinged connection that allows the detachable manifold 8148 to pivot relative to the gasket 8152 and to be fully detached from the control unit 8052 if desired. In some embodiments, the detachable manifold 8148 and the control unit 8052 may include one or more complimentary alignment features 8061 to aid with proper alignment of the interior channels 8150 and fluid channels 8154 when the detachable manifold 8148 is connected to the control unit 8052.

The pump 8048, shown in FIG. 19B, is connected to each fluid channel 8154 through a valve 8043, shown in FIG. 19C, and through the manifold 8044, shown in FIG. 19C, such that the control unit 8052 is able to control the pump 8048, shown in FIG. 19B and/or one or more valves 8043, shown in FIG. 19C, to supply air to one or more of the fluid channels 8154 and, therefore, to the connectors 26, shown in FIG. 3, through the interior channels 8150 of the detachable manifold 8148. Thus, when the detachable manifold 8148 is connected to the control unit 8052, the control unit 8052 may supply air to one or more bladders 28, shown in FIG. 3, to control actuation thereof. For example, in some embodiments, the control unit 8052 may control six actuators 24, shown in FIG. 3, however, in other embodiments, the control unit 8052 may control as many actuators 24, shown in FIG. 3 as desired.

The detachable manifold 8148 may advantageously be detached from the control unit 8052 to quickly deflate all bladders 28, shown in FIG. 3, connected thereto so that the dynamic support apparatus 10, shown in FIG. 3, may be removed from the user. This may be particularly advantageous in emergency situations or the like. Additionally, the control unit 8052 may also advantageously be detached from the detachable manifold 8148 and attached to a test and/or calibration unit (not shown) for the dynamic support apparatus 10, shown in FIG. 3. The detachable manifold 8148 may also advantageously allow the control unit 8052 to be easily detached from the dynamic support apparatus 10, shown in FIG. 3, for charging of the power supply 8059, shown in FIG. 19B, for example, on a wireless charging pad or the like. In some embodiments, the detachable manifold 8148 may be integral with a holster, such as a belt holster, for the control unit 8052. Integrating the detachable manifold 8148 into the holster may advantageously allow the connectors 26, shown in FIG. 3, to terminate in the holster, allowing the control unit 8052 to be attached thereto, making the pneumatic connections in the process.

In some embodiments, the control unit 8052 includes a detection means (not shown) for alerting the control unit 8052 as to whether or not the detachable manifold 8148 is attached thereto. For example, the detection means (not shown) may include, but is not limited to, a mechanical switch, an electrical circuit that is completed through contact of the detachable manifold 8148 and the control unit 8052, a Hall effect sensor or the like. In some embodiments, the detection means (not show) may also allow the control unit 8052 to automatically detect that it is connected to the test and/or calibration unit (not shown).

The control unit 8052 may be generally the size of a personal data assistant or smart phone and, in some embodiments, the control unit 8052 may advantageously control more than one dynamic support apparatus 10, shown in FIG. 3. In other embodiments, a user may wear a separate control unit 8052 for each dynamic support apparatus 10, shown in FIG. 3. In some embodiments, multiple control units 8052 may be used and may work cooperatively or independently from a common set of inputs.

Figure 77A:
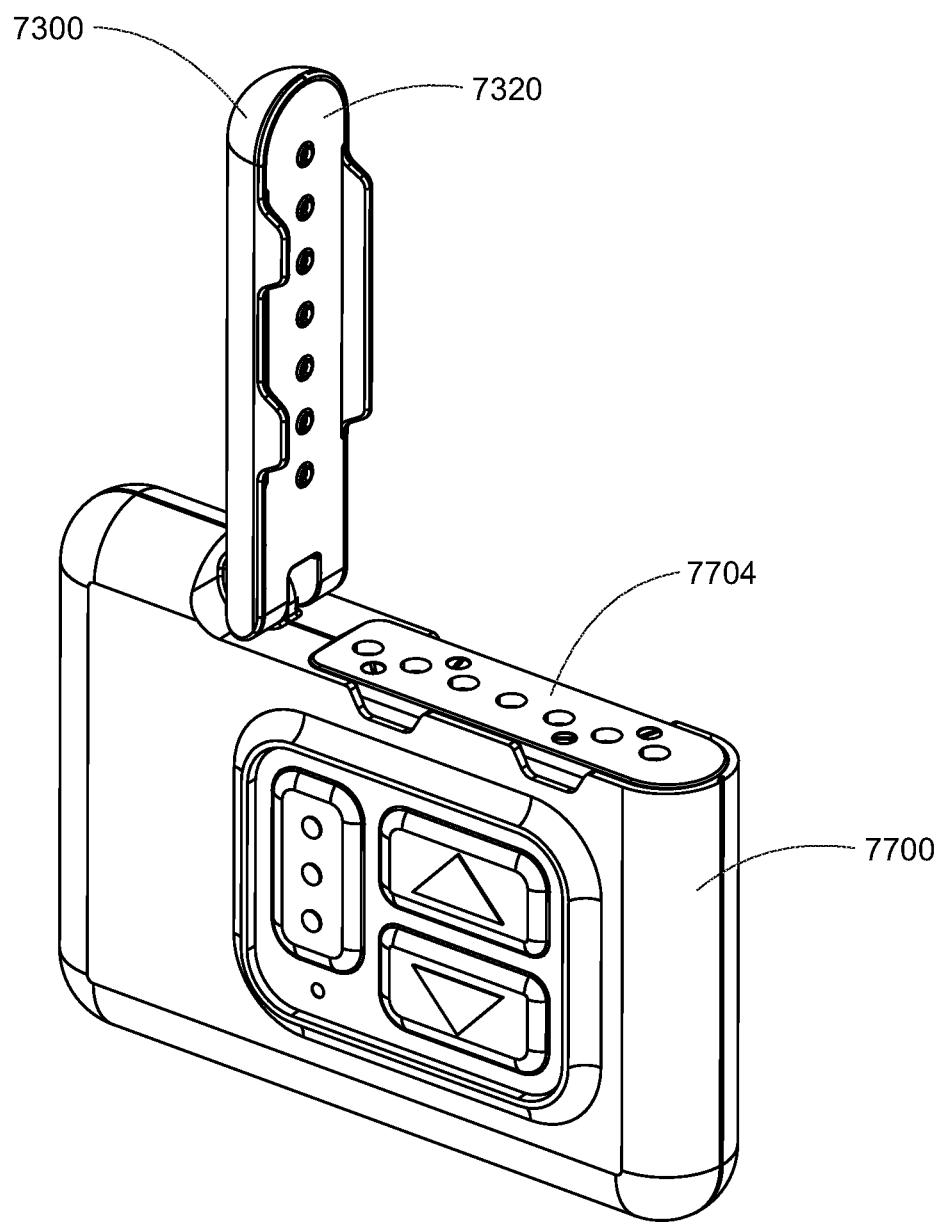
FIG. 77A shows an isometric partially exploded view of one embodiment of a control unit housing and detachable manifold.
Figure 77B:
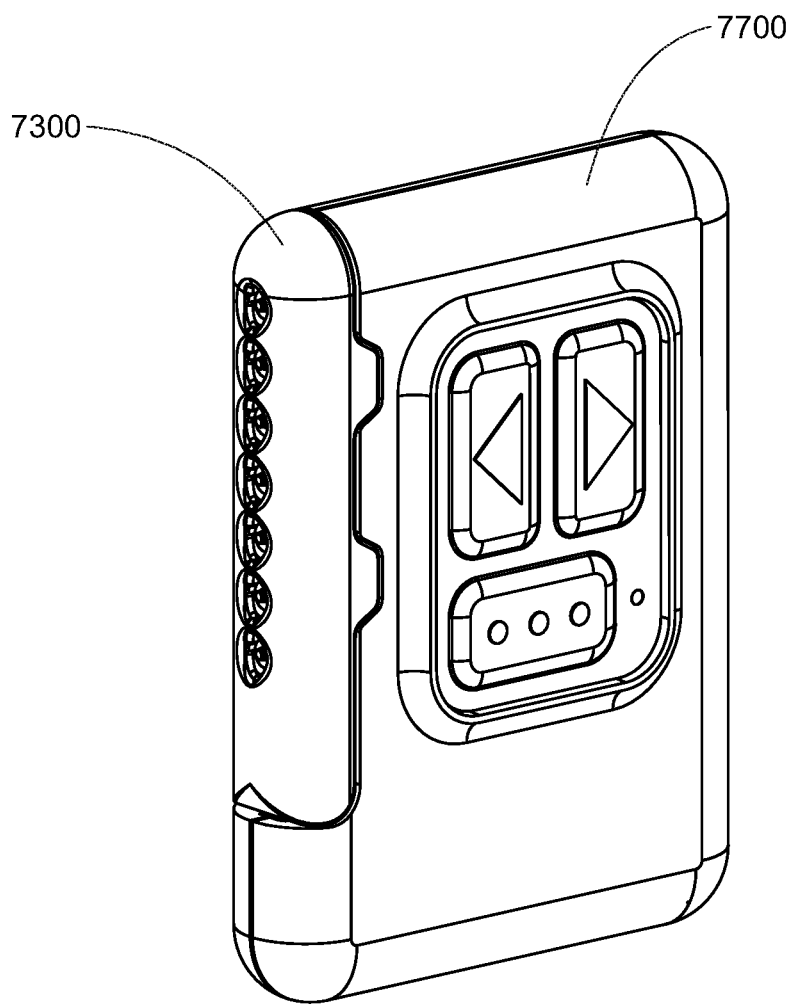
FIG. 77B shows a front view of one embodiment of a control unit housing and detachable manifold.

Referring now to FIGS. 73-76 another embodiment of a control unit detachable manifold 7326 is shown. In some embodiments, the control unit detachable manifold 7326 includes a detachable manifold cover 7300 having a plurality of interior channels 7308 and a plurality of fittings 7306 which fit within the interior channels 7308. The detachable manifold 7326 may include at least two magnets 7302, 7304 which, as described above, align to facilitate and/or guide the connection between the detachable manifold 7326 and the control unit 8052. In addition, in some embodiments, the control unit detachable manifold 7326 may include a plurality of block magnets which, in some embodiments, may include rows of block magnets 7316, 7318 that hold/maintain the detachable manifold 7326 in position with the gasket 8152. Referring now also to FIG. 77A, in some embodiments, the control unit 7700, includes one or more magnets of a mating polarity and arrangement or, as shown in the embodiment in FIG. 77A, a face plate 7704 of a suitable ferromagnetic material, for example, but not limited to, 416 stainless steel. Magnet backer plates 7312, 7314 may also be included in various embodiments and may increase the overall magnetic bond between the detachable manifold 7326 and the control unit 8052. In some embodiments, the magnet backer plates 7312, 7314 may be made from stainless steel, which includes, but is not limited to, 416 stainless steel, however, in various other embodiments, the magnetic backer plates 7312, 7314 may be made from any ferromagnetic material. The backer plates 7312, 7314 increase the strength of the magnetic connection between the detachable manifold 7326 and the control unit 8052 as they serve as flux shaping mechanisms. The detachable manifold 7326 may also include a manifold base 7320. In some embodiments, the geometries of the pneumatic interface may and are not limited to the ones shown and described herein.

Figure 73:
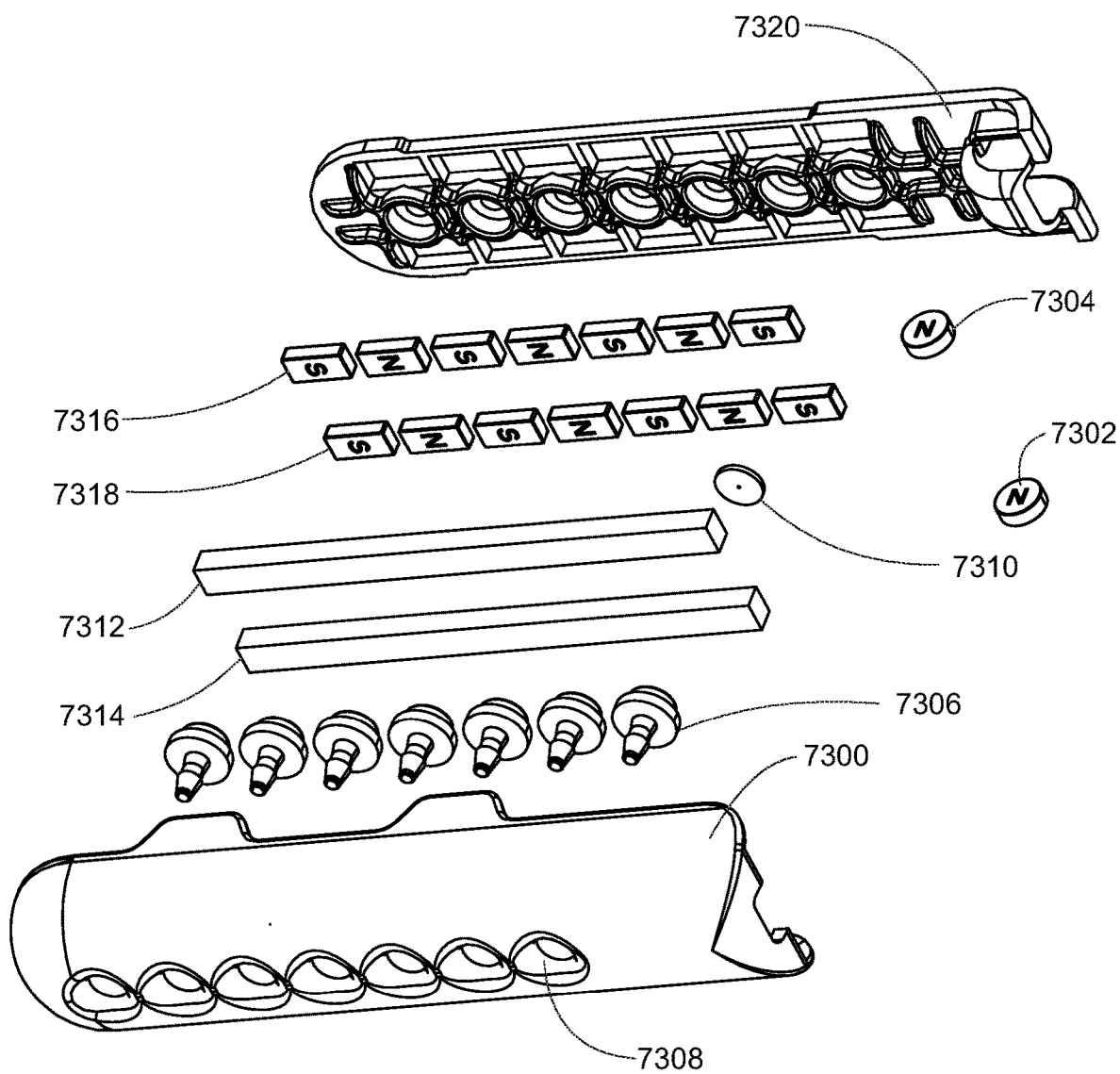
FIGS. 73-76 various embodiments of a control unit detachable manifold are shown.
Figure 74:
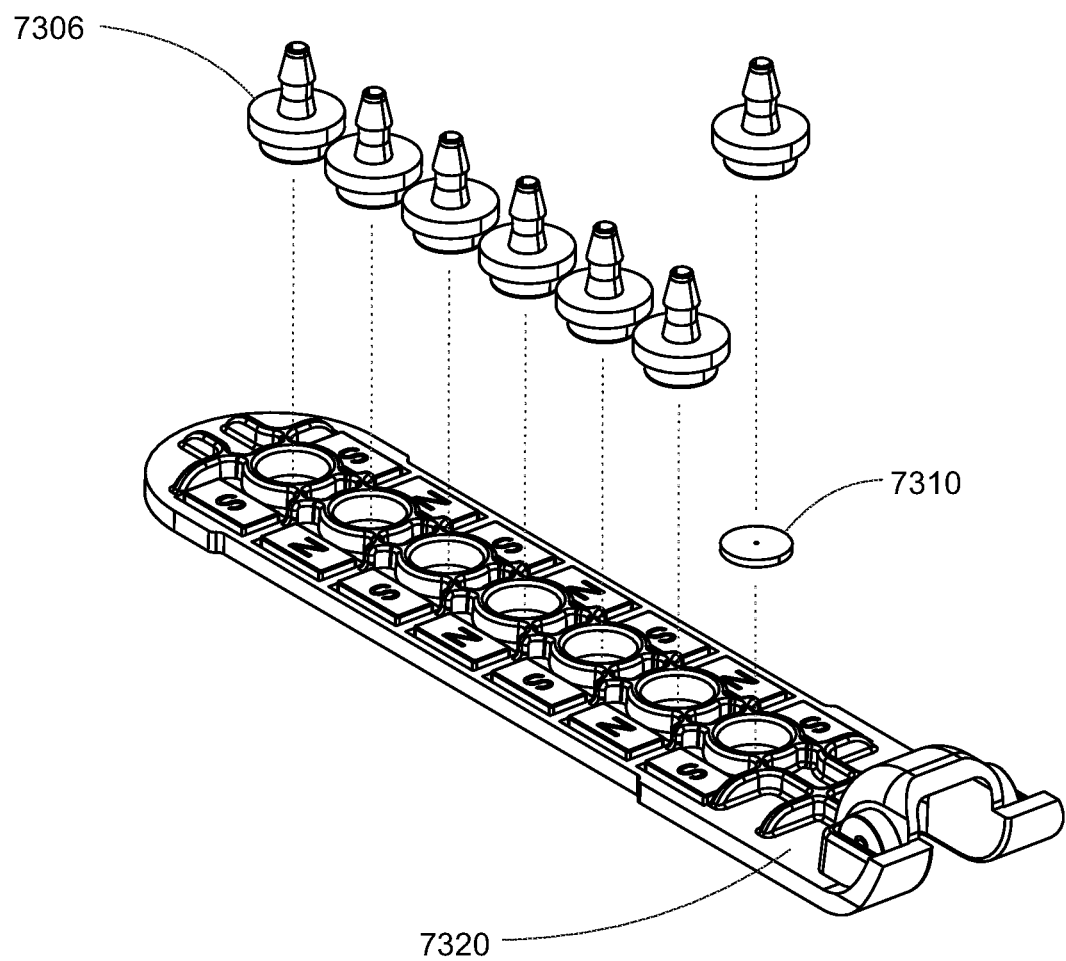
Figure 75:
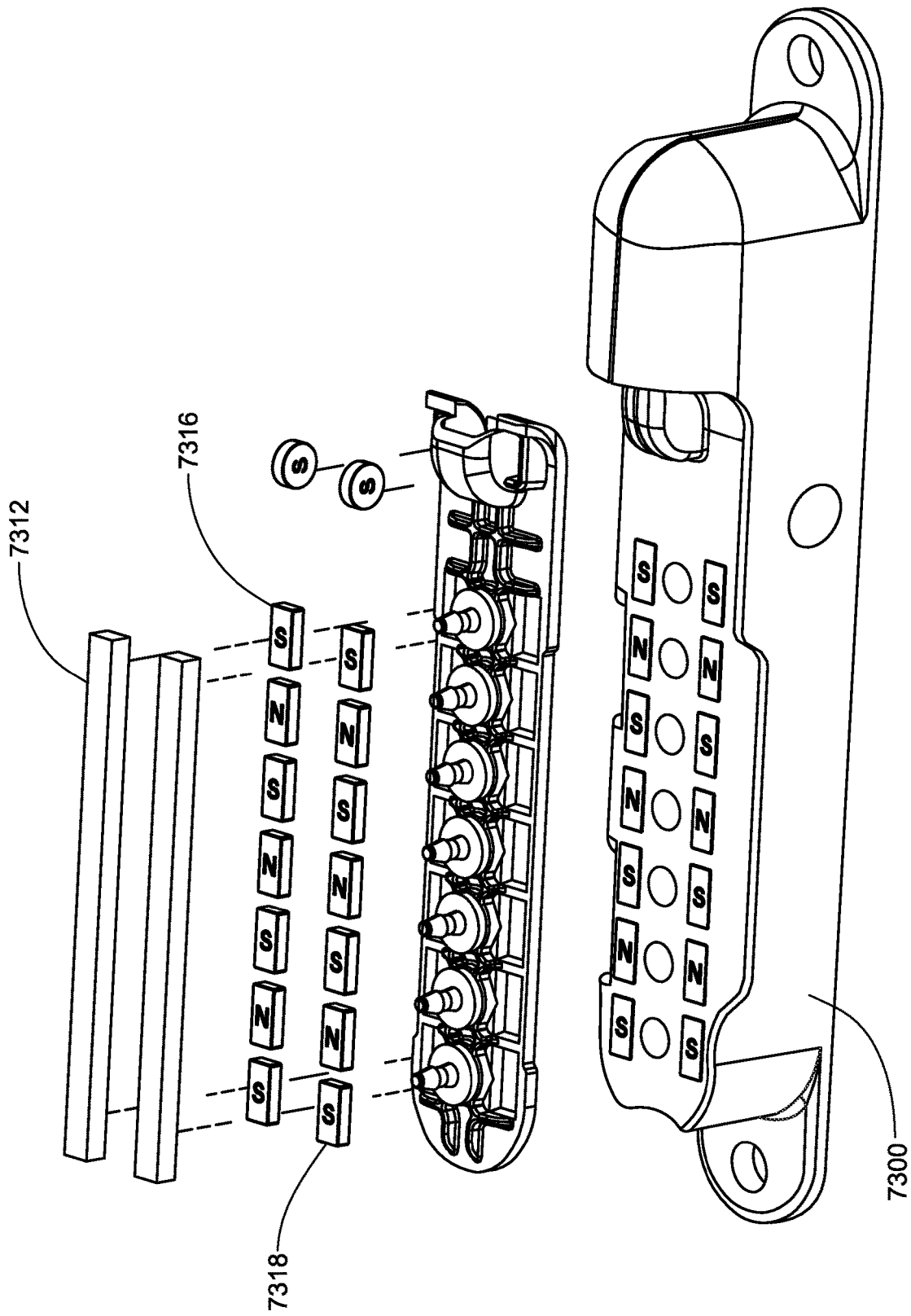
Figure 76:
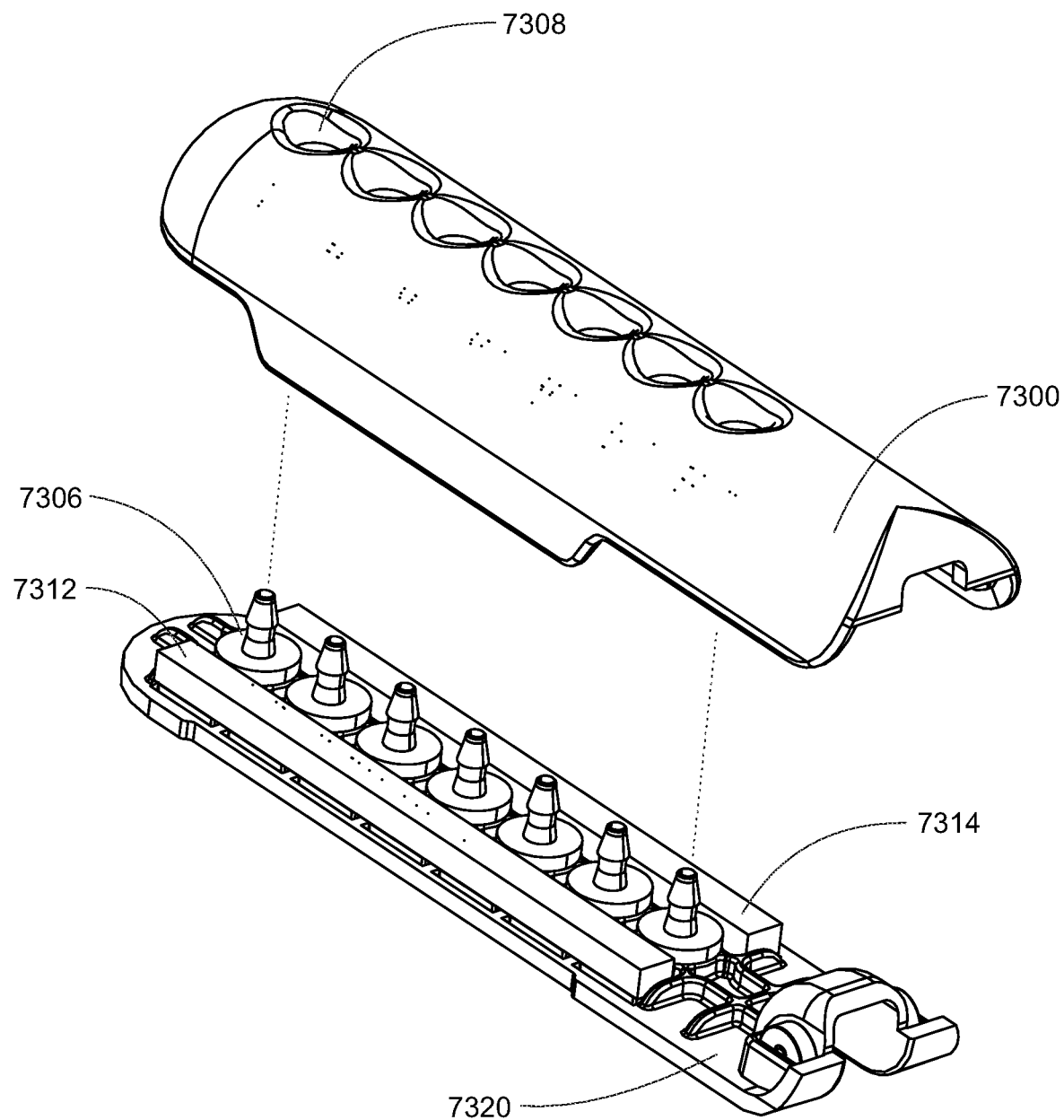

In some embodiments, the detachable manifold 7326 may include a flow restrictor, which, in some embodiments, may be a flow restrictor disc 7310, at the vent output, which is the output which vents air removed from the bladder. Although one flow restrictor disc 7310 is shown in FIG. 73, this is for illustrative purposes only, in various embodiments, a flow restrictor, whether a flow restrictor disc 7310 or another type of flow restrictor, may be included for each vent output from a bladder. In some embodiments, the flow restrictor 7310 may be a disc, as shown in FIGS. 73 and 74 and in some embodiments the disc 7310 may be made from plastic, which may include, but is not limited to DELRIN® or another polymer, including, but not limited to, a polyoxymethylene copolymer. However, in other embodiments, the disc 7310 may be made from any material including, but not limited to, stainless steel, brass and/or sapphire. In some embodiments, the flow restrictor may be disc shaped, however, in other embodiments; the flow restrictor may be any shape. In some embodiments, the flow restrictor includes an orifice, and in some embodiments, the orifice may be about 0.007 inches in diameter, however, in various other embodiments, the flow restrictor orifice may be larger or smaller than 0.007 inches in diameter. In some embodiments, a flow restrictor is used to slow the exit of air from the bladders such that the rate of loss of air may be more closely controlled. In addition, in some embodiments the flow restrictor may mitigate the rate of loss of air from the bladders during a software or controls failure. Also, because the vent port of the dynamic socket itself does not include a flow restrictor, to speed the rate of loss of air from the bladders, the detachable manifold 7326 may be disconnected from the control unit to remove the flow restrictor.

In some embodiments, the flow restrictor may be made from a porous membrane. In some embodiments, the flow restrictor may be made from a plug or sintered metal, which may be porous and used as a flow restrictor. In other embodiments, the flow restrictor may be any type of flow restrictor made of any material.

Referring now also to FIGS. 77E-77H, various views of one embodiment of a control unit housing 7700 are shown. In some embodiments, the control unit housing 7700 may include at least one vent 7702 which, in some embodiments, may include at least one opening in the control unit housing 7700 and in some embodiments, may include a porous membrane over the opening which may be used to prevent water ingress while allowing air into the control unit housing 7700 which is desirable for pump aspiration. Although one shape of the vent 7702 is shown in FIGS. 77E-77H, in various other embodiments, the vent may be shaped differently and may include one or more openings.

The control system 18, shown in FIG. 1, may be an active control system that provides real-time adjustments in each actuator 24, shown in FIG. 3, to accommodate prosthetic load and user posture and to anticipate user needs (and, in other embodiments where the dynamic support system is used for other purposes, the adjustments may accommodate user preference and/or needs). For example, with the exemplary embodiment having bladders 28, shown in FIG. 3, as actuators 24, shown in FIG. 3, the control unit 8052 may include an active control system with various control modes for activating the inflation/deflation of the bladders 28, shown in FIG. 3, as will be discussed in greater detail below. The active control system may be in place of, or in addition to, the manual pump control discussed herein. The active control system 18 may have one or more input mechanisms for gathering readings on the stability and fit of the support apparatus 10, shown in FIG. 1, with the residuum 12, shown in FIG. 1.

Figure 22:
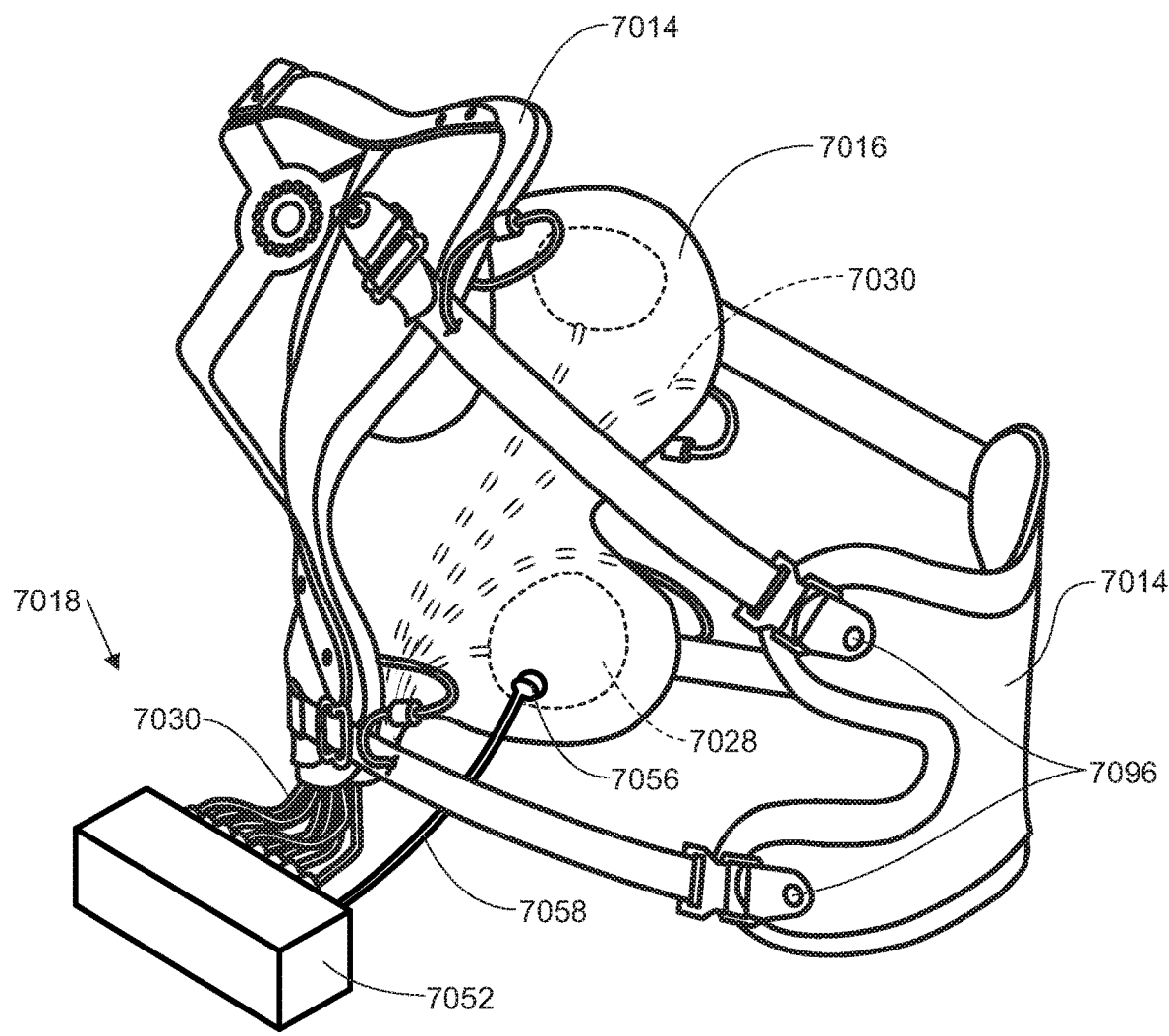
FIG. 22 is a perspective view of one embodiment of a dynamic support apparatus representative of a shoulder disarticulated configuration.

In some embodiments, the input mechanism includes sensors, such as pressure transducers. The sensors may be placed on the inner shell of the frame, on the actuator(s), on the connector(s) connected to the actuator(s), or in any other suitable location, for providing information on the stability and fit of the support apparatus, as should be obvious to those skilled in the art. Controlled by a computer or processor, the sensor(s) determine the pressure in the actuator(s) and, with the feedback loops, signals are sent to the control unit to either increase or decrease the actuator's pressure, possibly by inflation or deflation, thereby changing the volume of the actuator to exert the needed force to maintain the support apparatus's secure fit with the user's body. The computer or processor for controlling the sensors is preferably integrated into the control unit 8052 of the control system 18, shown in FIG. 1, as discussed above. Referring to FIG. 22, with the exemplary embodiment having bladders 7028 as actuators 7024, a pressure sensor 7056 may be placed on the bladder 7028 to provide fit information to the control unit 7052 through a sensor connector 7058. In this embodiment, if a loose fit is detected by pressure sensor 7056, i.e. the sensed pressure is low, a signal is sent to the control unit 7052 to increase the pressure in the corresponding bladder 7028 until a high pressure is sensed and therefore a stable condition is achieved. In this embodiment, the active control system adjusts the pressure of each actuator 7024 in response to the part of the morphing residuum in contact with that actuator. This embodiment does not necessarily maintain a constant fluid pressure in each bladder 7028 nor does it necessarily maintain a total constant contact pressure against the residuum. In addition to pressure sensors for each actuator 24, shown in FIG. 3, or actuator channel, in some embodiments, the control unit 8052 may also include one or more pressure sensors detecting pressure within the manifold 8044, shown in FIG. 19C, which advantageously allows the control unit 8052 to check one pressure measurement against another, if desired. This manifold pressure sensor is also advantageous when increasing the pressure in a particular actuator 24, shown in FIG. 3, or actuator channel. For example, the manifold pressure sensor allows the control unit 8052 to first activate the pump 8048, shown in FIG. 19B, to bring the pressure within the manifold 8044, shown in FIG. 19C, to that which may be desired within the actuator 24, shown in FIG. 3. Once the desired pressure is achieved, the control unit 8052 may then open the valve 8043, shown in FIG. 19C, connected to the actuator 24, shown in FIG. 3, to increase the pressure within the actuator 24, shown in FIG. 3, without causing a momentary drop in pressure when the valve 8043, shown in FIG. 19C, is opened to connect the actuator channel to the manifold 8044, shown in FIG. 19C.

An alternative embodiment includes an active control system with sensors 7056 and feedback loops that maintain constant pressure in each actuator 7024. For example, in an embodiment having bladders 7028, the sensors 7056 and feedback loops may be placed on each bladder 7028 or on each fluid path 7030 of each bladder 7028. The sensors 7056 may be programmed to take an initial pressure reading of a bladder 7028. The sensors 7056 then may take continuous pressure readings of the bladder 7028, comparing these readings to the initial pressure. As the bladder pressure changes, the sensors 7056 and feedback loops may send signals to the control unit 7052, which may adjust the pressure in the bladder 7028 to maintain the initial bladder pressure. Maintaining a constant pressure in the bladders 7028 may correspond to maintaining a constant fit between the support apparatus and the residuum.

Figure 23:
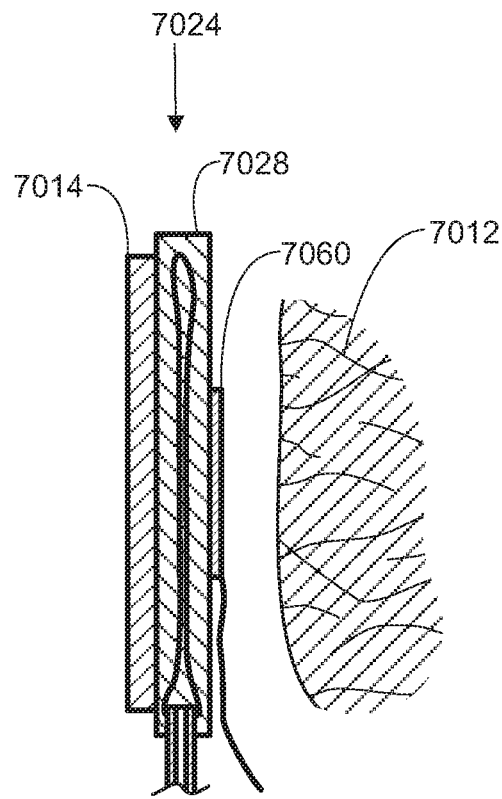
FIG. 23 is a cross-sectional view of an un-actuated actuator and sensor unit.
Figure 24:
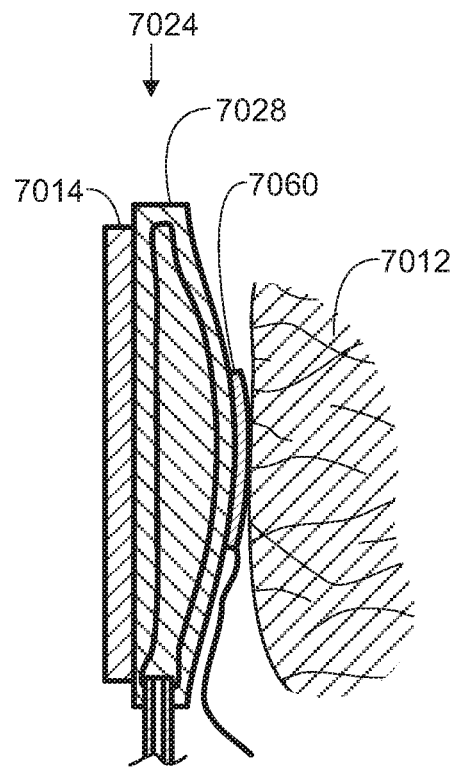
FIG. 24 is the cross-sectional view of FIG. 23 with the actuator actuated.

Referring to FIGS. 23 and 24, the active control system may also include EMG electrodes 7060 for providing control input to the control unit 7052. The EMG electrodes 7060 may be placed between the actuator(s) 7024 and the skin of the residuum 7012, on a separate layer or on each actuator 7024. The EMG electrodes 7060 sense voluntary underlying muscle activity and may be used to control some function of the prosthesis. In a support apparatus having bladders 7028, the bladders 7028 control the downward pressure of the EMG electrodes 7060 on the skin of the residuum 7012. This control of the downward force may eliminate unintentional relative movement of the EMG electrodes 7060, which generates an artifact signal, which may be present with EMG electrodes. As the residuum 7012 morphs or the patient puts loads on the residuum 7012, the pressure applied to each bladder 7028 by the residuum 7012 may vary, which in turn may vary the EMG electrodes' contact with the skin of the residuum 7012. The pressure sensors sense this pressure differential, and the control unit may adjust the pressure of the bladder(s) 7028 so as to put pressure back on the EMG electrodes 7060. This pressure on the EMG electrodes 7060 pushes the EMG electrodes 7060 against the skin of the residuum 7012, which may enhance the maintenance of constant contact and a secure fit between the residuum and the support apparatus.

The control unit may include a partially-automatic control system for the actuator(s) 24 with preset actuator pressures. The user has a control unit 52 that may be programmed with preset numbers or modes that correspond to preset actuator pressures. These presets may be programmed by the patient while using the support apparatus 10 or may be pre-programmed by a clinician. The preset pressures may be set to accommodate support apparatus fits for a resting mode, a light load mode, a high load mode, a massage mode, or other types of activity. Depending on the patient's activity, the patient may select a number or mode on the control unit 52, which may automatically adjust the fit and pressure of the actuator(s) 24 to whatever pressure(s) was programmed to that number. The massage mode may be utilized to facilitate circulation in the residuum. For example, the control unit may turn off one actuator 24 at a time to allow blood flow into the region of the turned off actuator 24. By cycling through the actuators one at a time, blood flow in the residuum 12 is assisted, with minimal loss of stability of the dynamic support apparatus 10.

The temperature control mechanism 19 of the dynamic support apparatus 10 may include the apertures 20 of the support apparatus 10 in FIG. 2. The apertures 20 allow for cooling by passive ventilation, which reduces moisture and heat between the support apparatus 10 and the residuum 12. Additionally, the temperature control mechanism 19 may include ducted air flow over the skin of the residuum 12, heat exchangers, personal cooling systems (such as those found in Sharper Image's "Personal Cooling System"), ducted fans, or integrating sports or outdoor recreation clothing designed for heat/moisture management. The temperature control mechanism 19 may be placed in a separate layer between the dynamic interface 16 or top surface 22 and the residuum 12, integrated into the same layer as the dynamic interface 16, or integrated into the top surface 22 of the frame 14. An active control system, similar to the system already described, may also be used to control the temperature control mechanism 19 so as to maintain a constant temperature, through the use of temperature sensors, between the residuum 12 and the support apparatus 10.

Figure 25:
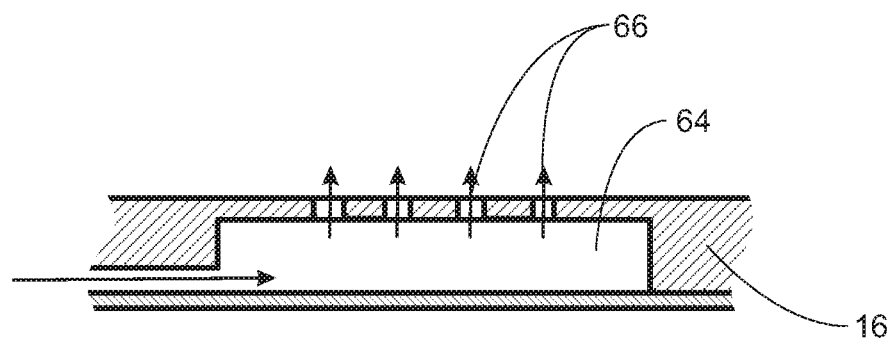
FIG. 25 is a cross-sectional view of one embodiment of a temperature control system of a dynamic support apparatus.

Referring to FIG. 25, the temperature control mechanism 19 may include one or more duct(s) 64 connected to a plurality of orifices 66 and integrated into the dynamic interface 16. In this embodiment, temperature control is accomplished by supplying air through the duct(s) 64 and the plurality of orifices 66 to impinge on the skin of the residuum.

Figure 26:
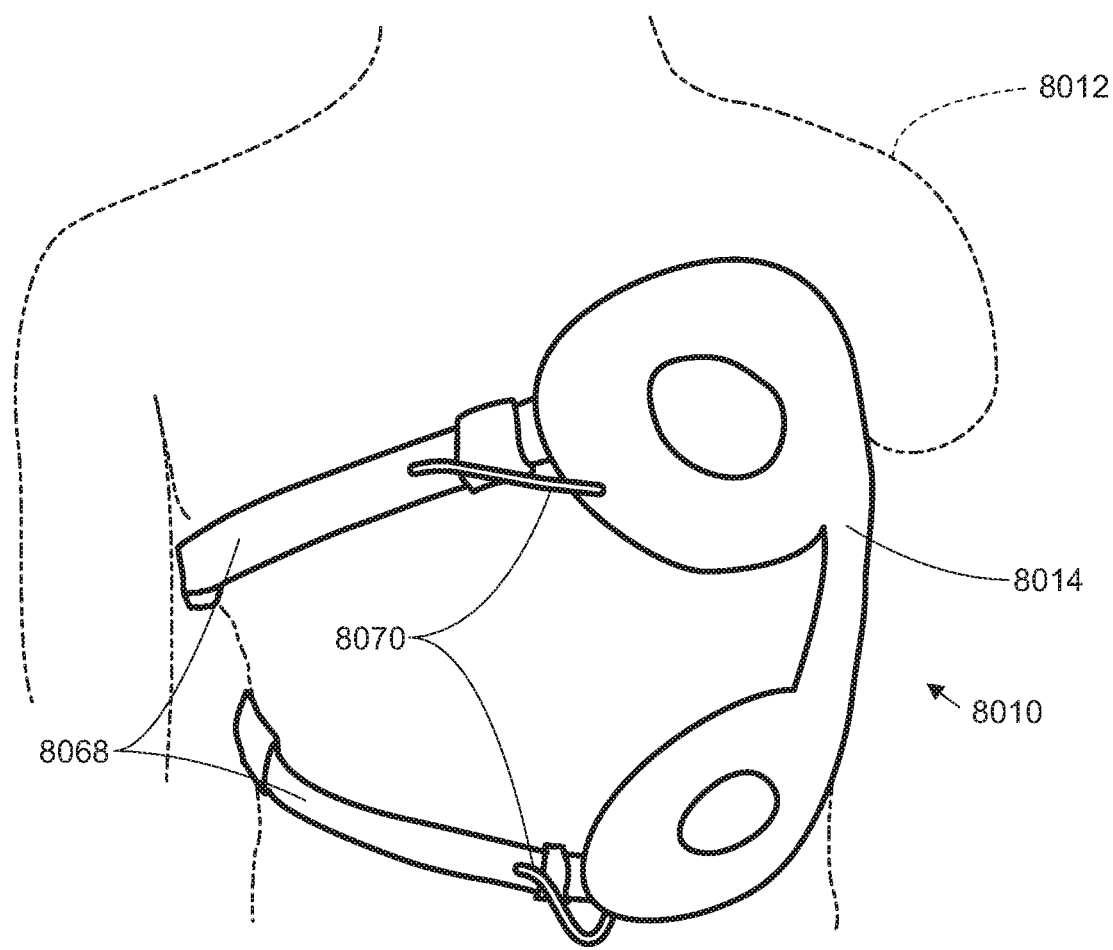
FIG. 26 is a front view of an alternative embodiment of a dynamic support apparatus as it is worn around the body.
Figure 27:
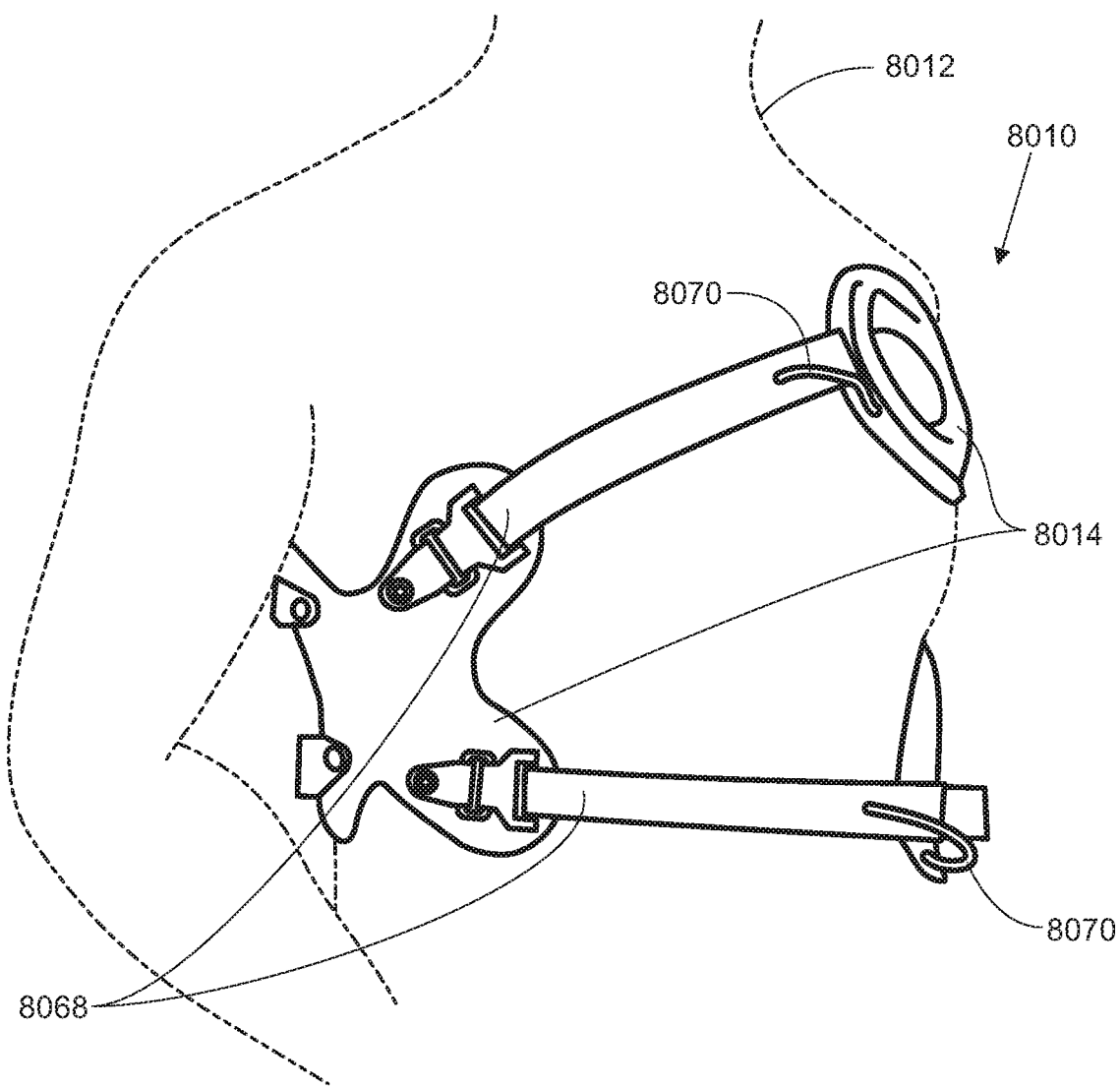
FIG. 27 is a side view of the dynamic support apparatus of FIG. 26.
Figure 28:
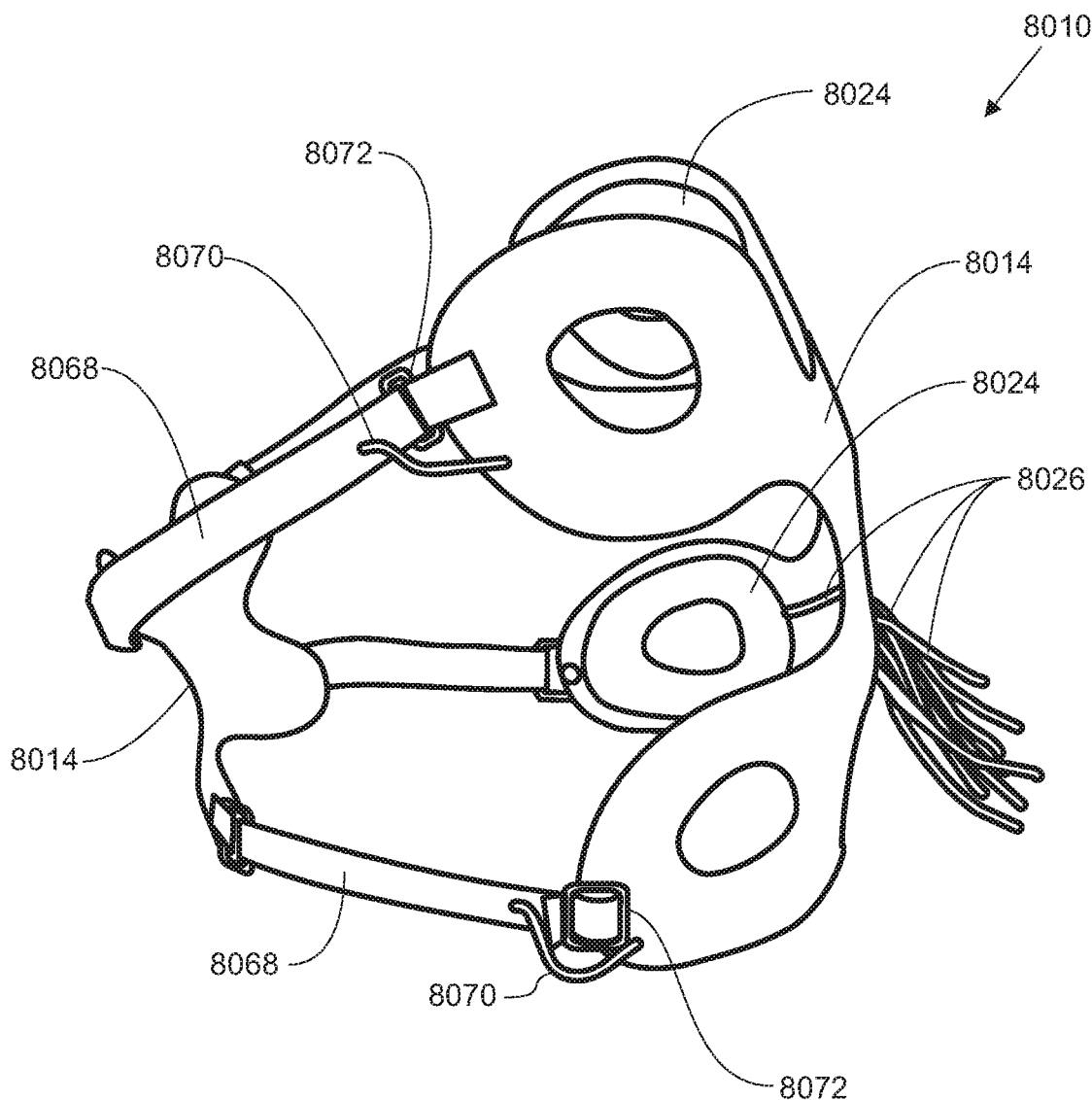
FIG. 28 is a structural view of the dynamic support apparatus of FIGS. 26 and 27.

While the exemplary embodiment described above relates to upper-limb prosthesis for TH amputees, the support apparatus can be used for transradial (TR) amputees and for shoulder disarticulation (SD) amputees. Referring now to FIGS. 26-28, one embodiment of a dynamic support apparatus 8010 for SD amputees includes a frame 8014, having actuators 8024 and connectors 8026, connected to one or more active straps 8068, such as McKibben artificial muscles. The term dynamic strap, as used herein is synonymous with the active strap 8068. Each active strap 8068 contains at least one actuator and at least one strap connector 8070 for connecting the actuator to the control system. Similar to those embodiments already described, each active strap 8068 may also contain sensors and feedback loops for providing fit information to the control system. The active straps are connected to the control system and control unit. Thus, as pressure and tension on the active strap(s) 8068 change due to load variations on the residuum 8012, the sensors signal the control unit to adjust the pressure of the strap(s)'s actuator(s), which in turn adjusts the tension and length of the strap. These adjustments ensure a secure fit against the user's body and ensure stability of the prosthesis. The active straps 8068 and strap connectors 8070 may be integrated with the dynamic interface 8016, such that one control system controls both the dynamic interface 8016 and the active straps 8068 simultaneously. As should be understood by those skilled in the art, the strap connectors 8070 may alternatively be routed to a separate control unit specifically for the active straps 8068.

Referring to FIG. 28, in addition to controlling the tension and length of active straps 8068 by actuators, each active strap 8068 may additionally contain a length adjuster 8072, which may be used to manually adjust the length and fit of each active strap 8068.

Referring to FIGS. 29 and 30, in the exemplary embodiment having bladders 8028 for actuators 8024 and fluid path connectors 8030 for strap connectors 8070, the bladder 8028 is encased in a deformable strap material 8074, such as nylon webbing. The bladder 8028 is connected to the control system by the fluid path connector 8030. The end of each active strap 8068 has an attachment mechanism 8076 for attaching the active strap 8068 to the frame. The active strap 8068 is in a preset condition in FIGS. 29 and 30, having a strap length 8078 and a preset bladder cross-section.

Referring to FIGS. 31 and 32, the active strap 8068 is in an actuated condition having an actuated bladder cross section greater than that shown in FIG. 30 and an actuated strap length 8080 that is less than the preset strap length shown in FIG. 29. Accordingly, when instability is detected in the support apparatus, either by the control system or by the user, pressure may be increased in the active strap 8068, causing the bladder 8028 to expand radially from the preset condition of FIGS. 29 and 30 to the actuated condition of FIGS. 31 and 32. As pressure increases in the bladder 8028, the deformable strap material 8074 deforms, decreasing the length of the active strap 8068 and increasing stability in the support apparatus.

Referring to FIG. 33, the control system 8018 of each active strap 8068 may be an electric pump 8048, such that the pressure in each active strap 8068 may be adjusted independent of the other active straps 8068 and the dynamic interface. Referring to FIG. 34, the control system 8018 of each active strap 8068 may alternatively be a pressure bulb 8042, such that the pressure in each active strap 8068 may be adjusted independent of the other active straps 8068 and the dynamic interface. Although shown as separate units in FIGS. 33 and 34, the control system 8018 may be integrated with the bladder 8028 similar to that shown in FIGS. 20 and 21.

Unlike typical McKibben artificial muscles, which are used in high-pressure applications, the active straps 8068 in the dynamic support apparatus 8010 are operated under low-pressure conditions. Accordingly, various configuration changes have been made to the inflation, arrangement and strap characteristics of the active straps 8068 to increase performance and efficiency in low-pressure conditions. The actuator length to strap length for the active strap 8068 is about two-thirds the length seen in the prior art. This increases actuation with less pressure, and makes the active strap 8068 and the support apparatus more responsive. Additionally, when the actuator in active strap 8068 is a bladder 8028, it may be fabricated wider than the strap itself so that the bladder 8028 can be inflated, causing the strap diameter to increase, without putting energy into stretching the bladder 8028 itself. Bladders that are fabricated by laser welding, such as the bladder 28 shown in FIG. 15, also provide for improved performance in low-pressure conditions because they can be constructed to deform the active strap 8068 in specific shapes and locations, rather than only circular deformation.

Figure 50:
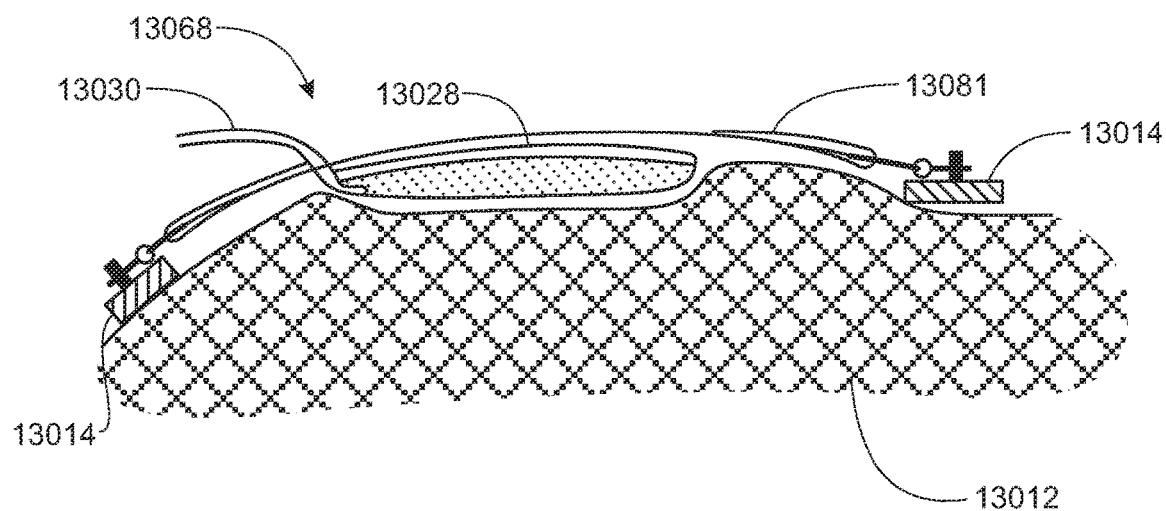
FIG. 50 is an illustrative view of a strap according to one embodiment.
Figure 51:
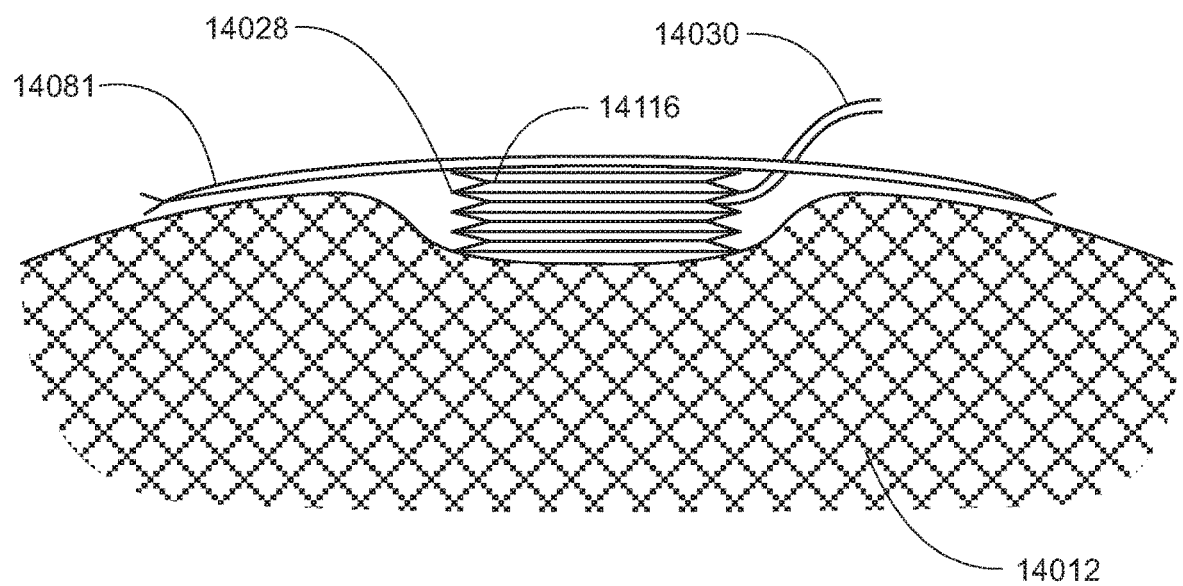
FIG. 51 is an illustrative view of a strap according to one embodiment.

Referring to FIG. 50, an additional embodiment of an active strap 13068 is shown. The active strap 13068 may include a flexible strap portion 13081 having a bladder 13028 attached thereto. The active strap 13068 is connected to the frame 13014 to secure the frame to the user's residuum 13012. For example, the active strap 13068 may secure a trans-radial prosthetic support to the user's elbow. The bladder 13028 is operatively connected to the control system 18, shown in FIG. 1, through a fluid path connector 13030. In operation, the active strap 13068 secures the frame 13014 to the residuum 13012, with the flexible strap portion 13081 providing the active strap 13068 with strong tensile preload. The bladder 13028 of the active strap 13068 may then be actuated while the frame is secured to the residuum 13012 to generate a normal force on the residuum 13012 to alter the securing properties of the active strap 13068. Thus, the bladder 13028 allows for remote adjustment of the fit of the support apparatus 10, shown in FIG. 1. The bladder 13028 also provides the active strap 13068 with a measure of compliance and may aid in anchoring the frame 13014 to the residuum, i.e., to prevent sliding. Although the bladder 13028 is shown in a particular embodiment for exemplary purposes, it should be understood that the bladder 13028 may be in the form of any of the various embodiments described herein. For example, as seen in FIG. 51, the bladder 14028 may include an accordion sidewall 14116 to allow for increased actuation.

Figure 35:
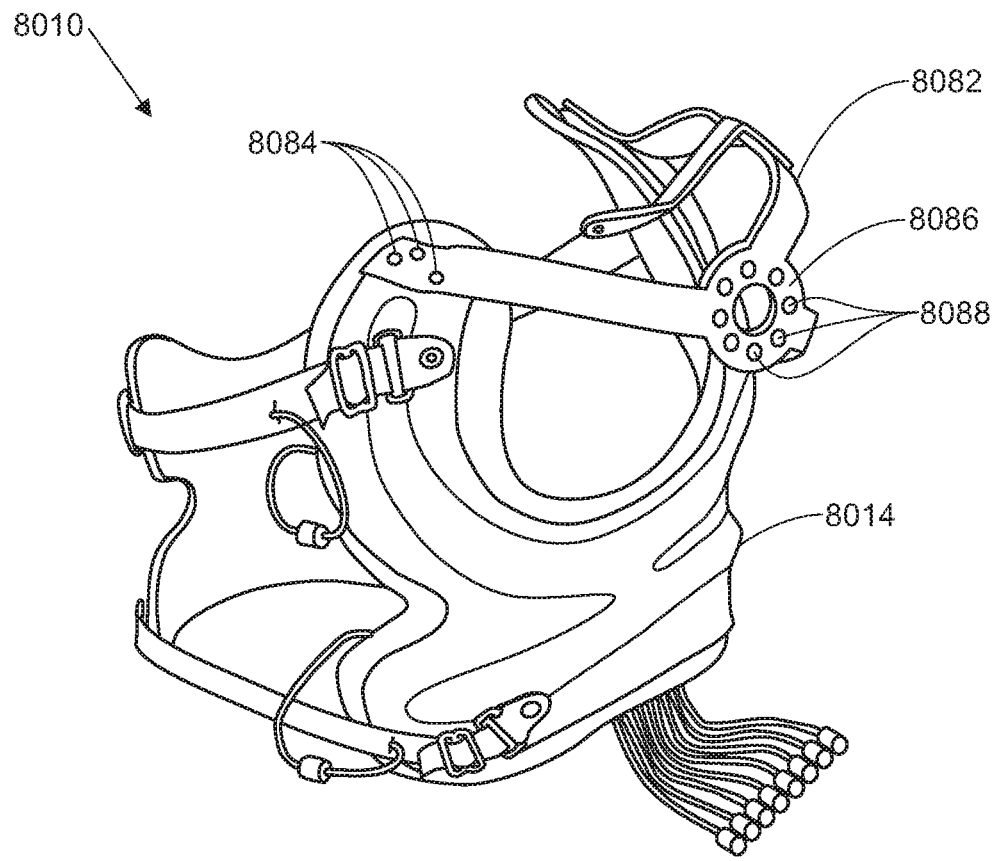
FIG. 35 is a front perspective view of one embodiment of a dynamic support apparatus showing a prosthetic interface.
Figure 36:
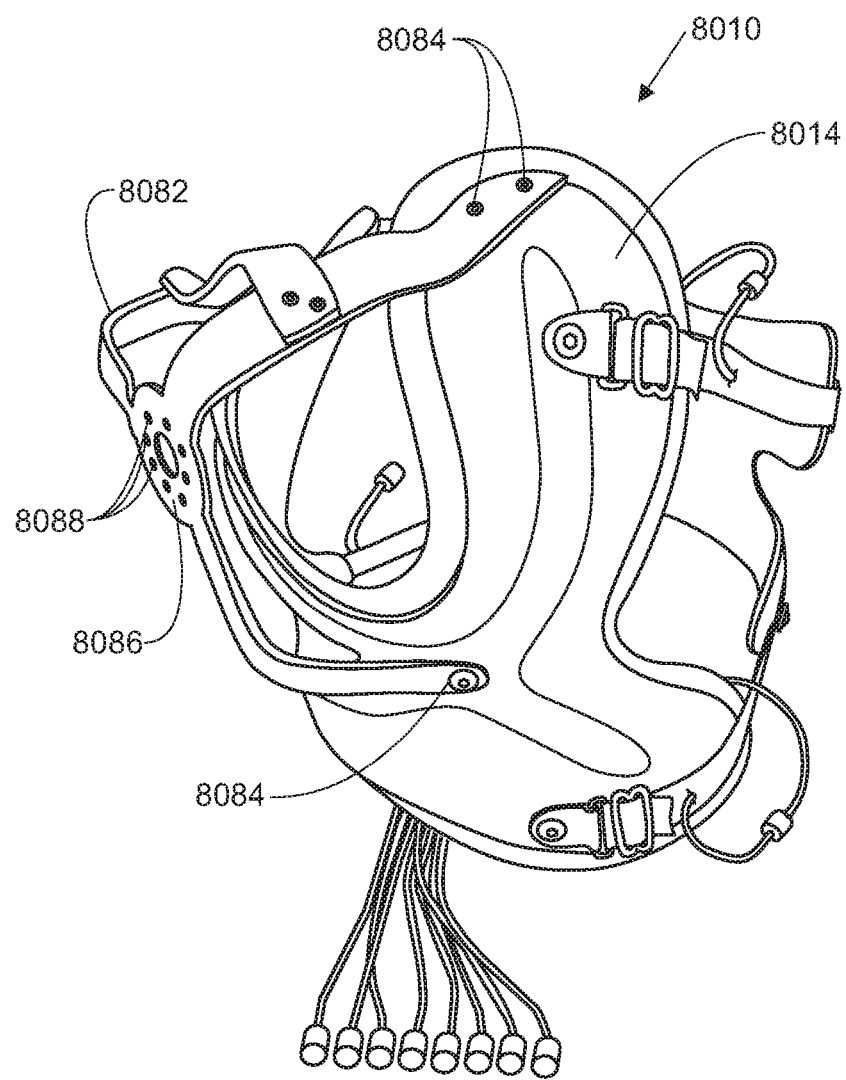
FIG. 36 is a rear perspective view of the dynamic support apparatus of FIG. 35.
Figure 37:
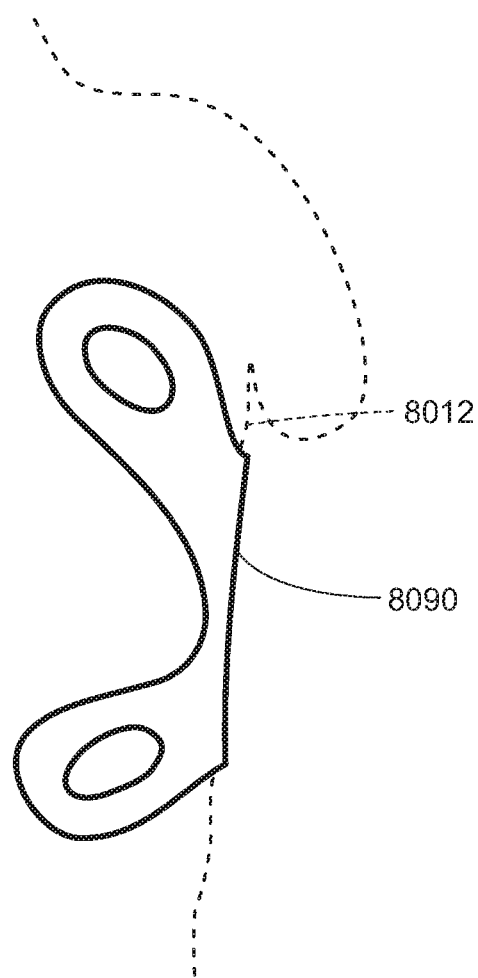
FIG. 37 is an illustration of a portion of one technique for fabricating and embodiment of a dynamic interface for a dynamic support apparatus.
Figure 38:
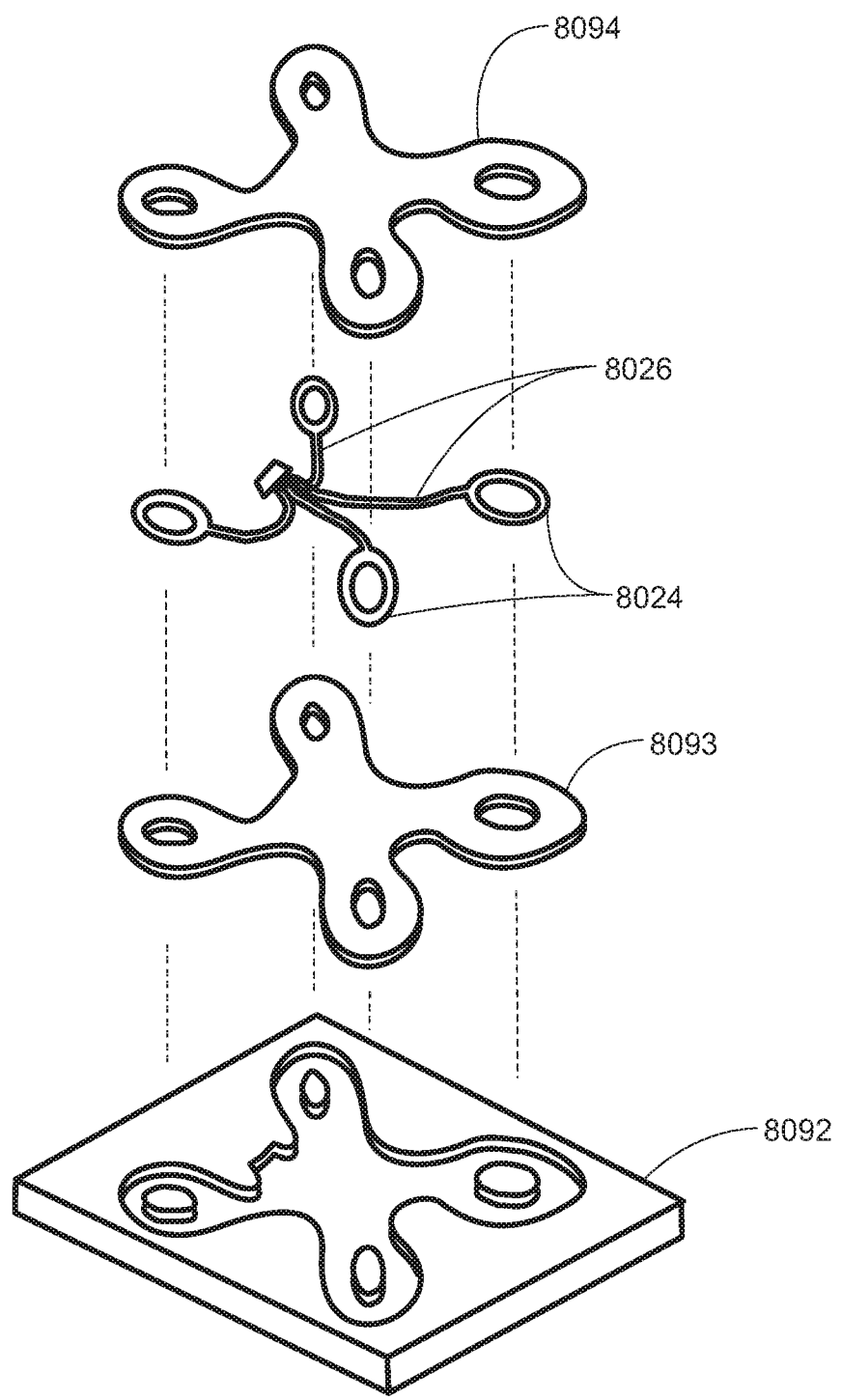
FIG. 38 is an illustration of a portion of the technique for fabricating and embodiment of a dynamic interface for a dynamic support apparatus.
Figure 39:
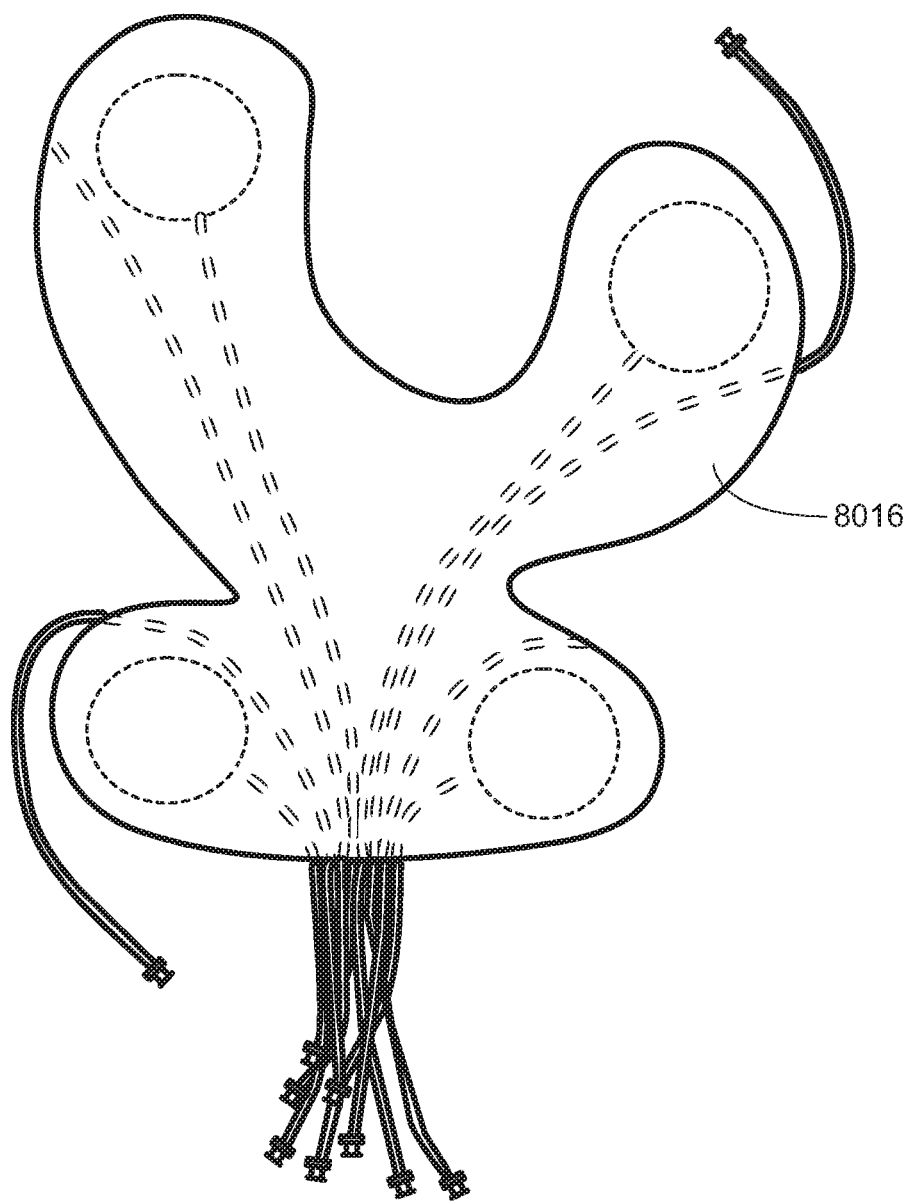
FIG. 39 is a front view of the dynamic interface fabricated from the technique of FIGS. 37 and 38.
Figure 40:
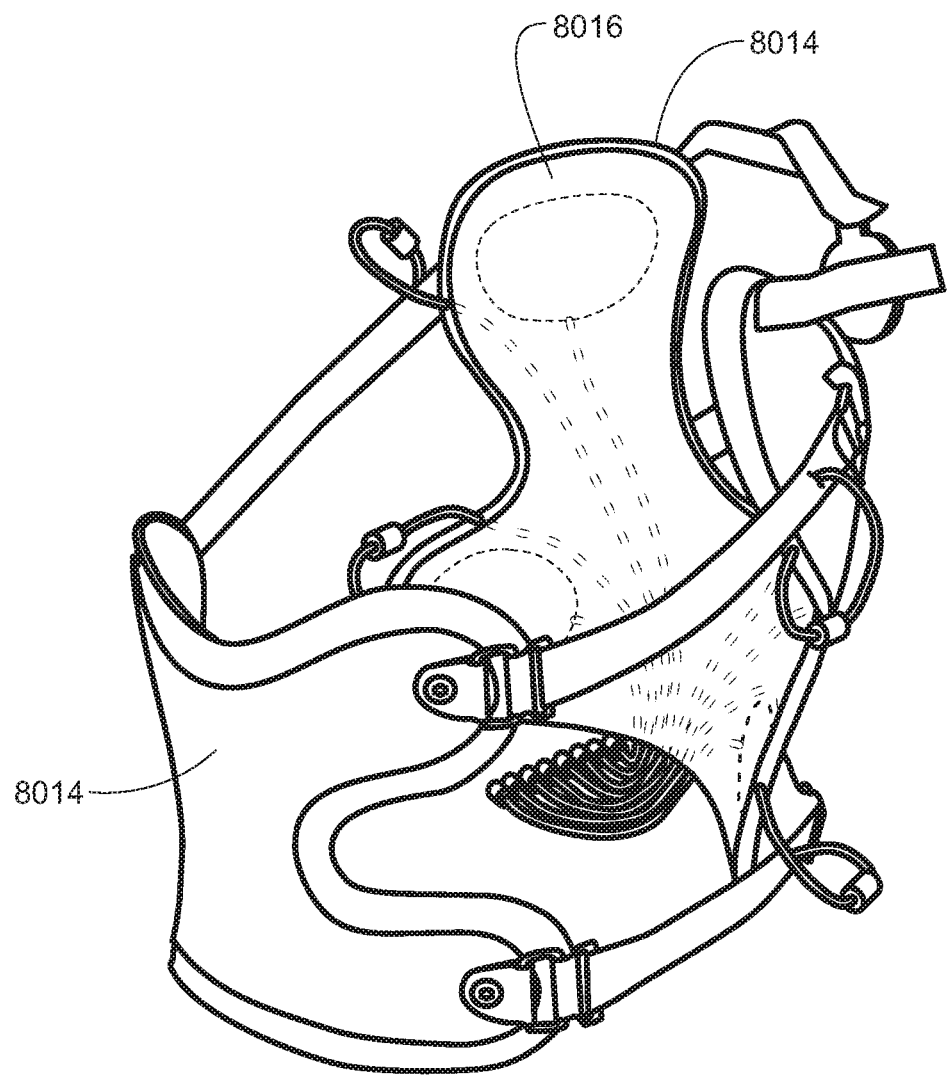
FIG. 40 is a front perspective view of the dynamic support apparatus of FIGS. 37-39.
Figure 41:
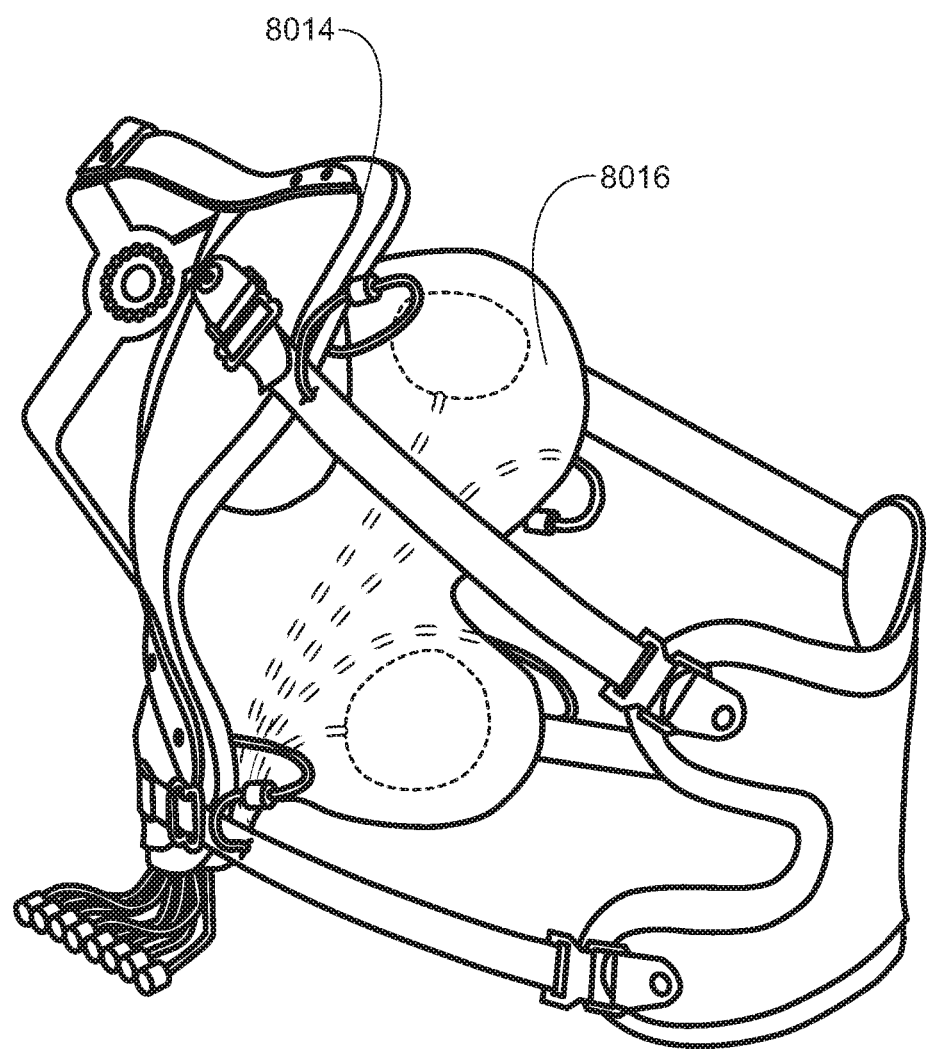
FIG. 41 is a rear perspective view of the dynamic support apparatus of FIGS. 37-39.
Figure 42:
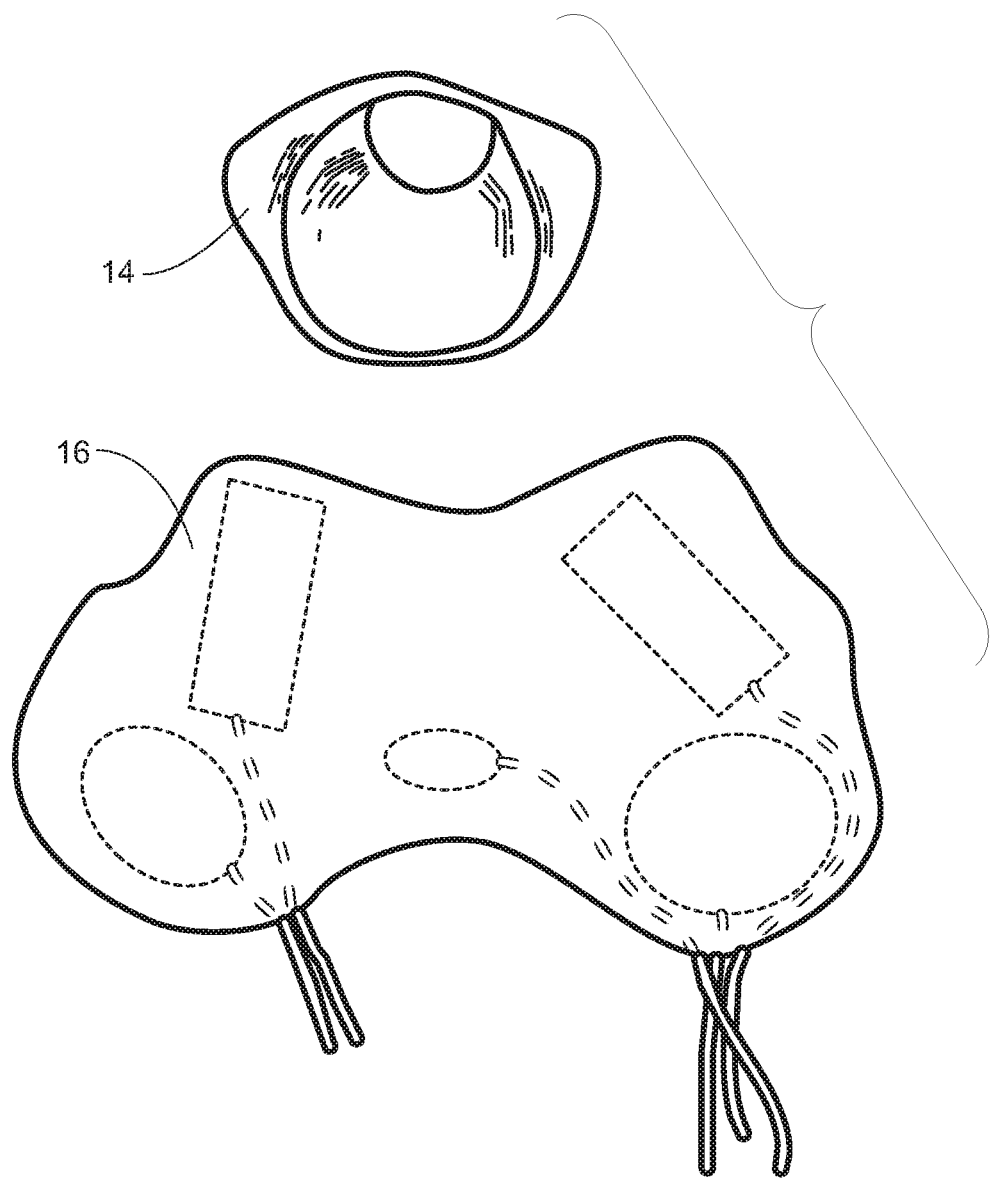
FIG. 42 is a front view of an alternative embodiment of a dynamic interface fabricated from the technique of FIGS. 37 and 38.
Figure 43:
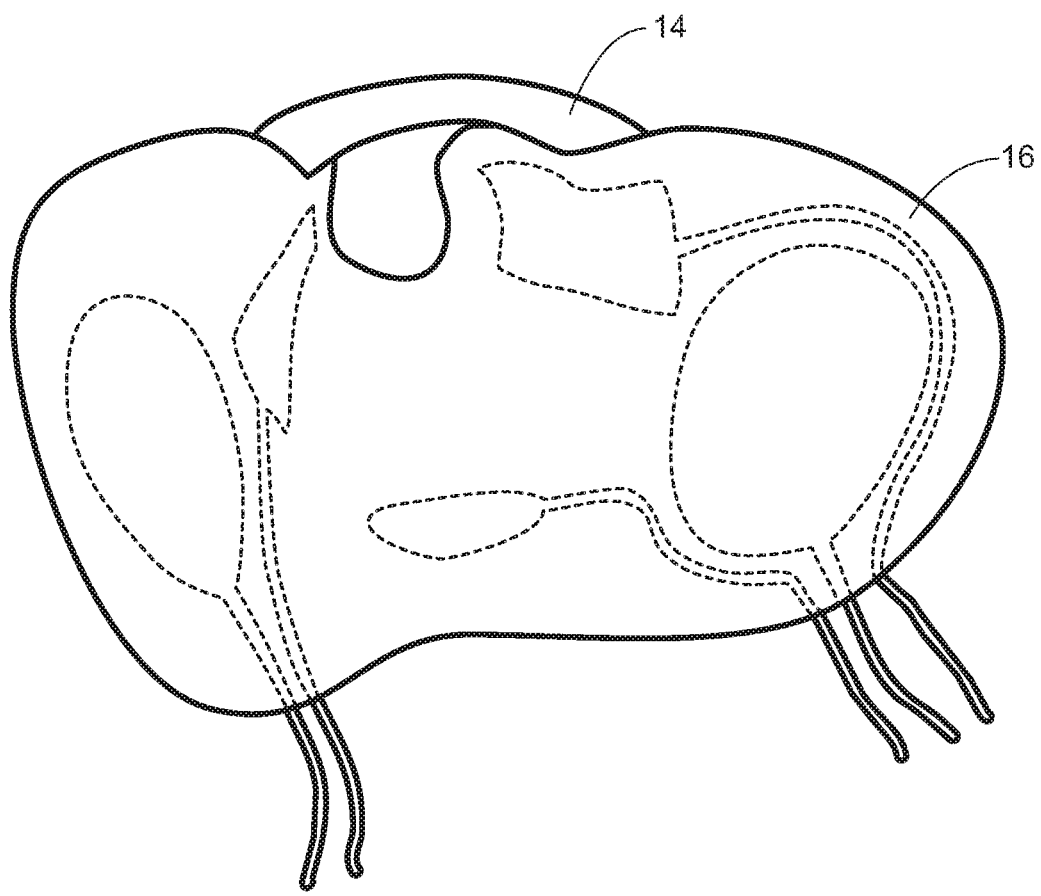
FIG. 43 is a front assembled view of the dynamic interface of FIG. 42.
Figure 44:
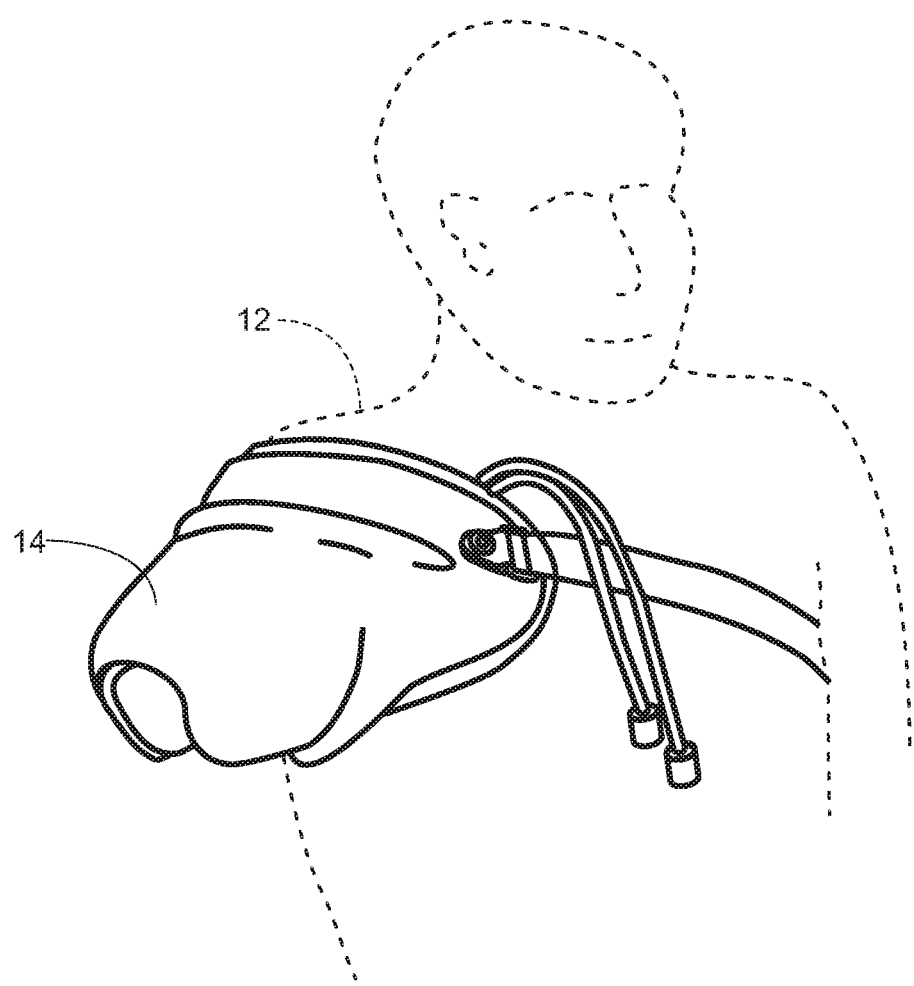
FIG. 44 is a front perspective view of the dynamic support apparatus of FIG. 43 as worn by a patient.
Figure 45:
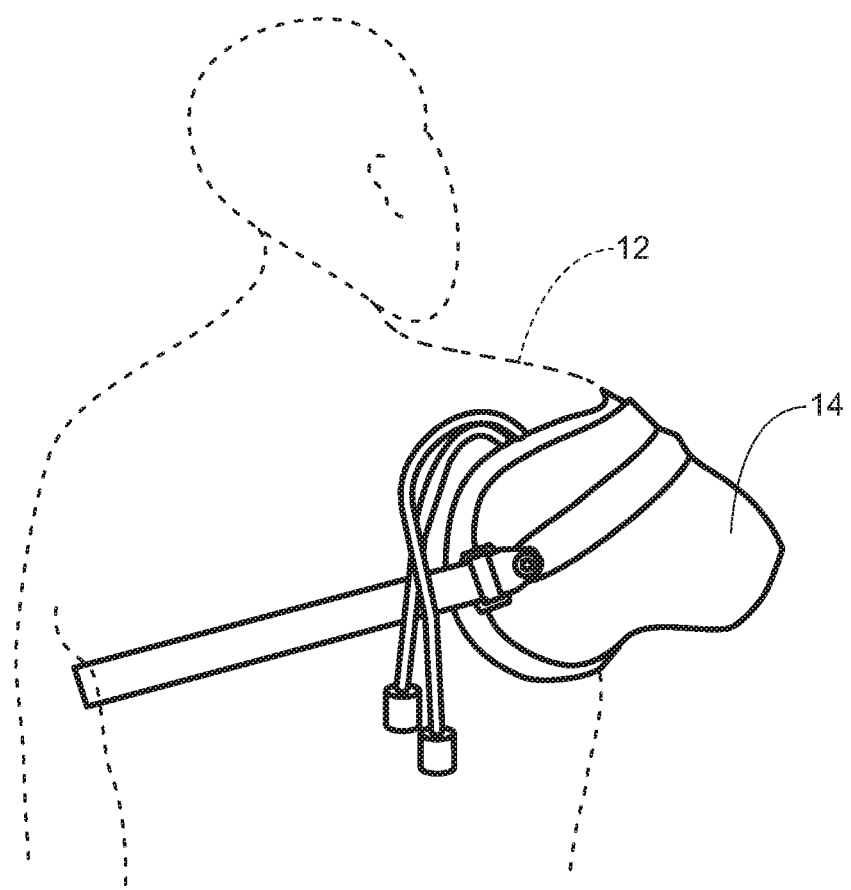
FIG. 45 is a rear perspective view of the dynamic support apparatus of FIG. 43 as worn by a patient.
Figure 46:
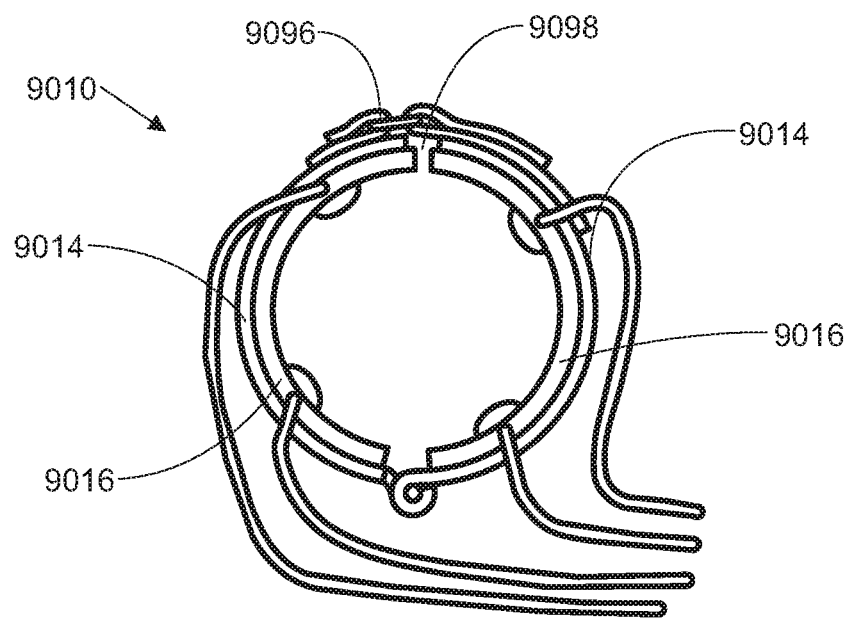
FIG. 46 is a top view of an alternative embodiment of a dynamic support apparatus.
Figure 47:
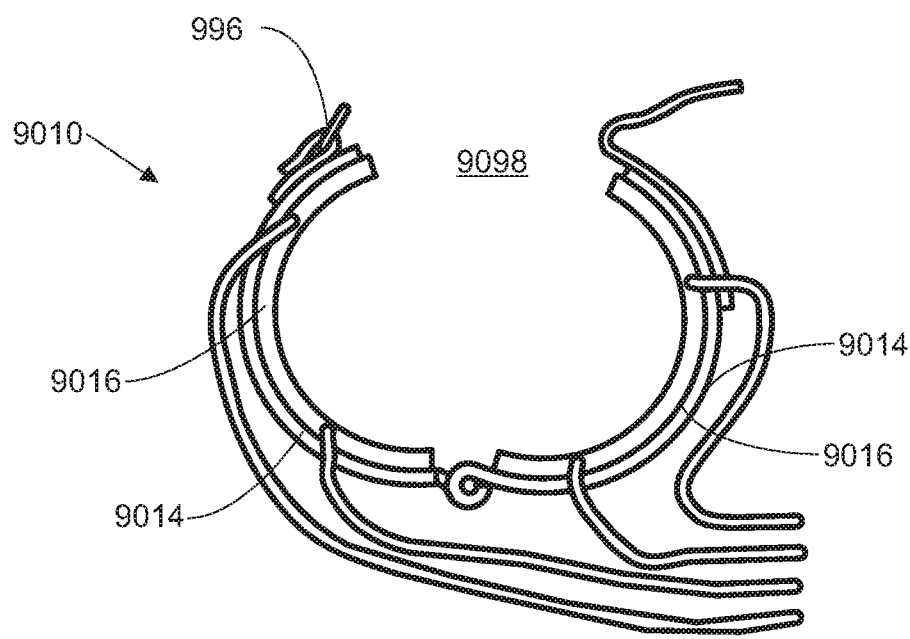
FIG. 47 is the dynamic support apparatus of FIG. 46 when partially opened.
Figure 48:
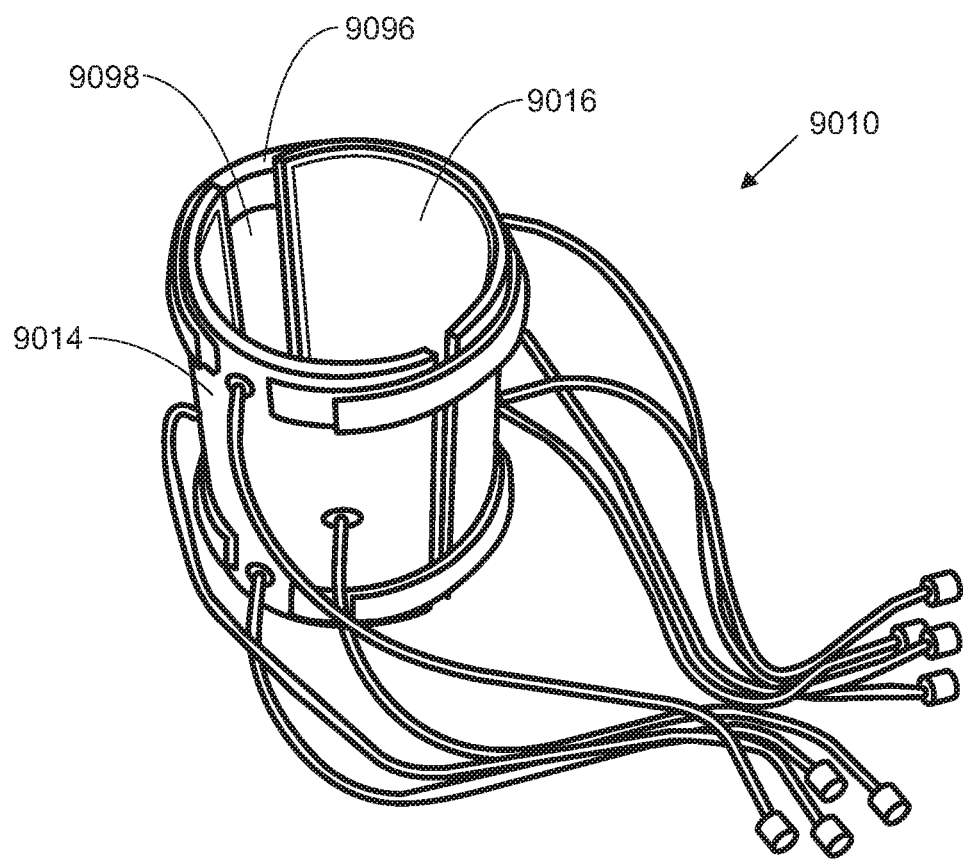
FIG. 48 is a perspective view of the dynamic support apparatus of FIG. 46.
Figure 49:
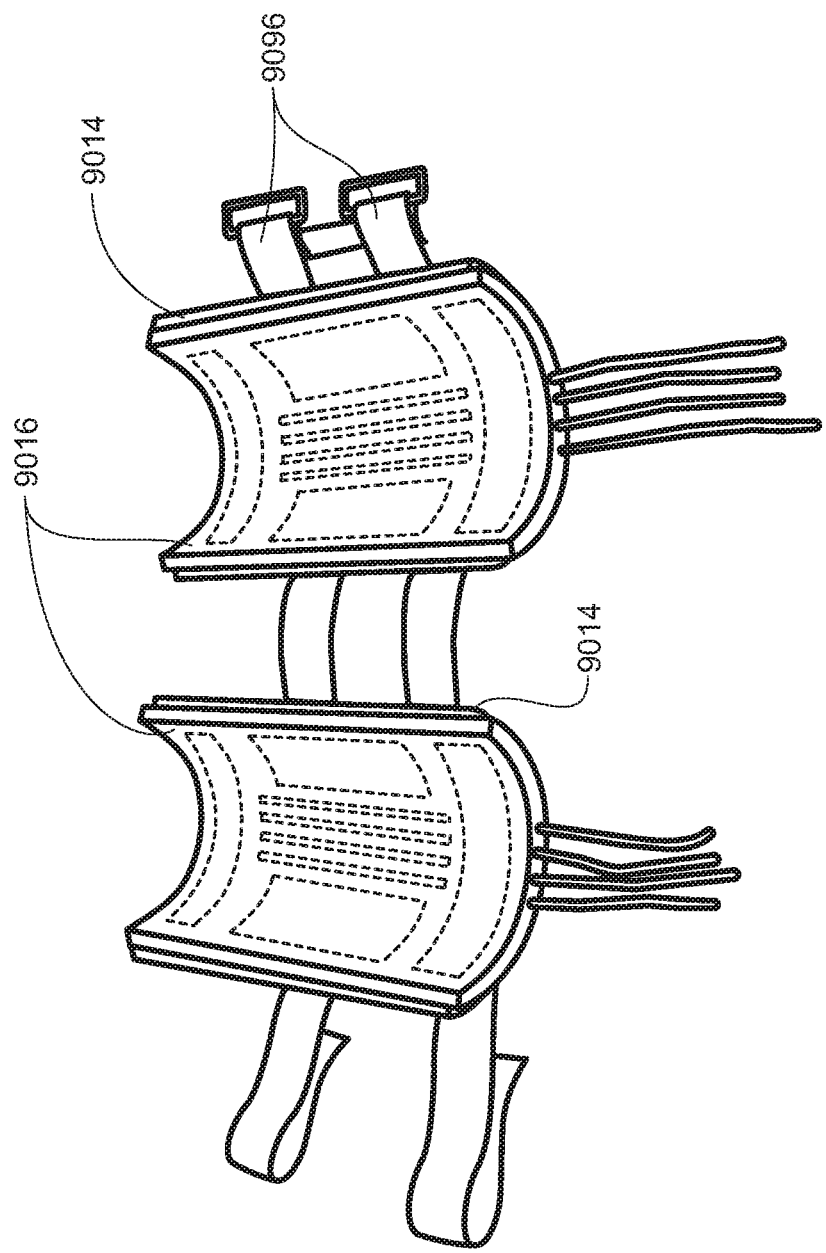
FIG. 49 is a side view of the dynamic support apparatus of FIG. 46 when completely opened.

Referring to the embodiment shown in FIGS. 35 and 36, attached to the support apparatus 8010 is a prosthetic interface 8082 for attaching a prosthesis (not shown) to the support apparatus 8010. The prosthetic interface 8082 is fixedly attached to the support apparatus 8010 by attachment means 8084, which may be rivets, bolts or any similar means of attachment. The prosthetic interface 8082 has a prosthetic mount 8086 for to which the prosthesis may be attached. The prosthetic mount 8086 preferably includes a standard coupling configuration to facilitate attachment of the prosthesis. Although shown as holes 8088, it should be understood that the standard coupling configuration could also be a bolt configuration that interfaces with corresponding holes on the prosthesis. The prosthetic interface 8082 should be rigid in construction, such that it does not bend or flex when the attached prosthesis is used to lift a heavy object.

Referring to FIGS. 37-41, a method of fabricating the dynamic interface of the dynamic support apparatus may be a layer molding technique. For example, for the SD prosthesis support apparatus 8010, such method may involve the steps of scanning the contour of a patient's residuum 8012 in an outline 8090 where the frame will sit on the residuum 8012; flattening the scanned contour so that it can be made into a template for a mold 8092; machining the "flattened" template into the mold 8092; pouring silicone or similar material in the mold 8092 to half the final thickness of the dynamic interface 8016 to create a first interface layer 8093; laying the actuator(s) 8024 and connector(s) 8026 on top of the first interface layer 8093; pouring silicone or similar material on top of the actuator(s) 8024 and connector(s) 8026 to a desired thickness of the dynamic interface 8016 to create a second interface layer 8094; removing the resulting dynamic interface 8016 from the mold 8092; and connecting the resulting dynamic interface 8016 to a control system (not shown) and a frame 8014.

Although described with regard to the SD prosthesis support 8010, as seen in FIGS. 42-45, the dynamic interface 16 fabricated by the layer molding technique described above can also be applied to other types of prosthesis support apparatuses by scanning the appropriate part of the residuum 12 and attaching the resulting dynamic interface 16 to the frame 14 and control system.

An alternative method of fabricating a dynamic interface, for example for a TH prosthesis support apparatus, may involve the steps of scanning the contour of a patient's residuum to form an inner mold of the TH residuum; forming the inner mold of the TH residuum; coating the inner mold with an inner layer of liner made of material such as silicone or similar material; scanning the inner mold to generate an outer mold; forming an outer mold; laying the actuator(s) 24 and connector(s) 26 on top of the inner layer of liner; pouring an outer layer of silicone or similar material on top of the inner layer, the actuator(s) 24, and the connector(s) 26; using the outer mold to form the outer layer of the dynamic interface 16; and connecting the resulting dynamic interface 16 to a control system 18 and a frame 14.

Referring back to FIG. 22, the frame 7014 may be capable of expanding or opening to facilitate donning and doffing the support apparatus. One or more securing mechanisms 7096, such as snaps or latches, may be used to prevent expansion or opening of the frame 7014 while the support apparatus 7010 is being worn by the user.

Referring to FIGS. 46-49, in an alternative embodiment, the support apparatus 9010 may be capable of expanding or opening parallel to its longitudinal axis to facilitate donning and doffing. An opening 9098 of the frame 9014 may run along only a portion of the length of the support apparatus 9010 or may run along the entire length of the support apparatus 9010 from the proximal to the distal end of the apparatus. The securing mechanism 9096 may be flexible, such as a circumferential strap, or more rigidly articulated with mechanical mechanisms to prevent expansion or opening of the frame while the support apparatus is being worn by the user. In this embodiment, the dynamic interface 9016 may be composed of multiple portions, each being attached to a part of the frame 9014.

Some embodiments may also include an exhaust system that is incorporated into the control system. The exhaust system may channel excess gas resulting from the release of pressure in the actuators to one or more exhaust outlets. In the exemplary embodiment, with air as the fluid, the exhaust outlets may vent the air into the atmosphere. In other embodiments, the exhaust outlets may channel the air into a reservoir, from which the air can be drawn back into the system to increase pressure. These exhaust outlets may also be strategically positioned or ducted along the frame to channel flow over the surface of the residuum. This flow could aid convective cooling of the residuum.

The dynamic interface is able to change geometry to provide a fit with the residuum 12. The user may manually actuate the dynamic interface to increase stability as needed. The dynamic support apparatus 10 may include a temperature control system to increase the comfort of the dynamic support apparatus. The frame may be capable of opening to assist the user in donning and doffing the dynamic support apparatus.

The control system may actively actuate the dynamic interface based on fit information provided by sensors. The control system may include preset modes such that the fit may be changed for each mode. The control system may include a massage mode for increasing blood circulation in the residuum.

Figure 52:
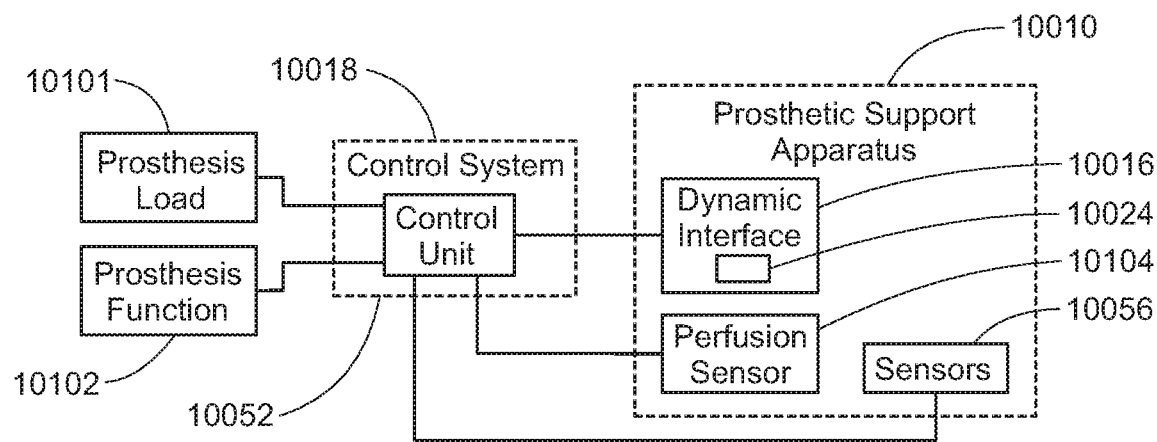
FIG. 52 is a schematic diagram of the prosthetic support apparatus according to another embodiment of the present invention.

Referring to FIG. 52, in some embodiments, the prosthesis (not shown) itself may send signals to the control unit 10052 of the active control system 10018 so that the control unit 10052 may adjust the dynamic interface 10016 of the support apparatus 10010 based on the current usage of the prosthesis (not shown). For instance, the prosthesis (not shown) may send load signals 10100 indicative of the loading of the prosthesis (not shown). The load signals 10100 may be provided to the control unit 10052 by force sensors, compliance sensors and/or motors within the prosthesis (not shown). The prosthesis (not shown) may also send function signals 10102 to the control unit 10052 indicative of a mode of operation of the prosthesis (not shown) and/or of a current positioning of the prosthesis (not shown). The load signals 10100 and the function signals 10102 may be transmitted to the control unit 10052 through a wired connection or wirelessly, for example, through Bluetooth, radio or the like.

The load signals 10100 and the function signals 10102 allow the control system 10018 to actively alter the type and level of support provided to the prosthesis (not shown) by the support apparatus 10010. For example, the control unit 10052 may compensate for load signals 10100 indicating high loading of the prosthesis (not shown) by increasing the actuation of the actuators 10024 of the support apparatus 10010 to better secure the support apparatus 10010 to the residuum 12, shown in FIG. 1. Similarly, the control unit 10052 may compensate for load signals 10100 indicating low loading of the prosthesis (not shown) by decreasing the actuation of the actuators 10024 to loosen the interface between the support apparatus 10010 and the residuum 12, shown in FIG. 1. Thus, the control unit 10052 is able to provide increased support to the prosthesis (not shown) when necessary and to loosen the support to allow for improved blood circulation in the residuum, shown in FIG. 1, during lower loading conditions. The function signals 10102 may also provide improved control to the prosthetic support apparatus 10010. For instance, the function signals

10102 may indicate a current mode of operation of the prosthesis (not shown), which may allow the control unit 10052 to alter the support provided by the support apparatus 10010 to suit the operating mode. For example, if the function signal 10102 indicates that the prosthesis (not shown) has entered a standby mode, the control unit 10052 may decrease actuation of the actuators 10024 or enter a massage mode to increase blood circulation in the residuum 12, shown in FIG. 1. Additionally, the function signals 10102 may provide information to the control unit 10052 indicating a current position of the prosthesis (not shown), for example, through position sensors such as potentiometers, magnetic sensors, Hall effect sensors and the like. Using these function signals 10102, the control unit 10052 may actuate specific actuators 10024 more than others to provide greater support in certain areas of the support apparatus 10010 based on the position of the prosthesis (not shown). Thus, the load signals 10100 and the function signals 10102 may provide for improved active control of the prosthetic support apparatus 10010 based on detected function or loads that the prosthesis (not shown) is imparting on the support apparatus 10010 so that the support apparatus 10010 may adjust appropriately.

Figure 53:
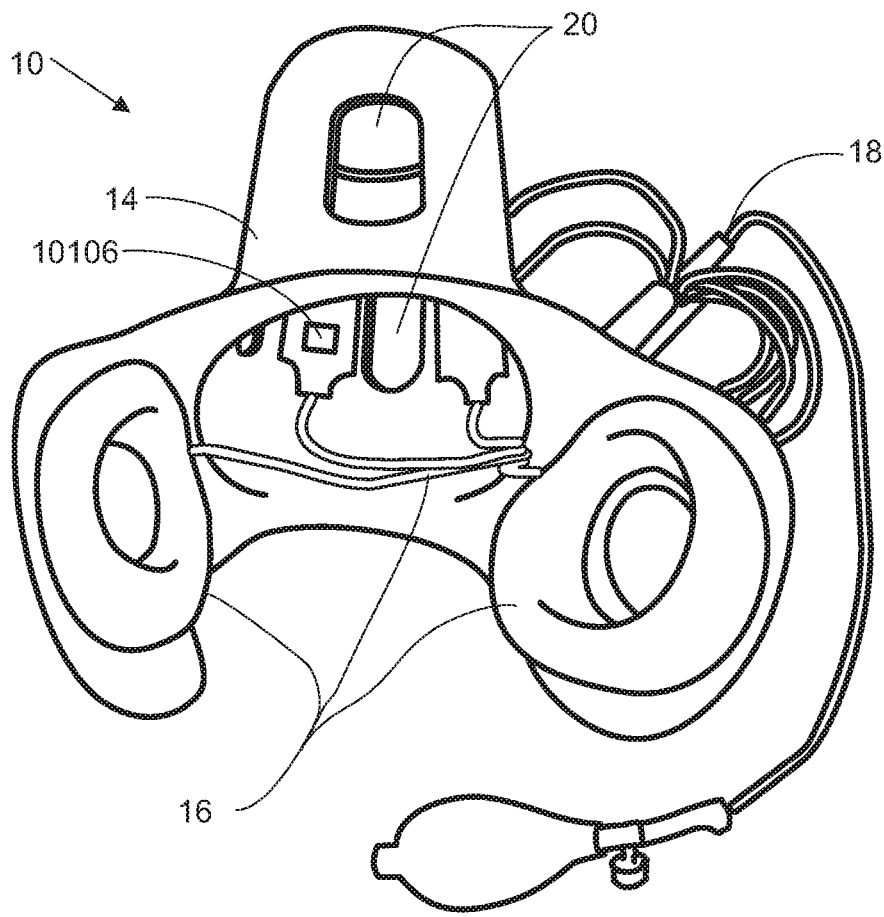
FIG. 53 is a perspective view of the prosthetic support apparatus of FIG. 52.

In various embodiments, the support apparatus 10010 may additionally include perfusion sensors 10104, in communication with the control unit 10052, to determine the amount of blood flowing in tissue of the residuum 12, shown in FIG. 1, underneath the areas of contact with the actuators 10024. For example, referring to FIG. 53, in some embodiments, the perfusion sensor 10104 may be a pulse oximeter 10106 for detecting whether or not the skin is adequately perfused. In other embodiments, the perfusion sensor 10104 may be a blood volume pulse sensor for detecting blood flow within the residuum 12, shown in FIG. 1. If the skin is not, the control unit 10052 may decrease actuation of one or more of the actuators 10024 and/or enter a massage mode to increase blood circulation in the residuum 12, shown in FIG. 1.

Figure 54:
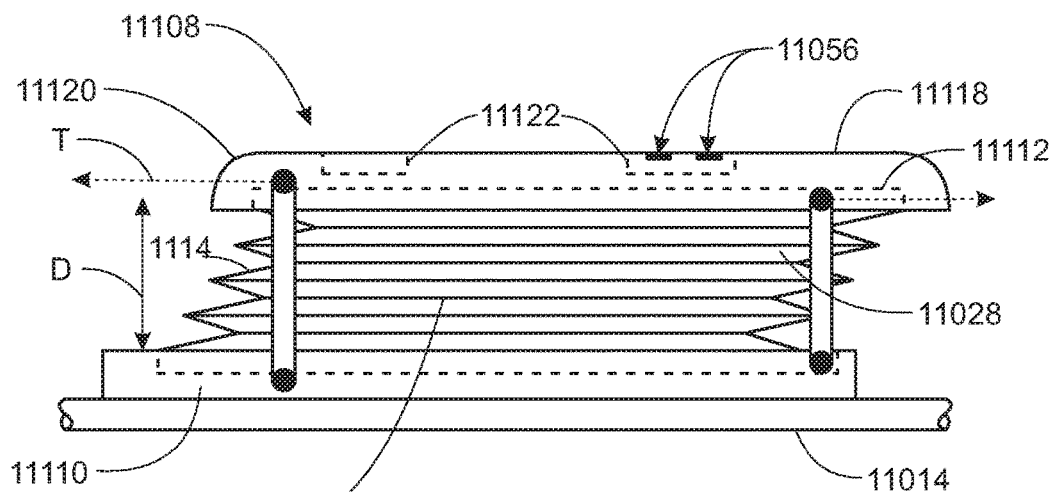
FIG. 54 is a side view of a laterally stabilized bladder in an actuated state according to an embodiment of the present invention.
Figure 55:
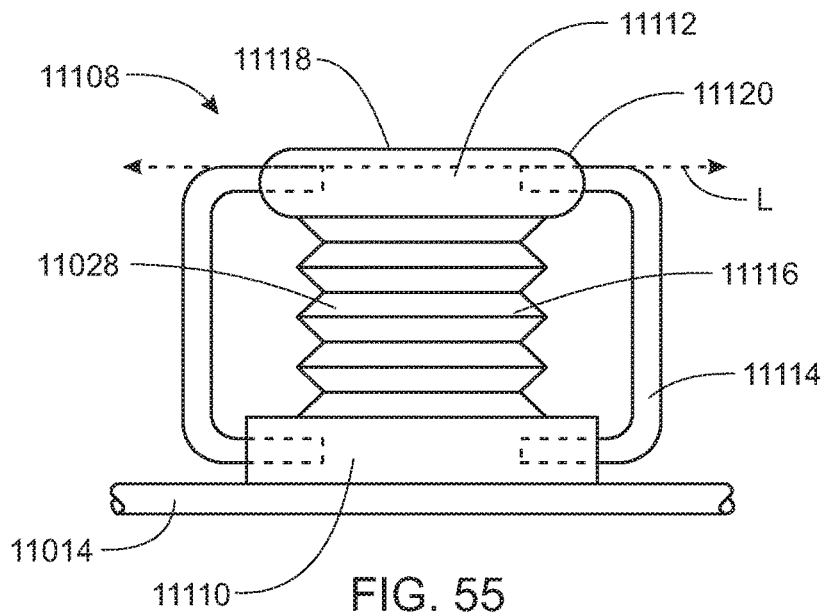
FIG. 55 is a front view of the laterally stabilized bladder of FIG. 54.
Figure 56:
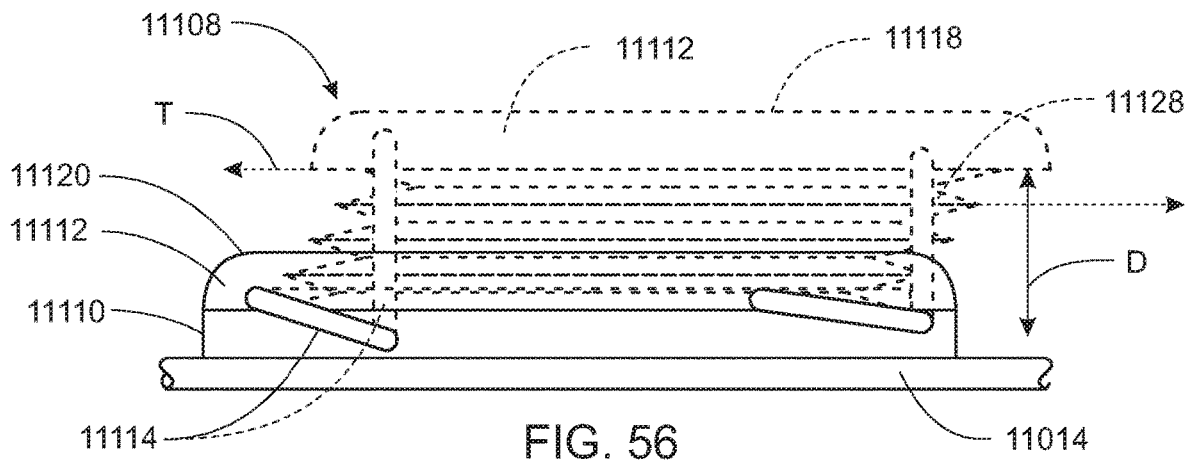
FIG. 56 is a side view of the laterally stabilized bladder of FIG. 54 in an inactuated state.

Referring to FIGS. 54-56, in some embodiments, the support apparatus 10, shown in FIG. 1, may include bladders 11028 having a lateral stabilization system 11108. The lateral stabilization system 11108 includes a base plate 11110 and a cover plate 11112 having the bladder 11028 disposed therebetween. The base plate 11110 may be fixedly secured to the frame 11014 of the support apparatus 10, shown in FIG. 1. The base plate 11110 and the cover plate 11112 are pivotally connected to each other by a linkage 11114, which is preferably a four bar linkage. The linkage 11114 substantially prevents the cover plate 11112 from moving in the lateral direction L relative to the base plate 11110, while allowing the cover plate 11112 to pivot in the transverse direction T away from and back toward the base plate 11110, as seen in FIG. 56. The bladder 11028 may include an accordion sidewall 11116 to provide an increased actuation distance D that the cover plate 11112 may be actuated away from the base plate 11110, and the lateral stabilization system 11108 ensures that lateral stability is not lost as the bladder 11028 actuates to the increased actuation distance D.

The cover plate 11112 preferably includes a residuum contact surface 11118 that is contoured to improve user comfort, for example, by providing rounded corners 11120 that will not dig into the residuum 12, shown in FIG. 1. In other embodiments, the contact surface 11118 may be contoured to the shape of the user's residuum to increase comfort. Referring to FIG. 54, the cover plate may also include one or more sensor cavities 11122 for accommodating one or more sensors 11056 for monitoring the fit of the support apparatus 11010 and/or the condition of the residuum 12, shown in FIG. 1. The sensors 11056 may be, for example, force sensors, pressure sensors, temperature sensors, perfusion sensors or the like. Preferably, the base plate 11110 and the cover plate 11112 are also formed to improve user comfort, for example by being formed from a lightweight material such as an open-cell foam.

Figure 57:
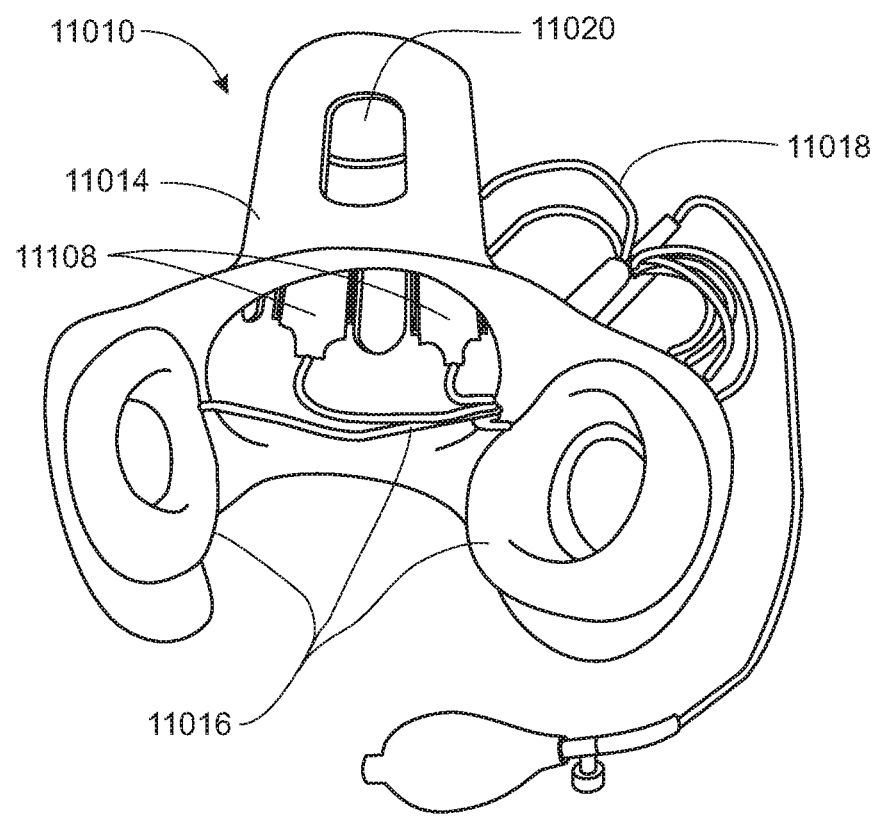
FIG. 57 is a perspective view of an embodiment of a prosthetic support apparatus including the laterally stabilized bladder of FIG. 54.

Referring to FIG. 57, the bladders 11028 having the lateral stabilization systems 11108 may be arranged around the support apparatus 11010 in a manner similar to those discussed above.

Figure 58:
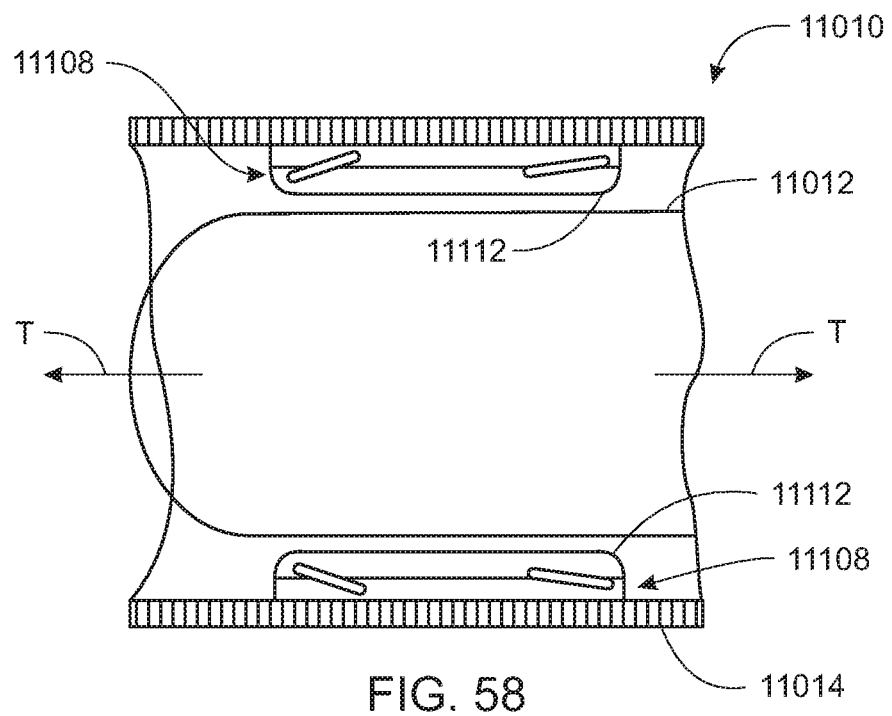
FIG. 58 is a cross-sectional view of the prosthetic support apparatus of FIG. 57 in an inactuated state with a residuum inserted therein.
Figure 59:
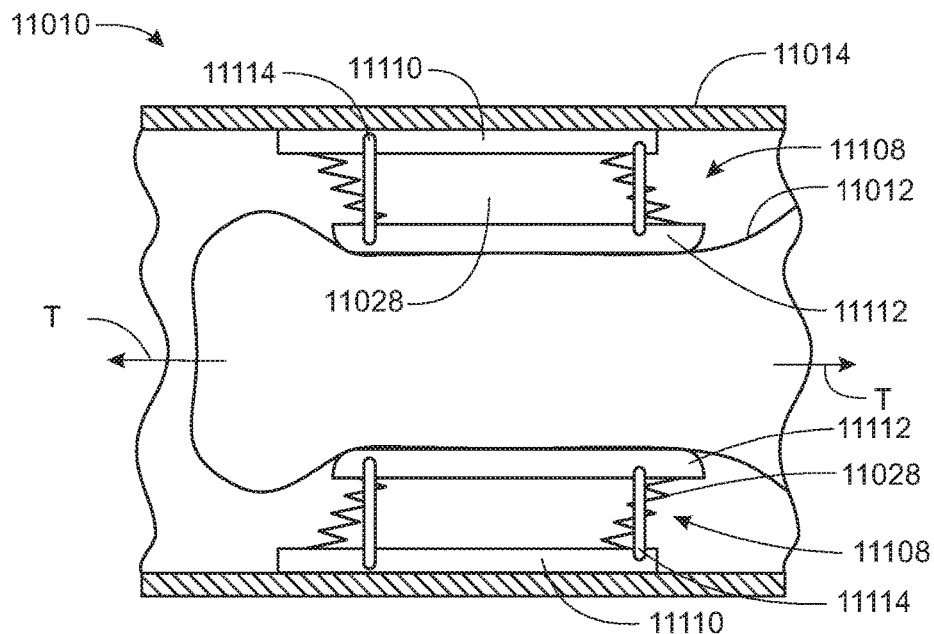
FIG. 59 is a cross-sectional view of the prosthetic support apparatus of FIG. 58 in an actuated state.

Referring to FIG. 58, in operation, the user may insert their residuum 11012 into the support apparatus 11010 in the transverse direction T, while the bladders 11028, shown in FIG. 55, having the lateral stabilization systems 11108 are in an inactuated state. Since the lateral stabilization system 11108 provides for the increased actuation distance D, shown in FIG. 55, when inactuated, the cover plate 11112 may be completely out of contact with the residuum 11012. Thus, the user may insert their residuum 11012 easily, without a mushrooming of the soft residuum tissue that may be caused by contact with the support apparatus 11010. Then, referring to FIG. 59, the bladders 11028 may be actuated, causing them to expand. As the bladders 11028 expand, they push the cover plates 11112 away from the base plates 11110. The linkage 11114 connecting each cover plate 11112 to each base plate 11110 pivots to allow the cover plate 11112 to move away from the base plate 11110, while maintaining lateral stability. The cover plates 11112 are actuated into contact with the residuum 11012 to secure the support apparatus 11010 to the residuum 11012. To remove the support apparatus 11010, the bladders 11028 may simply be returned to their inactuated states, as seen in FIG. 58, and the residuum 11012 may be withdrawn from the support apparatus 11010.

The lateral stabilization system 11108 is advantageous because in prevents unintentional removal of the residuum 11012 from the support apparatus 11010, for example, due to slippage or the like. Specifically, if the residuum 11012 begins to move in the transverse direction T while the bladders 11028 are actuated and in contact with the residuum 11012, the movement will create a camming effect, pulling on the cover plate 11112 and causing the cover plate 11112 to pivot further away from the base plate 11110. As the cover plate 11112 moves further from the base plate 11110, the contact force against the residuum 11012 is increased, securing the support apparatus 11010 more tightly thereto. Thus, the laterally stabilized bladders 11028 provide an improved securing interface when actuated, yet also allow for ease of donning and doffing when inactuated, as discussed above.

Figure 60:
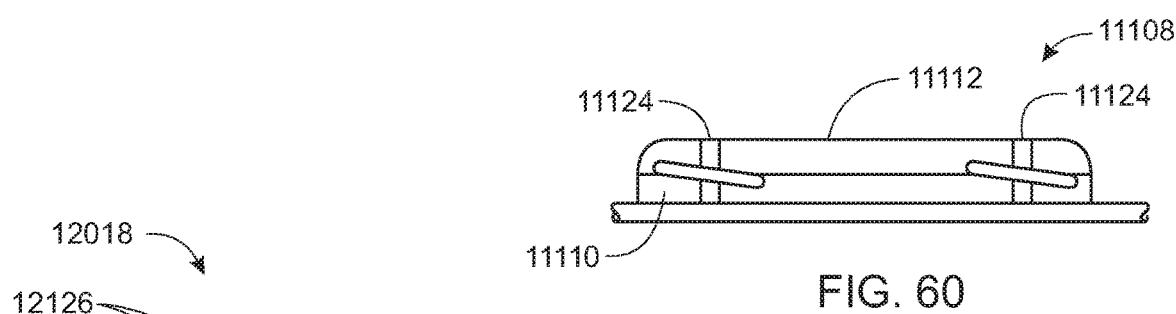
FIG. 60 is a side view of the laterally stabilized bladder of FIG. 56 with a resilient member.

Referring to FIG. 60, in some embodiments, the lateral stabilization system 11108 may be provided with one or more resilient members 11124 connecting the cover plate 11112 to the base plate 11110 and applying a compressive force therebetween. For example, the one or more resilient members 11124 may be elastic members, spring members or the like. The one or more resilient members 11124 ensure that the cover plate 11112 pivots back into contact with the base plate 11110 when in an inactuated state.

Although described in connection with the exemplary embodiment, it should be understood that various changes to the bladders 11028 and lateral stabilization system 11108 may be made. For example, in some embodiments, the bladder 11028 may be anchored directly to the support apparatus 11010, eliminating the need for the base plate 11110. In this embodiment, the linkage 11114 may be pivotally connected directly to the support apparatus 11010. In some embodiments, rather than the bladder 11028 with accordion sidewall 11116, two or more bladders without accordion sidewalls may be arranged between the cover plate 11112 and the base plate 11110 to provide the increased actuation distance D. In other embodiments, the linkage 11114 may be telescopic, rather than pivotal, thereby providing stability in both the lateral and transverse directions. Additionally, although each bar of the linkage 11114 is shown as being substantially the same length, the lengths may be varied to alter the configuration of the cover plate 11112 relative to the base plate 11110. For example, rather than being parallel to the base plate 11110, the cover plate 11112 may instead be angled to one side in the lateral direction L or angled to the front or back in the transverse direction T.

Although the lateral stabilization system 11108 has been described as surround the bladder 11028, in other embodiments, the bladder 11028 may include an open cell foam structure disposed inside the bladder 11028 to create internal struts and connectors, which are flat when the bladder 11028 is deflated. In operation, the bladder 11028 is anchored to the base plate 11110 or frame 11014. As the bladder 11028 inflates, the bladder 11028 the structure of the foam or material inside the bladder 11028 provides the bladder 11028 with lateral stability. In some embodiments, the open cell foam structure may be toroidal. In various other embodiments, a honeycomb or multi-tube structure may be introduced to provide greater lateral stability when the bladder 11028 is inflated.

Figure 61:
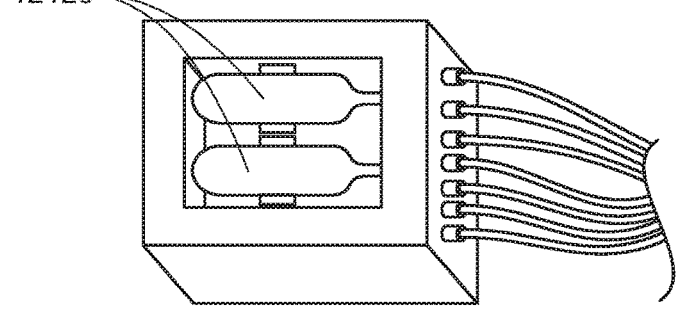
FIG. 61 is a perspective view of a control system according to another embodiment of the present invention.

In various embodiments, bladder inflation may be accomplished by using compressed gas from a tank, such as carbon dioxide ($CO_2$), rather than air supplied by a pump. For example, referring to FIG. 61, the control system 12018 may include one or more $CO_2$ cartridges 12126. The $CO_2$ cartridges are advantageous because they may quickly fill the bladders 28, shown in FIG. 3. Additionally, the $CO_2$ cartridges are themselves refillable, so they may simply be removed from the control system 12018 to be refilled or replaced. Inflation using the one or more $CO_2$ cartridges 12126 may also improve the temperature control mechanism 19, shown in FIG. 1, because the $CO_2$ may decrease in temperature as it expands to fill the bladders 28, shown in FIG. 3, thereby cooling the user where the user is in contact with the bladders 28.

Figure 62:
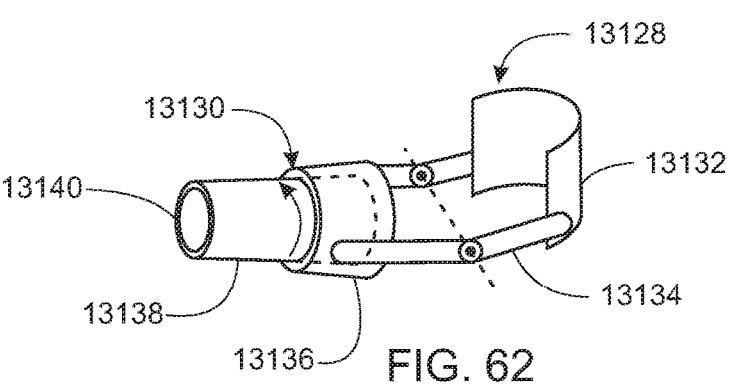
FIG. 62 is a perspective view of a prosthetic support apparatus representative of a transradial system according to yet another embodiment of the present invention.

Depending upon the degree of amputation of the user of the prosthetic arm, in some embodiments, it may be desirable to couple some degree of movement of the user's arm with a shortened prosthetic arm, for example, a prosthetic arm that provides only wrist flexion and hand movement capabilities. Thus, referring to FIG. 62, a trans-radial socket 13128 may be provided for trans-radial amputees that are still able to pronate and supinate their residuum (not shown). The trans-radial socket 13128 includes a bracket body 13130 connected to a cup brace 13132 by two hinged brackets 13134. The bracket body includes an outer cylinder portion 13136 attached to the hinged brackets 13134 and an inner tubular portion 13138 partially rotatably fixed within the outer cylinder portion 13136 and extending axially outward therefrom to a distal end 13140. In operation, the prosthetic arm (not shown) is mounted to the trans-radial socket 13128 at the distal end 13140 of the inner tubular portion 13138. The user may then insert their residuum into the inner tubular portion 13138. The cup brace 13132 may then be slid along their upper arm behind the user's elbow. The hinged brackets allow the user to bend their elbow to move the bracket body 13130. Additionally, the user may pronate and/or supinate their residuum, to rotate the inner tubular portion 13138 relative to the outer cylinder portion 13136, which in turn causes the prosthetic arm mounted to the inner tubular portion 13138 to rotate. Thus, the trans-radial socket 13128 provides for a reduction in the size of the prosthetic arm by eliminating the need for a wrist rotator for users having natural rotation capability in their residuum. This reduction in the size of the prosthetic arm results in a corresponding reduction in weight of the prosthetic arm, thereby improving user comfort. Additionally, the trans-radial socket 13128 eliminates the need for the prosthetic arm to provide wrist rotation, thereby making the prosthetic arm easier for the user to control by reducing the number of joint movements for which the user must learn new control inputs. Additionally, reducing the number of joint movements provided by the prosthetic device may also improve battery power usage and lead to extended battery life.

Referring to FIG. 63, an embodiment of a dynamic support system 142 is shown. In some embodiments, the dynamic support system 142 includes both hardware and control components for controlling the hardware. In some embodiments, the hardware may be the dynamic support apparatus 10, which may include, but is not limited to, one or more of the following: at least one dynamic interface 16, which may include, but is not limited to, bladder actuators 28, shown in FIG. 3, and or strap actuators 8068, shown in FIG. 28, connectors 8026, shown in FIG. 28, such as tubing and/or other elements to support integration of the dynamic support apparatus 10. The dynamic support system 142 therefore may include the control systems 18 for executing control logic and/or one or more methods for controlling the one or more dynamic interfaces 16 using, for example, connectors 8026, shown in FIG. 28, such as tubing, and in some embodiments, other hardware elements. In some embodiments, the dynamic support apparatus 10 and the control system 18 for the dynamic support apparatus 10 may be used with a prosthesis 11 similar to one or more embodiments described in U.S. patent application Ser. No. 12/706,609, filed Feb. 16, 2010 and entitled Arm Prosthetic Device, now U.S. Publication No. US-2010-0274365-A1, published Oct. 28, 2010, which is hereby incorporated by reference in its entirety. Additionally, the dynamic support apparatus 10 may be used together with control systems, such as arm control unit 143 for the prosthesis 11, which may be similar to one or more embodiments described in U.S. patent application Ser. No. 12/706,575, filed Feb. 16, 2010 and entitled System, Method and Apparatus for Control of a Prosthetic Device, now U.S. Publication No. US-2010-0268351-A1, published Oct. 21, 2010, U.S. patent application Ser. No. 12/706,471, filed Feb. 16, 2010 and entitled System, Method and Apparatus for Orientation Control, now U.S. Publication No. US-2010-0211185, published Aug. 19, 2010, U.S. patent application Ser. No. 12/027,116, filed Feb. 6, 2008 and entitled Method and Apparatus for Control of a Prosthetic, now U.S. Publication No. US-2008-0243265-A1, published Oct. 2, 2008, and U.S. patent application Ser. No. 13/088,085, filed Apr. 15, 2011 and entitled System, Method and Apparatus for Control of a Prosthetic Device, now U.S. Publication No. US-2011-0264238-A1, published Oct. 27, 2011, each of which is hereby incorporated by reference in its entirety. In some embodiments of the dynamic support system 142, the dynamic support apparatus 10 is in communication with both the user's residuum 12 and the prosthesis 11 and is, therefore, able to vary its configuration as the state of the residuum 12 and/or the prosthesis 11 changes. For instance, as discussed above, the dynamic support apparatus 10 includes a variety of sensors for detecting the condition of the residuum, such as temperature sensors and perfusion sensors 10104, shown in FIG. 52. Additionally, as discussed above, the dynamic support apparatus may also receive prosthesis load information 10100 and prosthesis function information 10102, shown in FIG. 52, from the prosthesis 11. The dynamic support system 142 also includes a variety of interface sensors, such as pressure sensors 7056, shown in FIG. 22, detecting the condition of the interface between the residuum 12 and the dynamic support apparatus 10. Information from all of these various sensors and sources are used in the dynamic support system 142 to alter the state of the dynamic interface 16, thereby changing the fit of the dynamic support apparatus 10. The dynamic support system 142 may also include interface stimulators 144 to provide feedback to the user regarding the state of the dynamic interface 10. For instance, the dynamic support system 142 may use tactors 146 to provide vibration or other tactile feedback to the user. Additionally, the dynamic support system 142 may also include a variety of passive elements for improving comfort and/or fit of the dynamic support apparatus 10 and/or for communicating information to the user. For instance, the apertures 20 provide passive temperature control and the contact between the dynamic support apparatus 10 and the residuum 12 acts as a passive loading interface stimulator. Thus, the dynamic support system 142 provides beneficial integration between the dynamic support apparatus 10, the prosthesis 11 supported by the dynamic support apparatus 10 and the user.

Figure 64A:
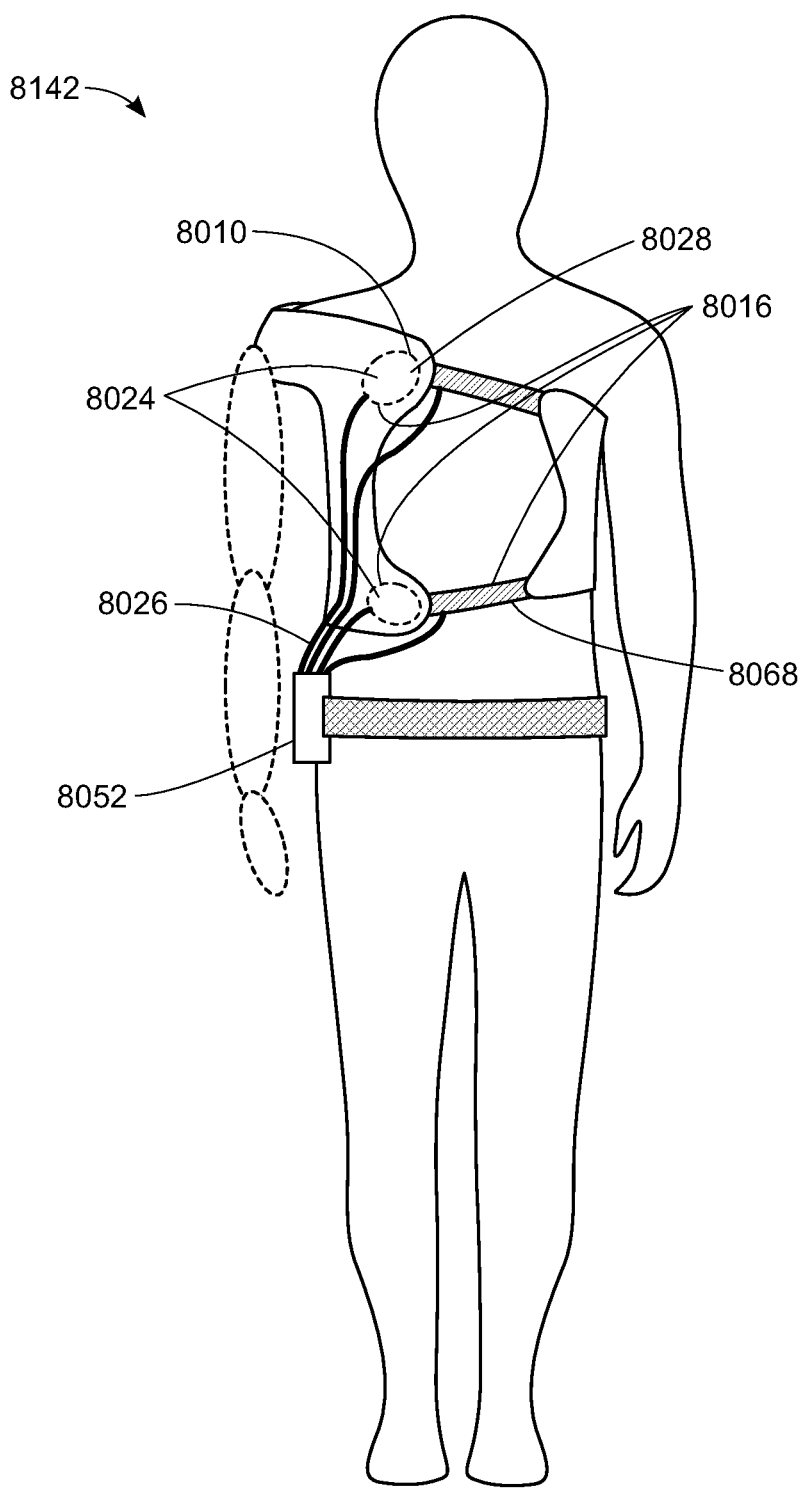
FIG. 64A is a schematic diagram of a dynamic support system together with a dynamic control unit apparatus according to one embodiment.
Figure 64B:
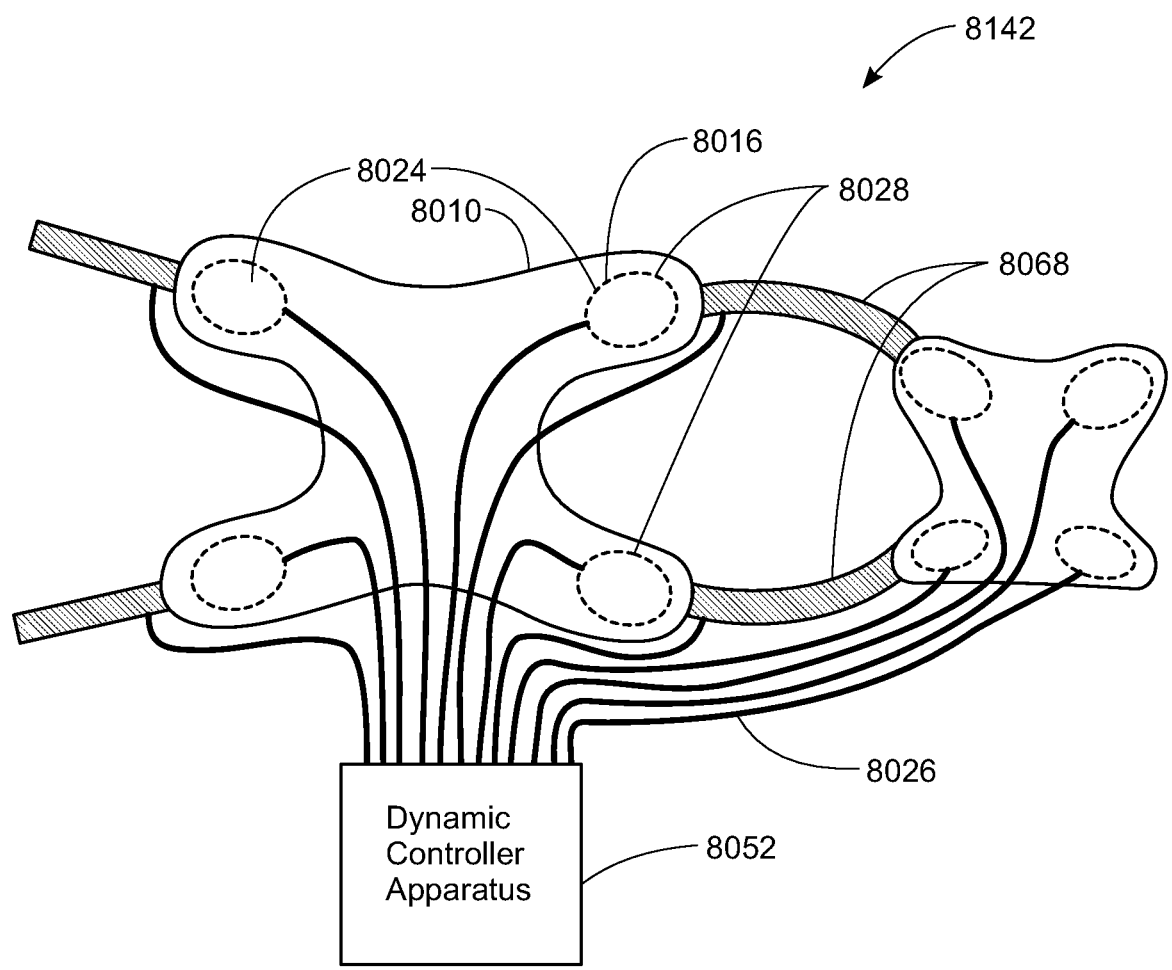
FIG. 64B is a schematic diagram of a dynamic support system according to one embodiment.

Referring now to FIGS. 64A and 64B, in some embodiments, the control system 18, shown in FIG. 63, includes control unit 8052 (or dynamic control unit apparatus). The control unit 8052 may be a portable electronic device that may be worn on the dynamic support apparatus 8010 and/or on a belt or other part of a user's clothing. As shown in FIG. 64A, the user is wearing the control unit 8052 on a belt. The control unit 8052 is an interface between the dynamic support system 8142 and the user. The control unit 8052 allows the user to control the mode and/or inflation state of the dynamic support apparatus 8010, and in some embodiments, may indicate the state and or mode of the dynamic support apparatus visually and/or using audio. In some embodiments, the control unit 8052 includes a user interface (not shown) which may include, but is not limited to, one or more of the following: one or more buttons, one or more capacitive switches, one or more jog wheels, one or more monitors, one or more LEDs or other lights, and/or one or more speakers. The control unit 8052 may be in communication with a prosthetic device control unit, such as arm control unit 143 for the prosthesis 11, both shown in FIG. 63, and/or may be integrated with the prosthetic device control unit and may provide advanced information related to functional activity of the prosthesis 11, shown in FIG. 63. As discussed above, an example of a prosthetic device control unit is described in U.S. patent application Ser. No. 12/706,609, filed Feb. 16, 2010 and entitled Arm Prosthetic Device, now U.S. Publication No. US-2010-0274365-A1, published Oct. 28, 2010, and an example of various control methods and systems for a prosthetic device may be found in U.S. patent application Ser. No. 12/706,575, filed Feb. 16, 2010 and entitled System, Method and Apparatus for Control of a Prosthetic Device, now U.S. Publication No. US-2010-0268351-A1, published Oct. 21, 2010, U.S. patent application Ser. No. 12/706,471, filed Feb. 16, 2010 and entitled System, Method and Apparatus for Orientation Control, now U.S. Publication No. US-2010-0211185, published Aug. 19, 2010, all of which are herein incorporated by reference in their entireties. The control unit 8052, in various embodiments, is attached to the dynamic interfaces 8016 of the dynamic support system 8142, e.g., actuators 8024 such as bladders 8028 and/or straps 8068, by way of connectors 8026, e.g. flexible tubing; for example, clear flexible tubing in a flat ribbon configuration as seen in FIG. 64B.

In some embodiments, the control unit 8052 may include multiple user inputs 8055, shown in FIG. 19A, for example, buttons, each to activate a particular/specific support apparatus control mode. For example, in some embodiments, one or more buttons may be used to function as described below, however, other embodiments may include additional functionality and still other embodiments may include a "function" or "toggle" switch so as to use the same button or user input 8055, shown in FIG. 19A, for multiple functionalities.

In some embodiments, the control unit 8052 may include a VENT button (not shown) that, when pressed, may signal the control system 18, shown in FIG. 63, to control all actuators 8024, such as bladders 8028 to vent and deflate, thereby allowing easy donning and doffing of the dynamic support apparatus 8010. In some embodiments, where air is used to inflate and deflate actuators 8024, the vented air may be routed back into the dynamic support apparatus 8010 and across the user's skin to provide a moderate cooling effect, for example as discussed in connection with ducts 64 and orifices 66, shown in FIG. 25.

In some embodiments, the control unit 8052 may include a pressure UP button (not shown) that, when pressed from the vented (evacuated) or non-actuated state, may signal the control system 18, shown in FIG. 63, to actuate or inflate all the actuators 8024, such as bladders 8028, in a preprogrammed sequence up to a Baseline inflation pressure. This pressure UP button (not shown) may advantageously be used in some embodiments of a donning process. The Baseline pressure, in some embodiments, may be a pressure that permits the dynamic support apparatus 8010 to be worn for long periods of time while providing enough stability for moderate activity with the prosthesis 11, shown in FIG. 63. The relationship between the inflation pressure and the contact pressure on the user's tissue is dependent upon a variety of factors including characteristics of the actuators 8024, any tissue preload, the compliance of the soft tissue and the like.

In some embodiments, when the actuators 8024 of the dynamic support system 142, shown in FIG. 63, are already actuated or inflated, the pressure UP button (not shown) may be used to increase a current pressure setpoint in discrete steps up to a programmed High pressure setting. For example, in some embodiments, the user may press the pressure UP button (not shown) before or during heavier or high-load activity with the prosthesis 11, shown in FIG. 63. The High pressure setting, in some embodiments, may be used to provide maximum grip and stability of the dynamic support apparatus 8010 with the user within the limits of the dynamic support system 142, shown in FIG. 63. In some embodiments, the High pressure setting is not be intended for all-day use, i.e., the control system 18, shown in FIG. 63, may be preprogrammed to limit to amount of time in the High pressure setting to avoid negative effects to the tissue of the user. In some embodiments, the control system 18, shown in FIG. 63, may be pre-programmed such that after meeting a threshold of time in the High pressure setting, additional pushes of the pressure UP button (not shown) may be ignored.

In some embodiments, the control unit 8052 may include a pressure DOWN button (not shown) that, when pressed, decreases the current pressure setpoints for all channels, in a stepwise down fashion, until a pre-programmed Low pressure setting is reached. The Low pressure setting may be the minimum inflation that permits the support to remain stable on the user with the weight of the prosthesis 11, shown in FIG. 63, and permit very minimal activity, e.g., but not limited to, sitting in a chair. In some embodiments, once the Low pressure setting is reached, additional pushes of the DOWN button (not shown) may be pre-programmed to be ignored by the control unit 8052.

In some embodiments, the control unit 8052 may include a MASSAGE button (not shown) for controlling the dynamic support system 142, shown in FIG. 63, to enter massage mode. Depression of the MASSAGE button may cause a subset of the bladders 8028 to, one at a time, decrease pressure from the current pressure setpoint to provide relief to the tissue underneath the bladder 8028. For example, when the bladders 8028 are mostly or heavily inflated, one bladder 8028 at a time will deflate to the Low pressure setting, remain there for several seconds, and then re-inflate to the current pressure setpoint. The next bladder 8028 then deflates, etc. In some embodiments, where the current pressure setpoint is already near the Low pressure setting, the selected bladder 8028 may inflate up to the Baseline pressure setting or higher before returning to the Low pressure setting. The massage mode may cycle once or many times, depending on user preference, and, in some embodiments, may be exited at any time by pressing any of the other buttons of the control unit 8052.

Figure 80:
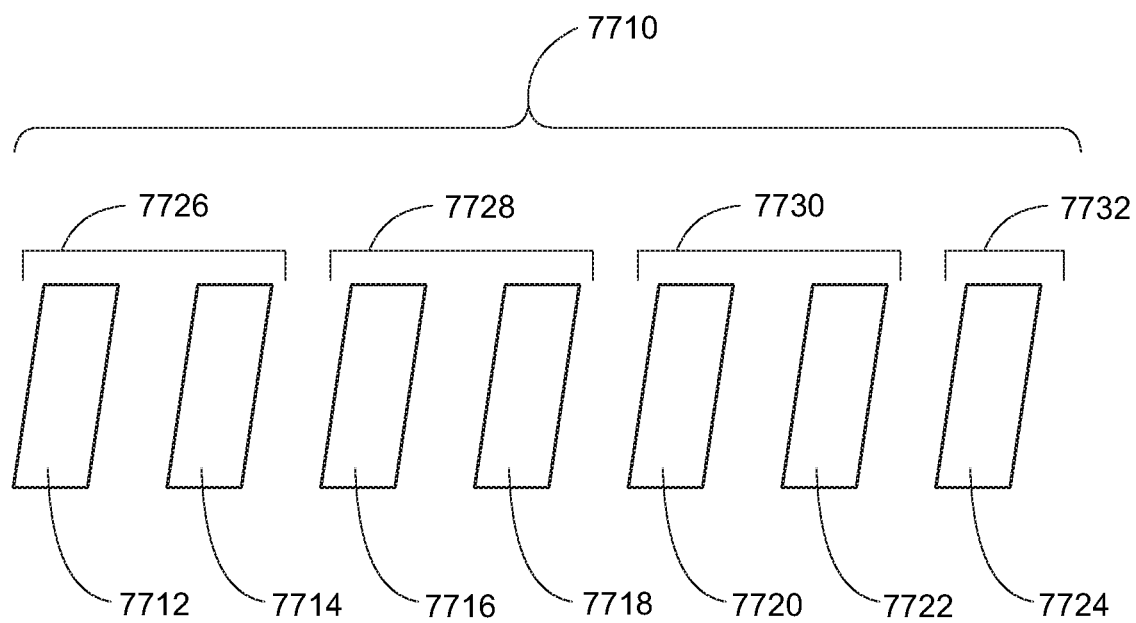
FIG. 80 is shows an illustration of one embodiment of bladder grouping.

In some embodiments, the various embodiments of the control unit may include a system for controlling the individual inflation and/or deflation of the bladders. In some embodiments, the control unit may include a system of individually controlling a group of bladders. For example, and referring now also to FIG. 80, in some embodiments, a collective multiple bladders 7710, where, in some embodiments, may include seven bladders 7712, 7714, 7716, 7718, 7720, 7722, 7724, as an example, may be either individually control unit, i.e., the pressure of each bladder 7712, 7714, 7716, 7718, 7720, 7722, 7724 may be increased or decreased separately and individually from the other bladders. In some embodiments, the bladders 7712, 7714, 7716, 7718, 7720, 7722, 7724 may be grouped, for example, group one 7726 may include two bladders 7712, 7714, group two 7728 may include two bladders 7716, 7718, group three 7730 may include two bladders 7720, 7722 and group four 7732 may include one bladder 7724. However, these groupings are merely given as an example for illustration purposes and in various other embodiments, any one or more of the groupings may include one or more bladders. In some embodiments, each bladder may form a group.

Thus, in some embodiments, one group may be selected, for example, group one 7726, and increasing or decreasing the pressure will increase or decrease the pressure of all of the bladders within the group by the same amount, for example, bladders 7712, 7714. However, the remaining groups, for example, groups two, 7728, three 7730 and four 7732, will remain unchanged.

Figure 81:
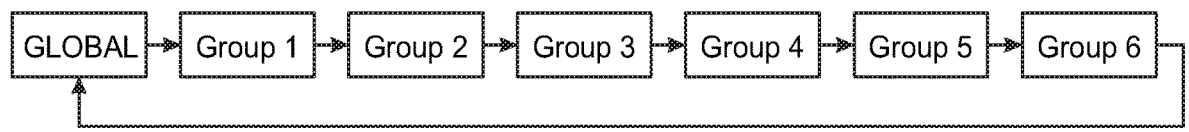
FIG. 81 shows a flow chart of one embodiment of toggling the settings for the control unit.

In various embodiments, a toggle switch may be used to cycle through the groups 7726, 7728, 7730, 7732. In some embodiments, an indication of the currently selected group may include, but is not limited to, a slight increase or a slight decrease in pressure for the selected group. For example, while toggling through the various groups 7726, 7728, 7730, 7732, when, for example, group one 7726 is selected, bladders 7712, 7714 in group one 7726 may increase decrease in pressure. Then, while continuing to toggle, group two 7728 is selected, bladders 7716, 7718 may increase slightly in pressure. This may continue through all of the available groups. In some embodiments, a leak compensation algorithm may be suspended while in toggle mode. In some embodiments, toggling may include a predetermined/preprogrammed threshold timeout that, once met, may toggle to a home setting, which, in some embodiments, may be a setting that actuates all of the bladders 7712, 7714, 7716, 7718, 7720, 7722, 7724. In some embodiments, the home setting may be the last group that was modified, i.e., if the last modification was made to a group, for example, group two 7728, then, after a threshold timeout is met, the system may return to that group, i.e., group two 7728. In some embodiments, the home setting may be a global setting where all of the bladders may be modified together. In some embodiments, the toggle may used to sequentially cycle through all of the groups individually, for example, and referring now also to FIG. 81, starting at the global setting and toggling to advance to each group, in an infinite loop. As discussed above, in some embodiments, once a modification is made to a specific group and a timeout threshold is met, the system, once turned on/used again, may be in the mode to modify the last group modified. In these embodiments, toggling will advance to the next group, sequentially, and in an infinite loop.

Although decreasing or increasing the pressure in the bladders may be used in some embodiments to indicate to the user the current mode, in some embodiments, LEDs, beeps/audio signal and/or vibratory signals may be used to indicate the mode as the toggle sequence is continued. In some embodiments, once the user wakes up the system, the control unit may indicate to the user the current mode. For example, the system may produce an audio and/or vibratory signal and/or may light a particular LED. For example, in some embodiments, and with reference also to FIG. 77D, LEDs 7706 may be included on the control until, one for each bladder. In some embodiments, if all of the LEDs are energized, this may indicate the global setting. In some embodiments, the LED(s) indicating the current setting may become de-energized once the system has met the threshold timeout. In some embodiments, the LED(s) may continually be energized to indicate the current setting.

In some embodiments, in addition to the various buttons discussed above, and additional buttons which may be used on the dynamic control unit 8052, the dynamic support system 142, shown in FIG. 63, may include one or more remote user inputs and/or buttons which may be positioned elsewhere on the user's body, on the dynamic support apparatus 8010 and/or on the prosthesis 11, shown in FIG. 63. Depending on the type of user inputs and where they are mounted, a software application may configure the inputs and the resulting functionality to accommodate user needs and/or preferences. In some embodiments, a single input may be desired and may replicate the functionality of multiple buttons. However, in various other embodiments, one or more buttons and/or user inputs may be positioned remotely from the control unit 8052.

In some embodiments of the dynamic support system 142, shown in FIG. 63, the dynamic actuators 8024 may include settings, for example, but not limited to, the low, baseline, and high pressure modes discussed above. These settings may, in some embodiments, be unique to the user and therefore may be preprogrammed and/or re-programmed depending on the user's needs.

As one mere example for illustrative purposes, the following exemplary description of possible configurations of user customization based on user needs is provided. This exemplary description is provided only for illustrative purposes and is in no way limiting, as should be understood by the very customizable characteristics of the settings of the dynamic support system 142, shown in FIG. 63. With respect to the various embodiments of the actuators 8024 (which, may include bladders 8028 and/or straps 8068 with inflatable elements), in some illustrative embodiments, the actuator settings may be typically inflated to pressures of ~4 psi (200 mmHg) for a nominal fit of the dynamic support apparatus 8010, and ~7 psi (350 mmHg) where enhanced fixation is needed. In some exemplary embodiments, approximately 70% of the inflation pressure plus a constant related to static preload may be required to expand the bladder membrane to the volume typically used in the system. Thus, in some embodiments, actual tissue contact pressures may therefore be approximately 30% of the inflation pressures plus the constant related to static preload. Similarly, in some exemplary embodiments, the retaining straps 8068 may be pressurized to 2 psi-4 psi (100 mmHg-200 mmHg) for a nominal fit, and pressures of 6 psi-10 psi (300 mmHg-500 mmHg) for a more secure fit. In some embodiments, the forces generated by the load straps 8068 may be of a similar magnitude as may be generated with manual VELCRO and other strapping systems. Operating pressures may exist on a continuum and may be customized to the user for best fit. The typical pressures discussed herein are for static conditions; during activity these pressures may be higher or lower depending on the loads being transferred through the dynamic support apparatus 8010. In some embodiments, these "typical" pressures may be referred to as the "Baseline" pressures discussed above, which are pressures from which a deflation or inflation may be desired and/or necessary depending on one or more factors, including, but not limited to, user activity.

Referring back to FIG. 63, various embodiments of the dynamic support system 142 may provide benefits to the user which may include, but are not limited to, one or more of the following: increased prosthesis stability through improved engagement with the muscle-skeletal system of the user's residuum 12; increased ease of user adjustment of actuator force based on user activity; and/or reduced don/doff effort. The various embodiments of the control system 18 for the dynamic support apparatus 10 may more readily meet the immediate needs of the user and thus provide a varying degree of support to the user in accordance with the activity being performed by the user. In this way, the dynamic support apparatus 10 is dynamic and, thus, the pressure of one or more actuators 8024, shown in FIG. 64A, may vary with activity levels and needs of the user.

Figure 65:
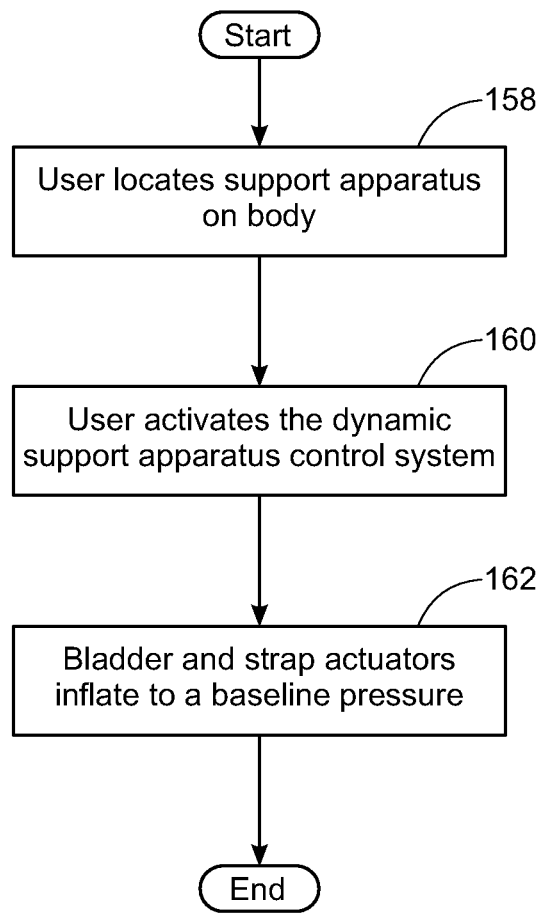
FIG. 65 is a flow diagram of one embodiment of the methods for donning the dynamic support apparatus.

Referring now to FIG. 65, an embodiment of a method for donning the dynamic support system 142, shown in FIG. 63, is shown. In some embodiments, the user first locates the dynamic support apparatus 10, shown in FIG. 63, onto their body at 158. Then, at 160, the user activates the control system 18, shown in FIG. 63, indicating that the dynamic support apparatus 10, shown in FIG. 63, has been donned. At 162, the control system 18, shown in FIG. 63, in some embodiments, may inflate the one or more bladders 8028, shown in FIG. 64A, and/or strap actuators 8068, shown in FIG. 64A to the baseline pressure. This baseline pressure may be as discussed above and/or may be any pre-determined pressure from which deflation or inflation may be desired and/or necessary depending on one or more factors, including, but not limited to, user activity. It is the baseline pressure that serves as a "zero" or neutral pressure and from which inflation and deflation is measured.

Figure 66:
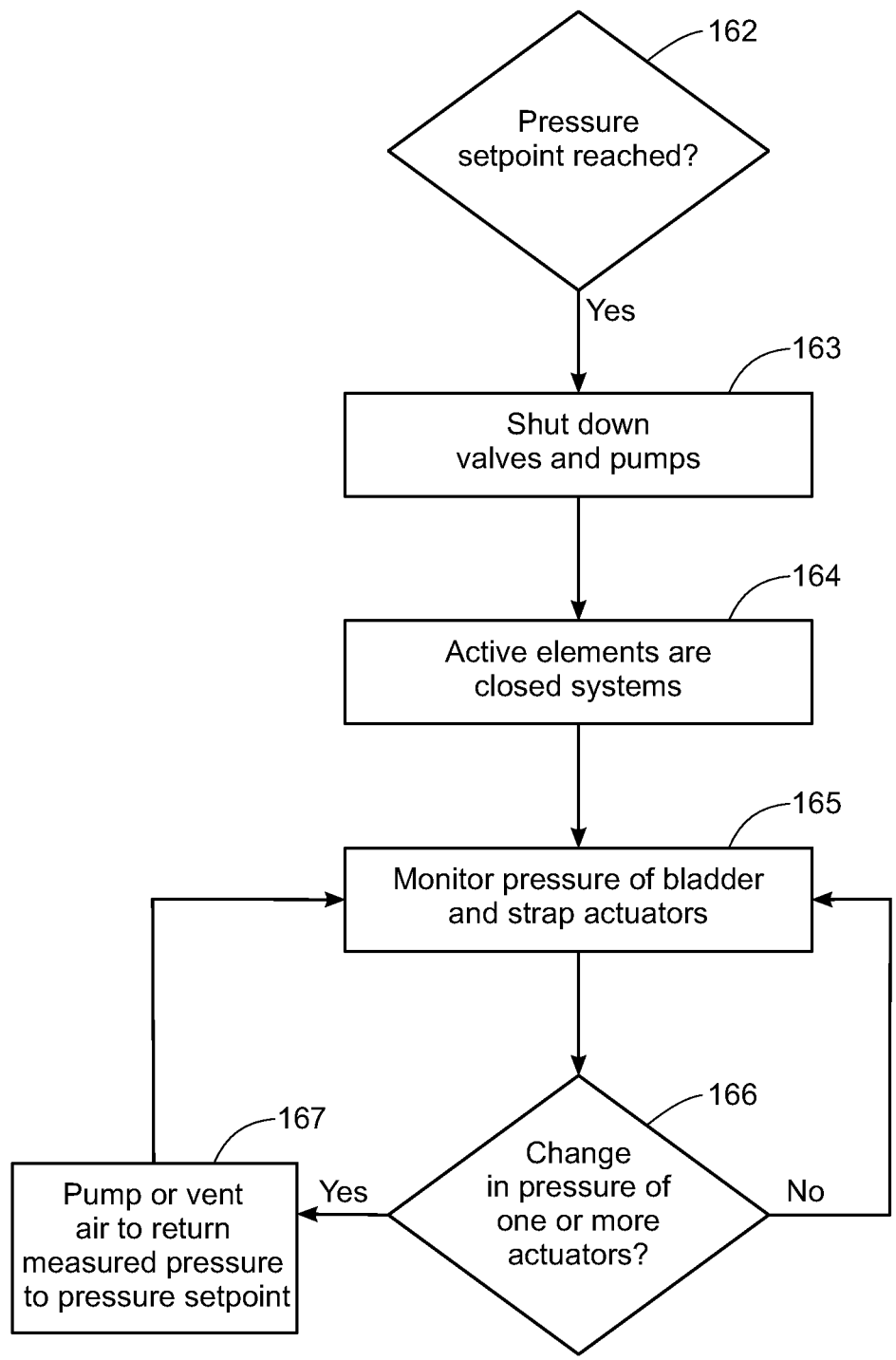
FIG. 66 is a flow diagram of one embodiment of the methods for maintaining the baseline pressure of the one or more actuators.

Referring now to FIG. 66, once the pressure setpoint has been reached at 162, in some embodiments, the control system 18, shown in FIG. 63, may shut-down/close the various valves and pumps at 163. Once the valves and pumps are closed/shutdown, the dynamic interface 16, shown in FIG. 63, becomes a closed system at 164 since, aside from leakage, no air enters or exits the bladders 8028, shown in FIG. 64A, and straps 8068, shown in FIG. 64A. The control system 18, shown in FIG. 63, may then begin a leak compensation mode at 165 for detecting leaks from the closed system maintaining the baseline pressure or the current pressure setpoint in the actuators 8024, e.g. bladders 8028 and/or straps 8068, shown in FIG. 64A.

In various embodiments, the leak compensation mode may include monitoring the pressure of each actuator 8024, shown in FIG. 64A, over time at 165. For example, in some embodiments the control system 18, shown in FIG. 63, may read the pressure of each bladder 8028, shown in FIG. 64A, at pre-determined intervals, e.g., every 0.1 seconds. At 166, the control system 18, shown in FIG. 63, determines whether there has been a change in the pressure of one or more actuators 8024, shown in FIG. 64A. For example, in some embodiments, the control system 18, shown in FIG. 63, may compare the instantaneous pressure of each actuator 8024, shown in FIG. 64A, to the desired setpoint pressure for that actuator 8024, shown in FIG. 64A, at pre-determined intervals (e.g. in one mere exemplary embodiment, every 60 seconds). Where the sampled instantaneous pressure is lower than the desired setpoint pressure, at 167, the control system 18, shown in FIG. 63, may command the pump 8048, shown in FIG. 19B, to add air to that channel in order to increase the pressure in the actuator 8024, shown in FIG. 64A, to the desired setpoint pressure. Conversely, where the sampled instantaneous pressure is greater than the desired setpoint pressure, at 167, the control system 18, shown in FIG. 63, may open the valve 8043, shown in FIG. 19C, associated with the actuator 8024, shown in FIG. 64A, to vent air from the channel in order to decrease the pressure in the actuator 8024, shown in FIG. 64A, to the desired setpoint pressure. In some embodiments, a hysteresis or deadband may be added about the pressure setpoint to provide a range of acceptable pressures about the pressure setpoint where no pumping or venting action is required. This hysteresis or deadband advantageously reduces the amount of work required by the control system 18, shown in FIG. 63, without greatly sacrificing the stability of the prosthesis 11, shown in FIG. 63.

While determining actuator pressures changes by comparing the instantaneous pressure to the desired pressure setpoint may be advantageous in some situations for detecting pressure changes at 166, such as during low activity, in other situations, this control may result in unnecessary air pumping and/or venting. For instance, when the prosthesis 11, shown in FIG. 63, is raised up or carrying a load, the mechanical forces transmitted by the prosthesis 11, shown in FIG. 63, through the dynamic support apparatus 10, shown in FIG. 63, to the user's residual anatomy 12, shown in FIG. 63, will cause the pressure in each channel and actuator 8024, shown in FIG. 64A, to fluctuate with respect to the setpoint pressure. For example, some actuators 8024, shown in FIG. 64A, will undergo compression and have elevated pressures while other actuators will have lower pressures. Thus, if the control system 18, shown in FIG. 63, controls pumping and/or venting based on the instantaneous pressure in these actuators 8024, shown in FIG. 64A, the control system 18, shown in FIG. 63, is likely to add and/or remove air from the actuators 8024, shown in FIG. 64A, unnecessarily.

Therefore, in some embodiments, the control system 18, shown in FIG. 63, may maintain a constant amount (i.e.

mass or mols) of air in each actuator channel, thereby rarely venting and essentially only pumping to make up air lost due to leaking. For example, the control system 18, shown in FIG. 63, may use the monitored pressure over time in each actuator 8024, shown in FIG. 64A, or actuator channel as a proxy measurement to estimate the amount of air in each actuator channel. In using the monitored pressure to estimate the amount of air in each actuator channel, the assumption is made that, on average, the loading on the actuators is constant, which turns out to typically be true, as the user tends to keep the prosthesis 11, shown in FIG. 63, in a neutral, unloaded position near the body and any external loading is transient. Therefore, to estimate the amount of air in each actuator channel, the control system 18, shown in FIG. 63, passes the monitored pressure signal through a low-pass filter 168 (FIG. 67) having a bandwidth sufficiently low to remove most of the pressure transients from the signal. For example, in some exemplary embodiments, the low-pass filter 168 (FIG. 67) may have a bandwidth of less than 0.1 Hz. In other exemplary embodiments, the low-pass filter 168 may have other desired bandwidths. With the pressure transients removed from the pressure signal any remaining variations in the filtered pressure signal should be the result of air leakage from the actuator channel or gradual changes in the shape of the residual anatomy 12, shown in FIG. 63, that result from the wearing of the dynamic support apparatus 10, shown in FIG. 63, changes in temperature and/or other physiological responses. Thus, the control system 18, shown in FIG. 63, may monitor the low-pass filtered pressure signal at 166 and, periodically, supply additional air to the actuators 8024, shown in FIG. 64A, at 172 to account for leaks and the like.

In some embodiments, the control system 18, shown in FIG. 63, may use pulse density modulation control to apply brief pulses of air to each actuator channel to compensate for leakage. Each pulse of air is separated by an idle time between pulses Δt in which air is not being supplied. As the leak rate from a particular actuator channel increases, the time between pulses Δt for that channel is decreased by the control system 18, shown in FIG. 63. When the control system 18, shown in FIG. 63, is in equilibrium, the averaged effect of the air pulses for a particular actuator channel, in various embodiments, should substantially match the effect of air leakage from that actuator channel. The control system 18, shown in FIG. 63, includes control logic for calculating the time between pulses Δt for each actuator channel based on the low-pass filtered pressure measured in that channel. In some embodiments, the control logic for determining the time between pulses Δt may be a function of an error parameter E, e.g. a measurement of how far from the desired pressure setpoint the actuator pressure is. In some embodiments, the function may be exponential and may take the form:

$$\Delta t = f(E) = \Delta t_{max} \cdot \exp(-\alpha \cdot E)$$

where $$\alpha = \frac{1}{E_{max}} \ln\left(\frac{\Delta t_{max}}{\Delta t_{min}}\right);$$

Δt$_{max}$ is a preset maximum allowable time between pulses;
Δt$_{min}$ is a preset minimum allowable time between pulses; and
E$_{max}$ is a preset maximum allowable error.

In this embodiment, when the error parameter E becomes smaller (i.e. approaching zero), the time between pulses Δt should grow towards the maximum time Δt$_{max}$. Conversely, when the error parameter E becomes larger (i.e. approaching the maximum allowable error E$_{max}$) the time between pulses Δt should shrink towards the minimum time Δt$_{min}$. When a particular actuator channel is being supplied air pulses separated by minimum time Δt$_{min}$, the control effort is considered saturated. Although shown as an exponential function, it should be understood by those skilled in the art that the relationship between the time between pulses Δt and the error parameter E could take many forms including a linear function, a quadratic function, a cubic function or any other similar polynomial function. For example, a linear relationship may be represented by the equation:

$$\Delta t = f(E) = \Delta t_{max} = -\frac{E}{E_{max}} \cdot (\Delta t_{max} - \Delta t_{min})$$

Preferably, at the time that the control system 18, shown in FIG. 63, applies one pulse of air, the control system 18, shown in FIG. 63, calculates the time between pulses Δt to the next pulse and schedules the pulse to occur. In embodiments where each actuator channel operates independently, the calculation of Δt may also be performed independently for each channel such that the resulting air pulses occur asynchronously.

Figure 67:
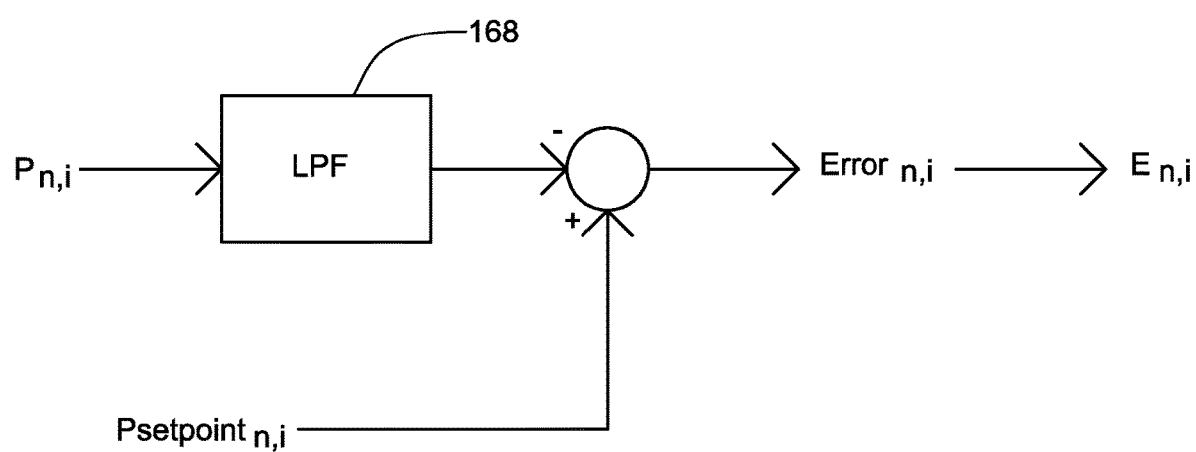
FIG. 67 is a schematic view of an embodiment for a leak detection control mode according to the present invention.

The error parameter E may advantageously be determined in a variety of different ways. Referring to FIG. 67, an embodiment, for determining the error parameter E for a particular channel i at time interval n is shown. In this embodiment, the error parameter E$_{n,i}$ equals an Error$_{n,i}$ calculated from the difference between the pressure setpoint Psetpoint$_{n,i}$ and the monitored pressure P$_{n,i}$ after passing through the low-pass filter 168. In this embodiment, when the monitored pressure P$_{n,i}$ passed through the low-pass filter 168 is lower than the pressure setpoint Psetpoint$_{n,i}$, e.g. due to air leakage from the channel i, the error parameter E$_{n,i}$ is positive.

Figure 68:
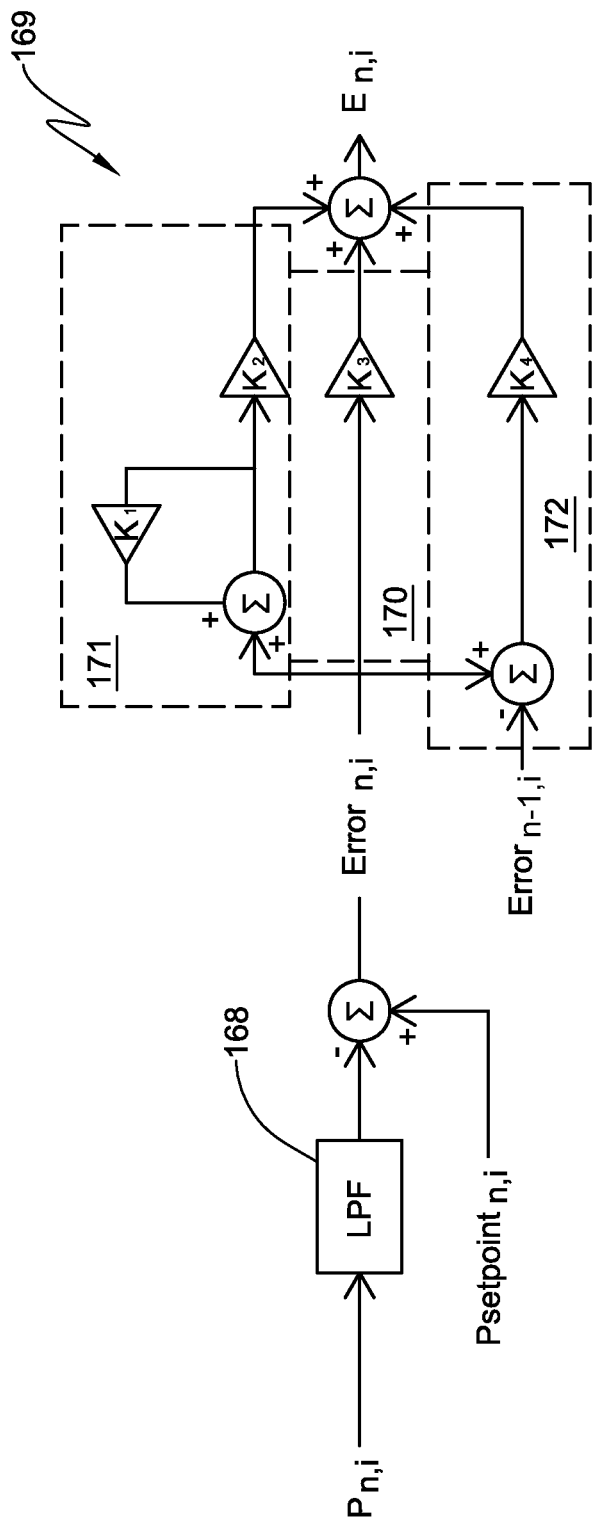
FIG. 68 is a schematic view of another embodiment for the leak detection mode according to the present invention.

Referring to FIG. 68, in some embodiments, the error parameter E for a particular channel i at a given time interval n may be determined by the control system 18, shown in FIG. 63, using a proportional-integral-derivative (PID) control unit 169 having a proportional portion 170, an integral portion 171 and a derivative portion 172. In these embodiments, the control system 18, shown in FIG. 63, first calculates Error$_{n,i}$ from the difference between the pressure setpoint Psetpoint$_{n,i}$ and the monitored pressure P$_{n,i}$ after passing through the low-pass filter 168 in substantially the same manner as that discussed in connection with FIG. 67. The control system 18, shown in FIG. 63, then processes the signal Error$_{n,i}$ through the PID control unit 169 and takes a weighted sum of the output signals from the proportional portion 170, the integral portion 171 and the derivative portion 172 to determine E$_{n,i}$. In the proportional portion 170, Error$_{n,i}$ is multiplied by a gain factor k$_3$, which, in some embodiments, may simply equal 1, to provide a weighted output signal representative of an instantaneous or present error. In the integral portion 171, the control system 18, shown in FIG. 63, calculates the integral of the signal Error$_{n,i}$ over time to provide an output signal representative of the accumulation of past error. The integral portion 171 includes a gain factor k$_1$ that is a leakage factor between 0 and 1 that is applied to the integrated Error$_{n,i}$ with each time step n to prevent the integral output signal from growing without bound. The gain factor $k_1$ may be dependent upon the rate or pressure sampling for the dynamic pressure data. For example, in one exemplary embodiment, provided for mere illustrative purposes, the gain factor $k_1$ may be between 0.93 and 0.99 for a sampling rate of approximately 10 Hz. The output signal from the integral portion 171 is multiplied by a gain factor $k_2$ to provide the weighted output signal representative of past error. In the derivative portion 172, the control system 18, shown in FIG. 63, calculates the derivative of the signal $Error_{n,i}$ by subtracting the $Error_{n-1,i}$ from the previous time step to provide an output signal representative of the rate of change of error, which advantageously provides the control system 18, shown in FIG. 63, with faster response to transients. The output signal from the derivative portion 172 is multiplied by a gain factor $k_4$ to provide the weighted output signal representative of the rate of change of error. The control system 18, shown in FIG. 63, calculates the error parameter $E_{n,i}$ by taking the weighted sum of the output signals from the proportional portion 170, the integral portion 171 and the derivative portion 172. The control system 18, shown in FIG. 63, may use this error parameter $E_{n,i}$ for calculating the time between pulses $\Delta t$ for each actuator channel i as discussed above.

The control logic discussed above advantageously works in the regime where the error parameter E is between and zero (0) and the maximum allowable error $E_{max}$. However, in some situation, the control system 18, shown in FIG. 63, may determine that the error parameter E is outside of that regime. For example, the control system 18, shown in FIG. 63, may determine that the error parameter E exceeds the maximum allowable error $E_{max}$, which would result in the required time between pulses $\Delta t$ to be shorter than the minimum time $\Delta t_{min}$. Therefore, in the situation where the error parameter E exceeds the maximum error $E_{max}$, the control system 18, shown in FIG. 63, turns the pump full on to restore the pressure to the desired setpoint pressure.

In some embodiments, when the control system 18, shown in FIG. 63, implements the control logic discussed above, it is possible that when $\Delta t$ comes due and a pulse of air should be supplied to a particular actuator 8024, shown in FIG. 64A, the instantaneous pressure within the actuator 8024, shown in FIG. 64A, may higher than what the pump 8048, shown in FIG. 19B, can reasonably supply due to transient external loading. Therefore, if the instantaneous pressure is well above the pressure setpoint, the control system 18, shown in FIG. 63, may defer the air pulse briefly until the instantaneous pressure returns to a reasonable level in which the pump 8048, shown in FIG. 19B, may operate.

In some embodiments, when the control system 18, shown in FIG. 63, implements the control logic discussed above, the monitored pressure $P_{n,i}$ after passing through the low-pass filter 168 may be above the target pressure setpoint for a long period of time. This may cause the output signal from the integral portion 171 of the PID control unit 169 to become large and negative. To compensate for this, the control system 18, shown in FIG. 63, may include a pre-defined large and negative threshold for the integral portion that, when surpassed by the output signal, causes the control system 18, shown in FIG. 63, to provide one or more brief pulses of venting, by opening one or more valves 8043, shown in FIG. 19C, to reduce the pressure in the actuator 8024, shown in FIG. 64A, to a level below the target setpoint pressure, which, over time, brings the output signal from the integral portion 171 back toward zero.

It stands to reason that, when the pressure setpoint for a particular channel is higher, the leakage rate from that channel will be higher than for the same channel at a lower pressure setpoint. Therefore, the leak compensation mode described above may advantageously compensate for higher leakage rates by providing uniform pulses of air more frequently when the pressure setpoint for a channel is higher than when the pressure setpoint is lower. Additionally, in some embodiments, the control system 18, shown in FIG. 63, may vary the pulse duration directly with the operating pressure. Thus, when in a higher operating pressure regime, longer pulses may partially or completely compensate for the higher leakage rates. As should be understood by those skilled in the art, the relationship between setpoint pressure and pulse width may be linear, exponential, etc.

In some embodiments of the leak compensation mode, the control system 18, shown in FIG. 63, may advantageously utilize statistics to detect a leaky channel. For example, the control system 18, shown in FIG. 63, may keep track of how many pulses of air are delivered to each channel over a prolonged period of time to determine an average pulse rate for each channel. The control system 18, shown in FIG. 63, may then compare the pulse rates to one or more empirically determined pulse rates calculated based on a nominal system. If the pulse rate for a channel is significantly above the pulse rate for the nominal system, the control system 18, shown in FIG. 63, may identify the channel as leaky. Additionally or in the alternative, the control system 18, shown in FIG. 63, may compare the averaged pulse rate of one channel to the pulse rates of one or more other peer channels to determine whether or not a channel is leaky since, a leaky channel will require a greater number of pulses compared to its peers over a long period of time to maintain a setpoint pressure.

By implementing the control logic for the leak detection mode as discussed above, the control system 18, shown in FIG. 63, is able to advantageously monitor the pressure in actuators 8024, shown in FIG. 64A, and to maintain the baseline pressure or the current pressure setpoint. The leak compensation mode may, in some embodiments, be referred to as a closed-loop system, where monitoring, inflating and deflating may be automatic based on pre-set/pre-determined values, e.g. the baseline pressure, pressure setpoint and/or error threshold. However, in some embodiments, the closed-loop system may be elective by the user and, thus, the user may instead elect to manually inflate/deflate the actuators 8024, shown in FIG. 64A, based, e.g., on recommendations from the control system 18, shown in FIG. 63, and/or based on user desires/requirements.

In some embodiments, the user may indicate to the control system 18, shown in FIG. 63, that they are planning either high-intensity or low-intensity activity, compared with baseline activity. Baseline activity may be that activity which may be performed comfortably and adequately at the baseline pressure.

Figure 69:
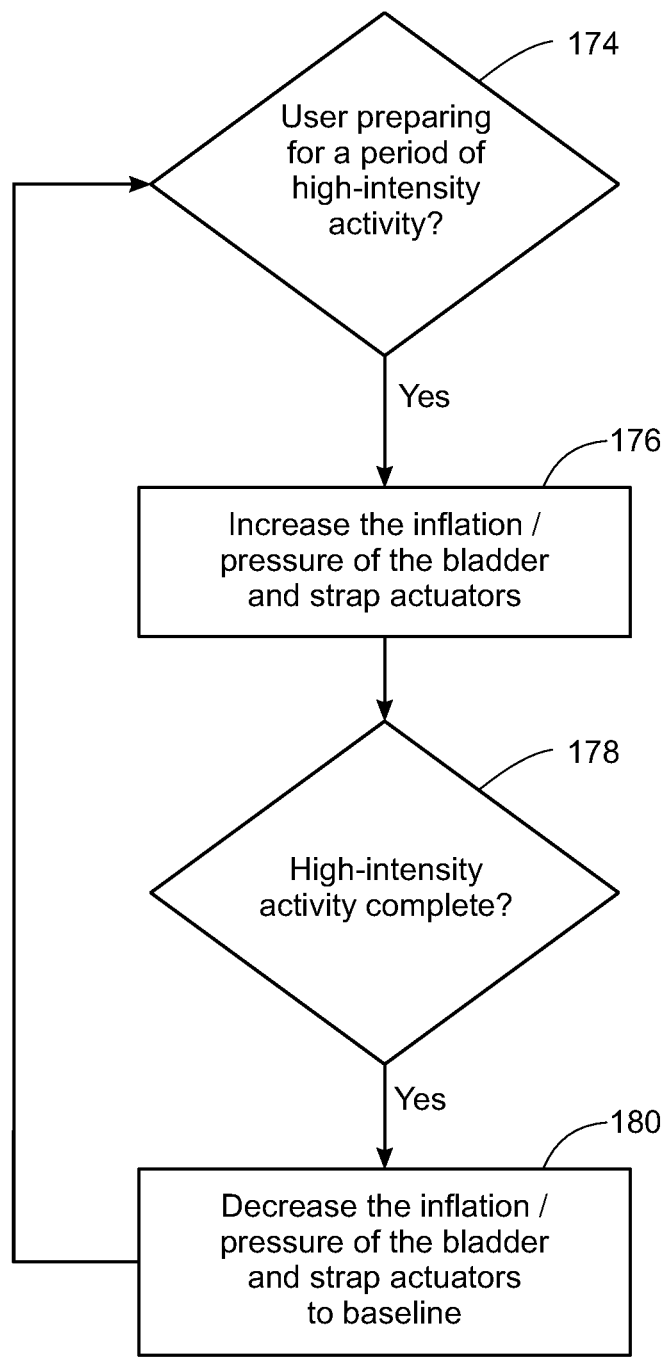
FIG. 69 is a flow diagram of one embodiment of the methods for increasing the pressure of the one or more actuators in preparation for high-intensity activity.

Referring to FIG. 69, the user may indicate to the control system 18, shown in FIG. 63, that they are preparing for high-intensity activity (e.g., using a button or navigating through a menu or the like) at 174. The control system may then inflate/increase the pressure setpoint of one or more actuators 8024, shown in FIG. 64A, e.g. bladders 8028 and strap actuators 8068, shown in FIG. 64A, at 176 to a high pressure setting. The high pressure setting, in some embodiments, provides a greater degree of fixation, i.e., more tightly coupling the dynamic support apparatus 10, shown in FIG. 63, to the user. This increased fixation may allow increased usability of the prosthetic device 11, shown in FIG. 63, which may be desired for high-intensity activities, for example, but not limited to, lifting a gallon of milk to a high shelf and/or carrying heavy loads. The user may then indicate to the control system 18, shown in FIG. 63, that the high-intensity activity is complete (e.g., using a button or navigating through a menu or the like) at 178. Once the user indicates that high-intensity activity is complete, the control system 18, shown in FIG. 63, may decrease the inflation/pressure of one or more actuators 8024, shown in FIG. 64A, e.g. bladders 8028 and strap actuators 8068, shown in FIG. 64A, at 180 to return to the baseline pressure.

Figure 70:
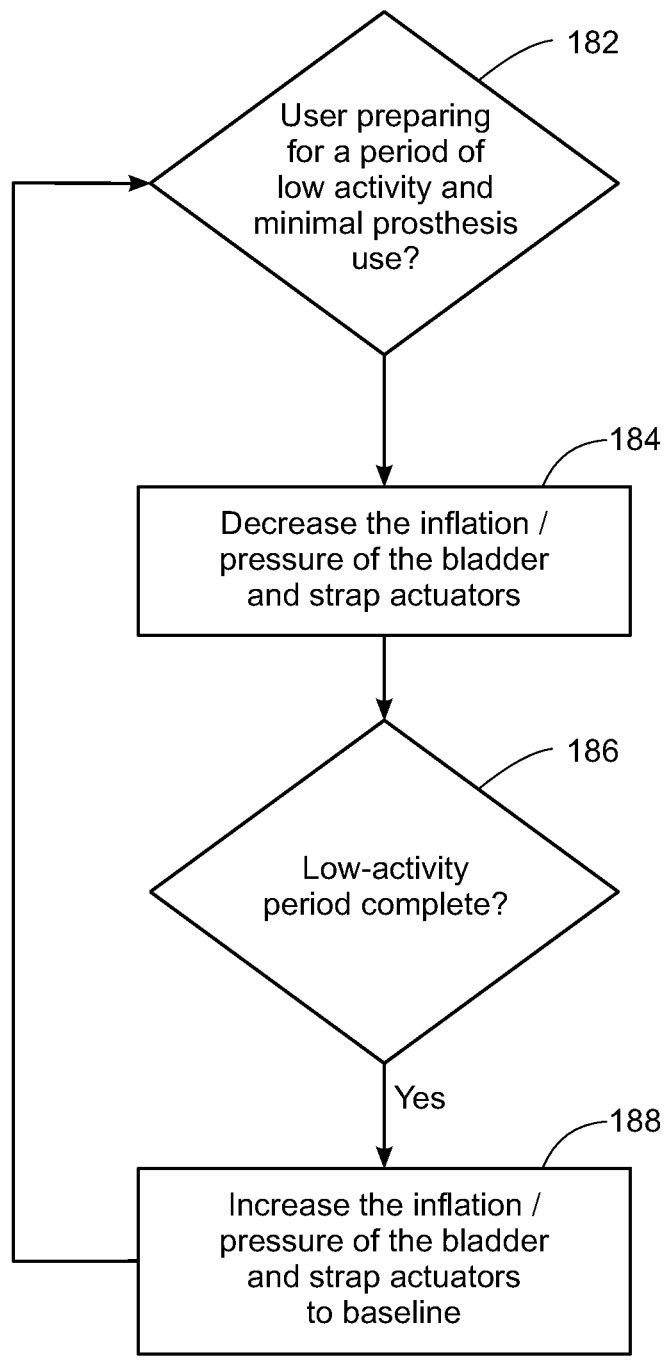
FIG. 70 is a flow diagram of one embodiment of the methods for decreasing the pressure of the one or more actuators in preparation for low-intensity activity.

Referring to FIG. 70, in some embodiments, the user may similarly indicate to the control system 18, shown in FIG. 63, that they are preparing for low-intensity activity (e.g., using a button or navigating through a menu or the like) at 182. The control system may then deflate/decrease the pressure setpoint of one or more actuators 8024, shown in FIG. 64A, e.g. bladders 8028 and strap actuators 8068, shown in FIG. 64A, at 184 to a low pressure setting. Thus, the user is able to command the control system 18, shown in FIG. 63, to decrease pressure in the actuators 8024, shown in FIG. 64A, when the user expects a period of time where their activity will be low, i.e., the prosthetic device 11, shown in FIG. 63, may be in minimal use. In some embodiments, the low pressure setting may provide for a relaxed interface fit of the dynamic support apparatus 10, shown in FIG. 63, without requiring the user to completely doff the dynamic support apparatus 10, shown in FIG. 63. The user may then indicate to the control system 18, shown in FIG. 63, that the low-intensity activity is complete (e.g., using a button or navigating through a menu or the like) at 186. Once the user indicates that the low-intensity activity is complete, the control system 18, shown in FIG. 63, may increase the inflation/pressure of one or more actuators 8024, shown in FIG. 64A, e.g. bladders 8028 and strap actuators 8068, shown in FIG. 64A, at 188 to return to the baseline pressure. In some embodiments, the user may transition directly from low-activity to high-activity, and vice-versa, by indicating "high" activity while in the low-activity setting, and vice-versa, (e.g., using a button or navigating through a menu or the like). In these embodiments, the control system 18, shown in FIG. 63, responds as discussed above by inflating the actuators 8024, shown in FIG. 64A, to a high pressure setting to prepare for high-activity or by decreasing the actuator pressure to a low pressure setting to prepare for low-activity.

Referring back to FIG. 64A, in some embodiments, the control system 18, shown in FIG. 63, may infer the user's activity level based on the time history of operating pressures in the various actuators 8024 (e.g. bladders 8028 and straps 8068) that are being monitored by the control system 18, shown in FIG. 63. When the control system 18, shown in FIG. 63, infers that the user is engaged in heavy activity, it may automatically increase one or more pressure setpoints of one or more actuators 8024 to improve the fit of the prosthetic support apparatus 8010. Similarly, when the control system 18, shown in FIG. 63, infers that the user is engaged in low or no activity, it may automatically decrease one or more pressure setpoints of one or more actuators 8024 to relax the fit of the prosthetic support apparatus 8010. Thus, the control system 18, shown in FIG. 63, may advantageously permit the prosthetic support apparatus 8010 to engage the user less tightly than a conventional prosthetic support during a majority of time when the prosthesis 11, shown in FIG. 63, is not being actively used, but tightly engage the user during those times when it is necessary due to increased activity.

To infer the user's activity level, in some embodiments, the control system 18, shown in FIG. 63, may determine variability in the operating pressures in the actuators 8024 using the pressure time history for the actuators 8024. To determine the variability, the control system 18, shown in FIG. 63, may include a high-pass filter (not shown) through which the pressure time history may be processed. Applying a high-pass filter (not shown) to the pressure time history, with a low bandwidth, removes the steady-state (i.e. DC) pressure data and reveals the dynamic (i.e. AC) pressure data in the signal. This dynamic pressure data is largely the result of external loading transients from motion of the prosthesis 11, shown in FIG. 63, and load-carrying, which is indicative of the user's activity level. For computational efficiency, in some embodiments, the high-pass filter (not shown) may be realized using the low-pass filter 168, shown in FIG. 68, and discussed above in connection with the leak compensation mode. To obtain the dynamic pressure data using the low-pass filter 168, shown in FIG. 68, the control system 18, shown in FIG. 63 may subtract the low-passed filtered pressure signal from the unfiltered pressure signal.

The control system 18, shown in FIG. 63, may take the absolute value of this dynamic pressure data and compare it to a reference pressure that represents the pressure variability for the user engaging in a typical, moderate level of activity. When the magnitude of the absolute value of the dynamic data is below this reference pressure, the control system 18, shown in FIG. 63, infers that the user is engaged in low or no activity. When the magnitude of the absolute value of the dynamic data is above this reference pressure, the control system 18, shown in FIG. 63, infers that the user is active. In some embodiments, the control system 18, shown in FIG. 63, affects the comparison to the reference pressure by calculating a conditioned pressure by subtracting the reference pressure value from the absolute value of the dynamic data. The control system 18, shown in FIG. 63, may then determine whether the resulting conditioned pressure is greater than zero to evaluate whether the user is engaged in activity.

In some embodiments, the control system 18, shown in FIG. 63, may augment the activity reference pressure with a deadband that defines typical or moderate activity as a range of pressures, rather than just a single pressure. In these embodiments, the control system 18, shown in FIG. 63, sets the conditioned pressure to zero if it falls within the deadband range and infers activity only when the conditioned pressure is greater than zero, i.e. above an upper limit of the deadband range. Likewise, the control system 18, shown in FIG. 63, may infer inactivity only when the conditioned pressure is less than zero, i.e. below a lower limit of the deadband range. The deadband may be symmetric about the activity reference pressure, asymmetric about the activity reference pressure or may extend only on one side of the activity reference pressure or the other. The deadband advantageously allows the control system 18, shown in FIG. 63, to set a range of dynamic pressure that is considered ordinary or expected, with only measurements outside of the deadband range being considered either as activity or inactivity. In some embodiments, rather than defining the deadband as existing about the activity reference pressure, the control system 18, shown in FIG. 63, may instead simply define the deadband as existing between the a high activity reference pressure and a low activity reference pressure.

While the determination of activity or inactivity may be made by the control system 18, shown in FIG. 63, from a single pressure reading, in most embodiments, the determination is preferably based on a trend of activity or inactivity over many pressure readings as observed in time, for example, at time intervals n. To make the determination, the control system 18, shown in FIG. 63, may include an accumulator (not shown) for each actuator channel i. The control system 18, shown in FIG. 63, increases the accumulator for a given actuator channel i whenever the control system 18, shown in FIG. 63, infers activity for that actuator channel i at time interval n, and decreases the accumulator whenever inactivity is inferred at the time interval n. The control system 18, shown in FIG. 63, calculates a global activity metric by taking an average of the accumulators (not shown), across all actuator channels i, which provides a global measure of user activity or inactivity. When the global activity metric exceeds some predetermined positive activity threshold, the control system 18, shown in FIG. 63, concludes that the user is engaged in activity and has been so for some time. Upon such a determination, the control system 18, shown in FIG. 63, may automatically increase the pressure setpoint of one or more of the actuators 8024 to tighten the fit of the dynamic support apparatus 8010. Conversely, if the global activity metric becomes less than a predefined negative activity threshold, the control system 18, shown in FIG. 63, concludes that the user has been in a prolonged period of inactivity. Upon such a determination, the control system 18, shown in FIG. 63, may automatically decrease one or more of the pressure setpoint(s). After making a change to one or more of the pressure setpoints, the control system 18, shown in FIG. 63, resets all of the accumulators (not shown) back to zero and restarts the monitoring process.

In some embodiments, rather than only accumulating time spent above and below the activity reference, the control system 18, shown in FIG. 83, may instead calculate an activity metric for each actuator channel i by integrating the conditioned pressure in time. Taking the integral of the conditioned pressure allows the control system 18, shown in FIG. 63, to take into account not only whether the conditioned pressure in each actuator channel i is positive or negative, but also the extent to which the activity metric is above or below the activity reference pressure. Therefore, in these embodiments, large and prolonged excursions from the activity reference pressure in an actuator channel i are weighted more heavily than small perturbations in the control system's determination of activity and/or inactivity. Accordingly, the positive activity thresholds would be crossed much sooner in response to heavy activity than in embodiments where the control system 18, shown in FIG. 63, only accumulates time spent above and below the activity reference, as discussed above. The time integral of the conditioned pressure has a leakage factor $k_{leak}$, which ranges from 0 to 1, applied to it to continually force the activity metric towards zero from both the positive and negative directions. This leakage factor $k_{leak}$ will, in essence, provide the accumulated history with a limited memory, and prevent the integral term from growing without bound. The gain factor $k_{leak}$ may be dependent upon the rate or pressure sampling for the dynamic pressure data. For example, in one exemplary embodiment, provided for mere illustrative purposes, the gain factor $k_{leak}$ may be between 0.93 and 0.99 for a sampling rate of approximately 10 Hz.

In some embodiments, rather than using the single activity metric for the determination of both activity and inactivity, the control system 18, shown in FIG. 63, may divide the determination into two separate metrics based on whether the conditioned pressure is positive or negative. For example, a positive conditioned pressure would increase the activity metric, which would, therefore, be based on the time integral of only positive conditioned pressures. A negative conditioned pressure would, instead, be used to increase an inactivity metric based on the time integral of only negative conditioned pressures. In these embodiments, the gain factor $k_{leak}$ may be applied to both the activity metric and the inactivity metric.

The control system 18, shown in FIG. 63, may calculate the global activity metric by taking an average of the activity metrics, across all actuator channels i, to provide the global measure of user activity. Similarly, the control system 18, shown in FIG. 63, may calculate a global inactivity metric by taking an average of the inactivity metrics, across all actuator channels i, to provide the global measure of inactivity. In a manner similar to that discussed above, the control system 18, shown in FIG. 63, may conclude that the user is engaged in sustained activity when the global activity metric exceeds some predetermined activity threshold. Upon such a determination, the control system 18, shown in FIG. 63, may automatically increase the pressure setpoint of one or more of the actuators 8024 to tighten the fit of the dynamic support apparatus 8010. Similarly, the control system 18, shown in FIG. 63, may conclude that the user has been in a prolonged period of inactivity if the global inactivity metric passes some predefined inactivity threshold. Upon such a determination, the control system 18, shown in FIG. 63, may automatically decrease one or more of the pressure setpoint(s).

Splitting the global activity metric into separate global activity and inactivity metrics allows the control system 18, shown in FIG. 63, to be more responsive to user activity than with the single global activity metric. For example, with only the single global activity metric, a prolonged period of inactivity that does not exceed the inactivity threshold must be overcome by user activity to first bring the global activity metric back from a large and negative value, through zero, and on up to the activity threshold in order for activity to be detected. With the separate activity and inactivity metrics, during a prolonged period of inactivity, the activity metric will be clamped at zero. Thus, if a user then begins a period of heavy activity, the activity threshold will be crossed much sooner because the activity metric may begin to grow immediately independently of how long the user engaged in activity, thereby providing for improved activity detection. Simultaneously, the inactivity metric may advantageously be decayed back toward zero. Thus, separate activity and inactivity metrics advantageously allow the control system 18, shown in FIG. 63, to be programmed to require a concerted and sustained period of activity or inactivity to reach either threshold for changing the inflation pressure setpoint. Additionally, the split activity and inactivity metrics allow the control system 18, shown in FIG. 63, to be tuned to be more immune to pressure perturbations caused by pulse density modulation, discussed above, which appear to the control system 18, shown in FIG. 63, as user activity in the dynamic pressure data.

Referring back to FIG. 63, in other embodiments, the control system 18 may estimate user activity directly from information obtained from the prosthesis 11. For example, using its own sensors (not shown), the prosthesis 11 can estimate the load being applied to one or more of its joints.

In some embodiments, a load cell (not shown) installed at an interface between the dynamic support apparatus 10 and the prosthesis 11 may measure an aggregate load that is being transferred from the prosthesis 11 to the residual anatomy 12 through the dynamic support apparatus 10. The control system 18 may estimate user activity, at least in part, upon the measured aggregate load. For example, the aggregate load measurements may be transmitted to the control system 18, e.g. through wireless data transmission, and the control system 18 may analyze that data to infer the user's activity level. In some embodiments, the control system 18 may calculate the time-derivative of the forces, wherein a large time-derivative of force indicates a load that is rapidly changing and a small time-derivative of force indicates a load that is not changing. The control system 18 may process this information in a manner similar to the pressure time history, as described above, to produce either a single global activity metric or split activity and inactivity metrics, as discussed above. These metrics may be used by the control system 18 in substantially the same manner as the pressure-based metrics discussed above to determine whether to increase or decrease one or more pressure setpoints.

Although described separately for simplicity, in some embodiments, the pressure-based activity and inactivity metrics from each actuator channel i may be combined with the metrics produced from load data obtained from the prosthesis 11 and/or from measurement of the aggregate loading at the interface between the prosthesis 11 and the dynamic support apparatus 10. For instance, in some embodiments, the metrics may be combined as a weighted sum, and the combined result used in determining whether to increase or decrease one or more pressure setpoints.

In some embodiments, the control system 18 may have one or more biasing mechanisms to ensure that, having made a change to one or more pressure setpoints in one direction (e.g. increasing or decreasing), the next change in that same direction is less likely. The one or more biasing mechanisms ensure that a small twitch while at a low inflation setting, which the control system 18 may characterize as high activity, does not quickly result in the dynamic support apparatus 10 being inflated to its maximum amount.

In some embodiments, as the biasing mechanism, the control system 18 may adjust the activity reference pressure directly with pressure setpoint. For example, when the dynamic support apparatus 10 is at a high inflation state, it should be because the user is engaged in higher activity, such as carrying a heavier load. In such a situation, one would expect a greater dynamic pressure content commensurate with that higher activity. Therefore, when the dynamic support apparatus 10 is at a high inflation state, the control system 18 may increase the activity reference pressure, since the activity reference pressure is a measure of what is a typical activity level. Thus, the control system 18 may use the biasing mechanism to discount the activity that is detected when at higher pressures, while simultaneously making inactivity more pronounced. Similarly, when the dynamic support apparatus 10 is at a low inflation state, the biasing mechanism will tend to amplify the effect of even moderate activity. The biasing mechanism may provide a linear relationship between the activity reference pressure and the inflation state or may provide some other desired relationship.

In some embodiments, the control system 18 may change the activity threshold and inactivity threshold with pressure setpoint as the biasing mechanism. In these embodiments, the control system 18 will typically adjust the activity and inactivity thresholds in concert, i.e. both raising or lowering together, though not necessarily by the same magnitude. For instance, when the dynamic support apparatus 10 is at a high inflation state, the activity threshold may be much higher than when the dynamic support apparatus 10 is at a low inflation state. The separation between the activity and inactivity thresholds may be constant across the whole inflation range or, in some embodiments, may be varied by the control system 18. This biasing mechanism may also provide a linear relationship between the activity and inactivity thresholds and the inflation state or may provide some other desired relationship. Thus, the control system 18 is able to advantageously alter the size of the deadband range within which dynamic pressure changes are considered normal activity. For example, in one illustrative embodiment, the deadband range may narrow and approach zero at a low inflation state, but may rise and broaden at higher inflation levels.

In some embodiments, the control system 18 may alter the deadband applied in determining the activity and inactivity metrics as the biasing mechanism. For example, at a low inflation state, the control system 18 may reduce the upper deadband threshold and may increase the lower deadband threshold. Conversely, at a high inflation state, the control system 18 may increase the upper deadband threshold, while reducing the lower deadband threshold. The total width of the deadband range may be constant across the whole inflation range, or may be varied by the control system 18. Although these biasing mechanisms have been described separately for simplicity, those knowledgeable in the art should recognize that the biasing mechanism could also be any combination of those discussed above.

Thus, the control system 18 may advantageously automatically adjust to an appropriate pressure setting for a current level of activity and may maintain that pressure setting until a change in the level of activity is detected. Additionally, by detecting inactivity in addition to activity, the pressure setpoints may be reduced by a pre-determined amount after a period of inactivity so that the control system 18 has a tendency to minimize the amount of pressure applied by the dynamic support apparatus 10 to the user, thereby improving user comfort and preventing adverse affects to the user's tissue contacted by the dynamic support apparatus 10.

Figure 71:
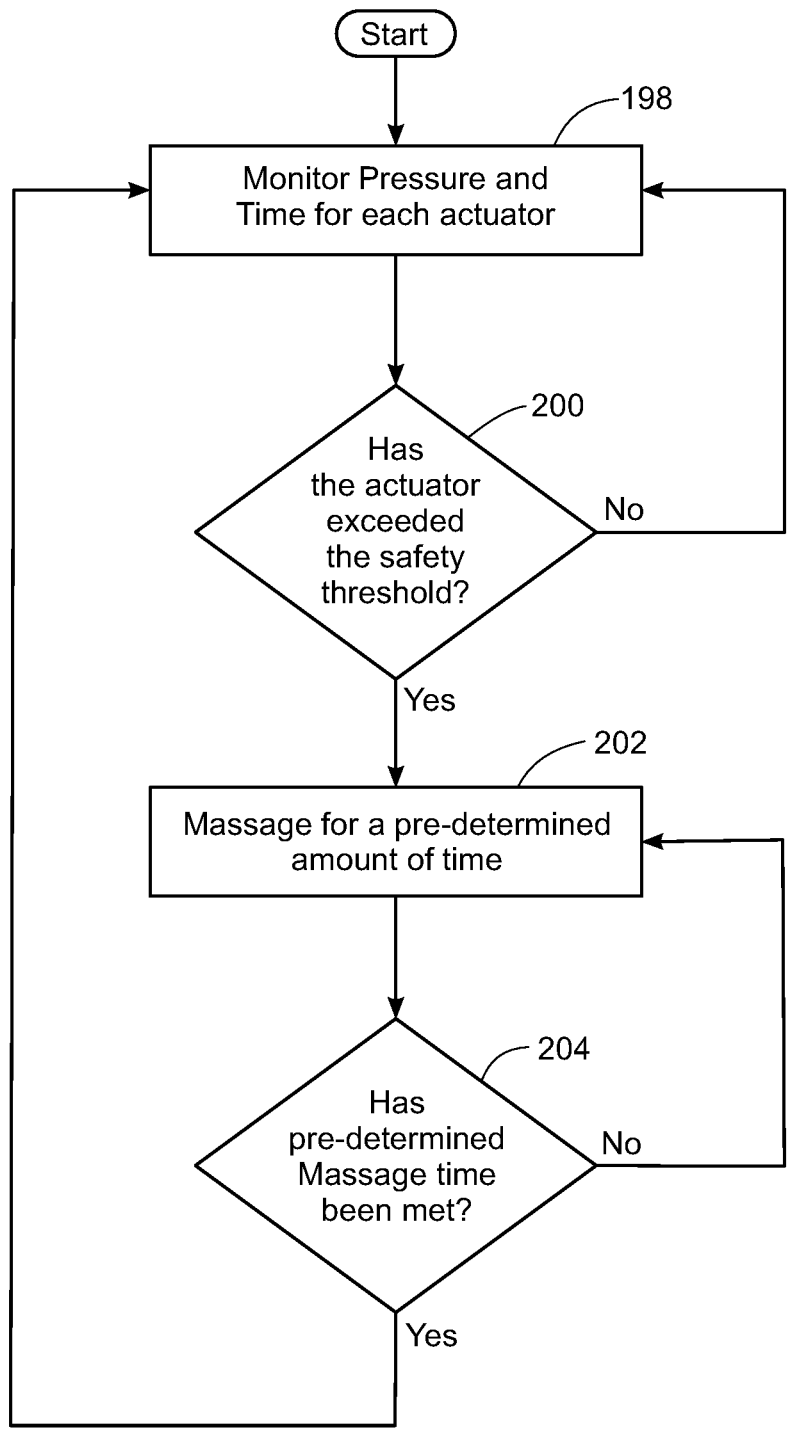
FIG. 71 is a flow diagram of one embodiment of a method for auto-relief according to the present invention.

Referring to FIG. 71, in some embodiments, the control system 18, shown in FIG. 63, may also include an auto-relief system in the leak compensation mode to ensure the one or more actuators 8024, shown in FIG. 64A, e.g. bladders/straps, are not at a high pressure for so long a time that the user's tissue may be adversely affected, for example, where the user's tissue may experience inadequate blood supply or circulation to a local region secondary to blockage of blood vessels to that region. Thus, at 198, the control system 18, shown in FIG. 63, monitors the pressure in one or more actuators 8024, shown in FIG. 64A, as discussed above. The control system 18, shown in FIG. 63, then evaluates whether the monitored pressure exceeds a pre-determined safety threshold at 200. In some embodiments, the safety threshold may be a function of time and pressure, for example, by comparing an integral of the monitored pressure to the safety threshold, thereby accounting for both the magnitude of and duration at an elevated pressure. If the control system 18, shown in FIG. 63, determines that the monitored pressure of one or more actuators 8024, shown in FIG. 64A (e.g. bladders/straps) exceeds the safety threshold at 200 (e.g. in some combination of magnitude and duration), that actuator 8024, shown in FIG. 64A, is identified by the control system 18, shown in FIG. 63, and the control system 18, shown in FIG. 63, automatically starts an auto-relief mode at 202 to alleviate the pressure on the tissue.

For example, where any one or more bladders 8028, shown in FIG. 64A, and/or straps 8068, shown in FIG. 64A, has been maintained at a high-pressure for a long period of time (e.g., longer than a pre-set period of time that may be considered acceptable for user health), this bladder 8028, shown in FIG. 64A, and/or strap 8068, shown in FIG. 64A, may be determined to have exceeded the safety threshold by the control system 18, shown in FIG. 63. The control system 18, shown in FIG. 63, may then enter into the auto-relief mode at 202 for a pre-determined amount of time. In the auto-relief mode, the control system 18, shown in FIG. 63, may vent the identified bladder 8028, shown in FIG. 64A, and/or strap 8068, shown in FIG. 64A, to a lower pressure for a pre-determined amount of time followed by partial re-inflation of the identified bladder 8028, shown in FIG. 64A, and/or strap 8068, shown in FIG. 64A, for a pre-determined amount of time which may, in some embodiments, encourage perfusion of the user's tissue.

Once the control system 18, shown in FIG. 63, determines that the auto-relief criteria has been met at 204, the control system 18, shown in FIG. 63, may return the bladder 8028, shown in FIG. 64A, and/or strap 8068, shown in FIG. 64A, to the pressure/inflation level at which it was before the auto-relief mode was initiated. In some embodiments, the control system 18, shown in FIG. 63, may limit the auto-relief mode to one bladder 8028, shown in FIG. 64A, and/or strap 8068, shown in FIG. 64A, at any one time. This may advantageously maintain stability of the dynamic support apparatus 10, shown in FIG. 63, so that the user may continue regular activity during the auto-relief mode with minimum negative effect.

Although the auto-inflate/auto-deflate and auto-relief systems have been described separately herein for simplicity, it should be understood by those skilled in the art that the auto-inflate/auto-deflate system and the auto-relief system, as well as other control systems, may be combined and integrated into the leak compensation mode discussed above for improved functionality.

In some embodiments, the control system 18 for the dynamic support system 142, shown in FIG. 63, may be configured using a software application through, for example, a personal computer. In some embodiments, using this software application, the number and types of actuators 8024, shown in FIG. 64A, may be configured along with their operating pressures. The software application may be, in some embodiments, used to configure user inputs, for example, whether integral to the control unit 8052, or remote, for controlling operation of one or more features of the dynamic support system 142, shown in FIG. 63. System faults may also be diagnosed through the software application. In some embodiments, the software application may be used by prosthetists as part of the fitting process for the dynamic support apparatus 10, shown in FIG. 63. In some embodiments, the software application, or another software application, may be used by the user to update the settings of the dynamic support system 142, shown in FIG. 63, and/or to reprogram/re-assign the user inputs to the elected functionality.

In some embodiments, the user may indicate to the control system 18, shown in FIG. 63, for example, in some embodiments, by pressing a button or otherwise navigating through a menu using the control unit 8052, shown in FIG. 64A, that the user is preparing to doff the dynamic support apparatus 10, shown in FIG. 63. In some embodiments, the control system 18, shown in FIG. 63, may then deflate/eliminate pressures from the bladders 8028, shown in FIG. 64A and/or straps 8068, shown in FIG. 64A. The reduced fixation from deflating the bladders 8028, shown in FIG. 64A and/or straps 8068, shown in FIG. 64A, increases the ease with which the user may doff the dynamic support apparatus 10, shown in FIG. 63. In some embodiments, following doffing, the user may attach the control unit 8052, shown in FIG. 64A, to a charger or may otherwise charge the control unit 8052, shown in FIG. 64A, using wireless charging and/or replacing the batteries/power source.

Figure 72:
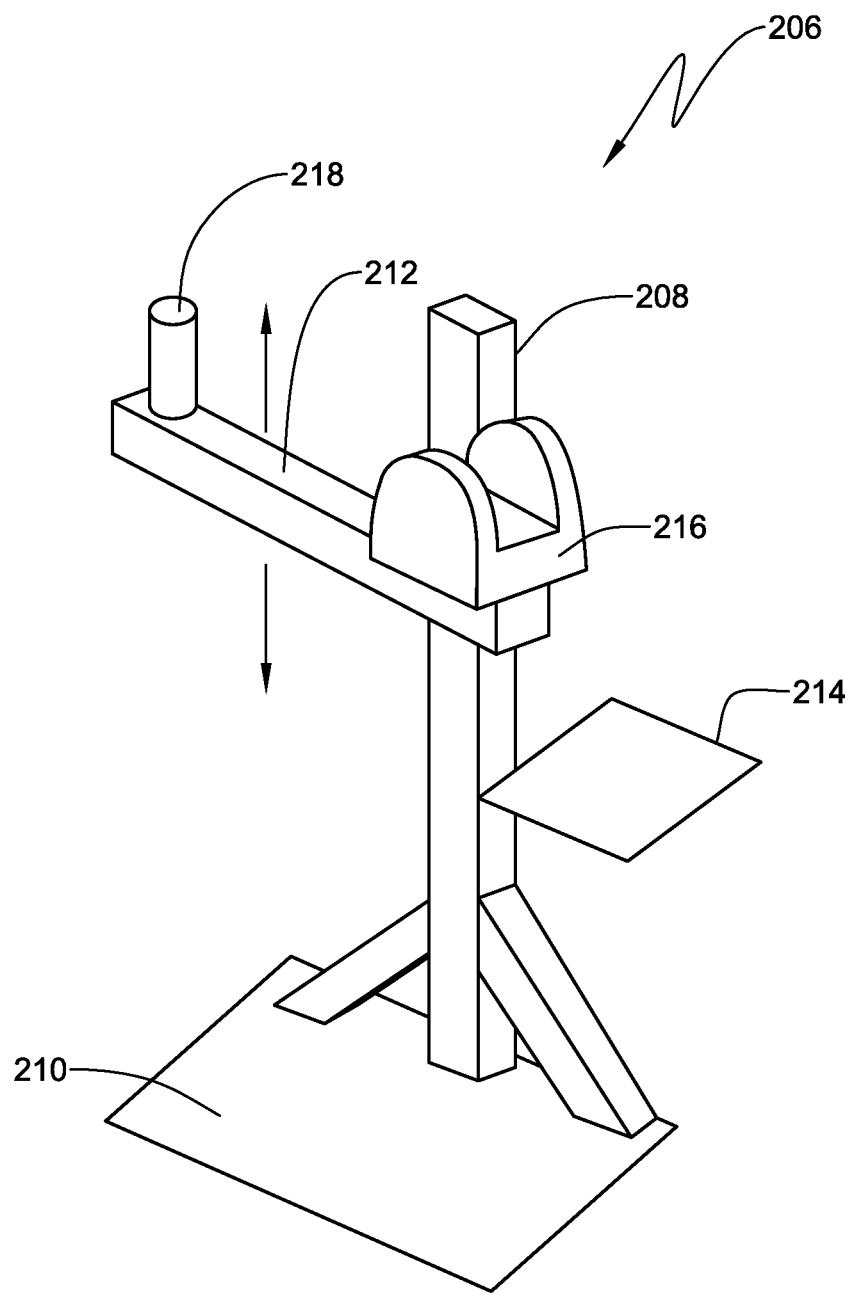
FIG. 72 is an embodiment of a donning stand according to another aspect of the present invention.

Referring to FIG. 72, according to some embodiments, a donning stand 206 may be provided to facilitate donning and doffing of the dynamic support apparatus 10, shown in FIG. 63, with the prosthetic device 11, shown in FIG. 63, attached thereto. The donning tree 206 includes a vertical tower 208 with a base 210 at its lower end for contacting an underlying surface and for supporting the vertical tower 208 in an upright position. The vertical tower 208 has a substantially horizontal arm support 212 adjustably coupled thereto such that a height of the arm support 212 from the base 210 may be adjusted by moving the arm support 212 along at least a portion of a length of the vertical tower 208. Once a desired height is reached, the arm support 212 may be locking in position by a securing mechanism (not shown). The vertical tower 208 also includes a recharging tray 214 coupled thereto for supporting and charging one or more batteries of the control system 18, shown in FIG. 63, of the dynamic support apparatus 10, shown in FIG. 63, and/or of the prosthetic device 11, shown in FIG. 63. The recharging tray 214 may include one or more charging outlets (not shown) or may include a wireless charging pad for charging one or more batteries simultaneously. The arm support 212 includes an elbow yoke 216 at its end proximate the vertical tower 208 and a handle 218 at its distal end. The elbow yoke 216 is configured to accommodate an elbow (not shown) of the prosthetic device 11, shown in FIG. 63, and, in some embodiments, may be configured to accommodate the elbow (not shown) in a particular configuration, such as an elbow actuated to approximately 90 degrees of flexion. The handle 218 is positioned such that, when the prosthetic elbow (not shown) is positioned in the elbow yoke 216, a prosthetic hand (not shown) of the prosthetic device 11, shown in FIG. 63, may wrap naturally around the handle and grip it.

In operation, the height of the arm support 212 of the donning stand 206 may advantageously be adjusted to accommodate a particular user. Once adjusted to the desired height, the user may doff the prosthetic arm 11, shown in FIG. 63, and the dynamic support apparatus 10, shown in FIG. 63, on the donning stand 206 by positioning the prosthetic elbow (not shown) in the elbow yoke 216 and gripping the prosthetic hand (not shown) to the handle 218. The user may then remove the dynamic support apparatus 8010, shown in FIG. 64A, which is supported by the donning stand 206 through the prosthetic device 11, shown in FIG. 63. The user may also store accessories, such as the control unit 8052, shown in FIG. 64A, of the dynamic support 8010, shown in FIG. 64A, on the recharging tray 214 to recharge said accessories. Thus, advantageously, if the user employs the donning stand 206 for supporting the prosthetic device 11, shown in FIG. 63, and the dynamic support apparatus 10, shown in FIG. 63, overnight, the prosthetic device 11, shown in FIG. 63, and the dynamic support apparatus 10, shown in FIG. 63, remain pre-positioned on the donning stand 206 for optimal donning in the morning. Additionally, the recharging tray 214 will recharge the batteries of the prosthetic device 11, shown in FIG. 63, and/or the dynamic support apparatus 10, shown in FIG. 63, so that each are ready for use the next morning.

Figure 78A:
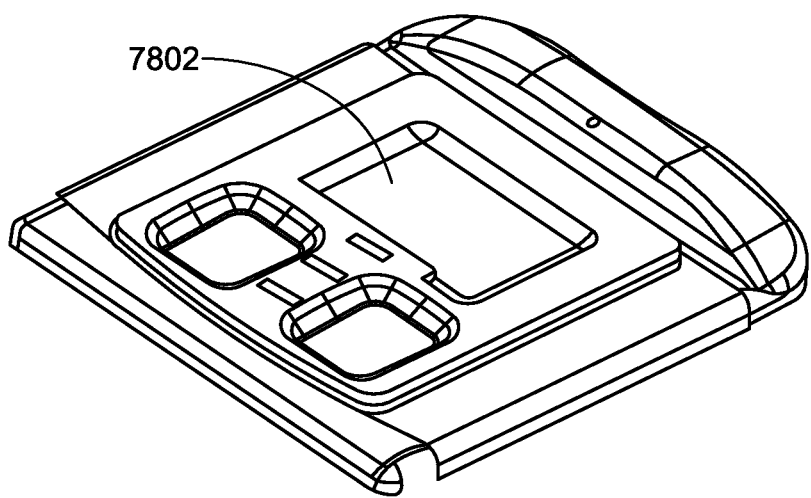
FIGS. 78A-78C show various views of an embodiment of a recharging tray.
Figure 78B:
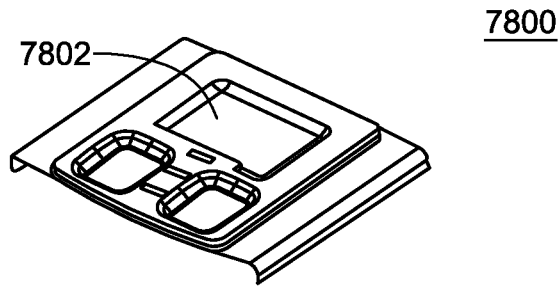
Figure 78C:
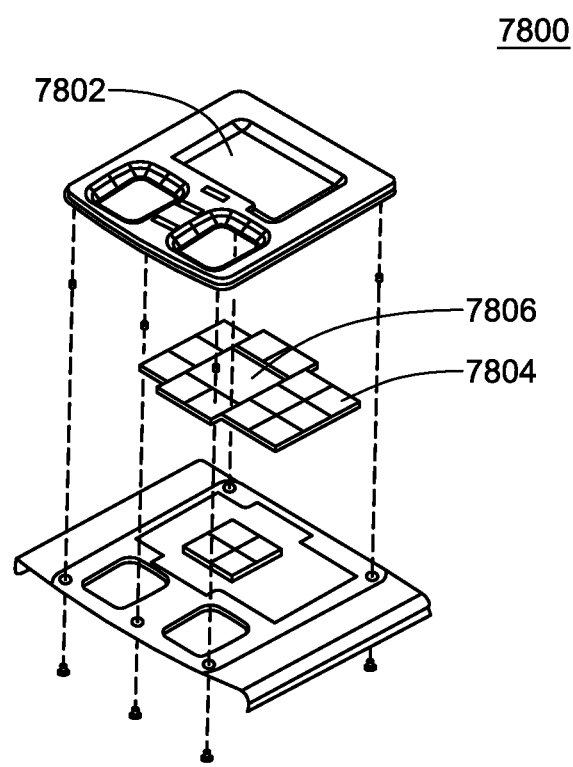

In some embodiments of the control unit, the battery may be, as discussed above, rechargeable. In some embodiments, a Litz wire coil is used for recharging the battery. The Litz wire coil is located in the control unit. As discussed above, in some embodiments, a recharging tray may be used for wirelessly recharging the control unit. However, in some embodiments, where the Litz wire coil and wireless recharging is used, another embodiment of the recharging tray may be used. Referring now to FIGS. 78A-78C, an embodiment of a recharging tray 7800 is shown. In the embodiment shown, the recharging tray 7800 includes a preformed control unit section 7802 to accommodate the various embodiments of the control unit 8052 for recharging. In some embodiments, a ferrite shield 7804 is included to shield the areas around the Litz wire coil which is located, in the embodiment shown, in the Litz wire coil area 7806. This recharging tray 7800 system may be desirable to prevent over-heating of components within the control unit while allowing recharging using a Litz wire coil. In some embodiments, the control unit may be recharged via USB or other wired charging system/device.

Figure 77C:
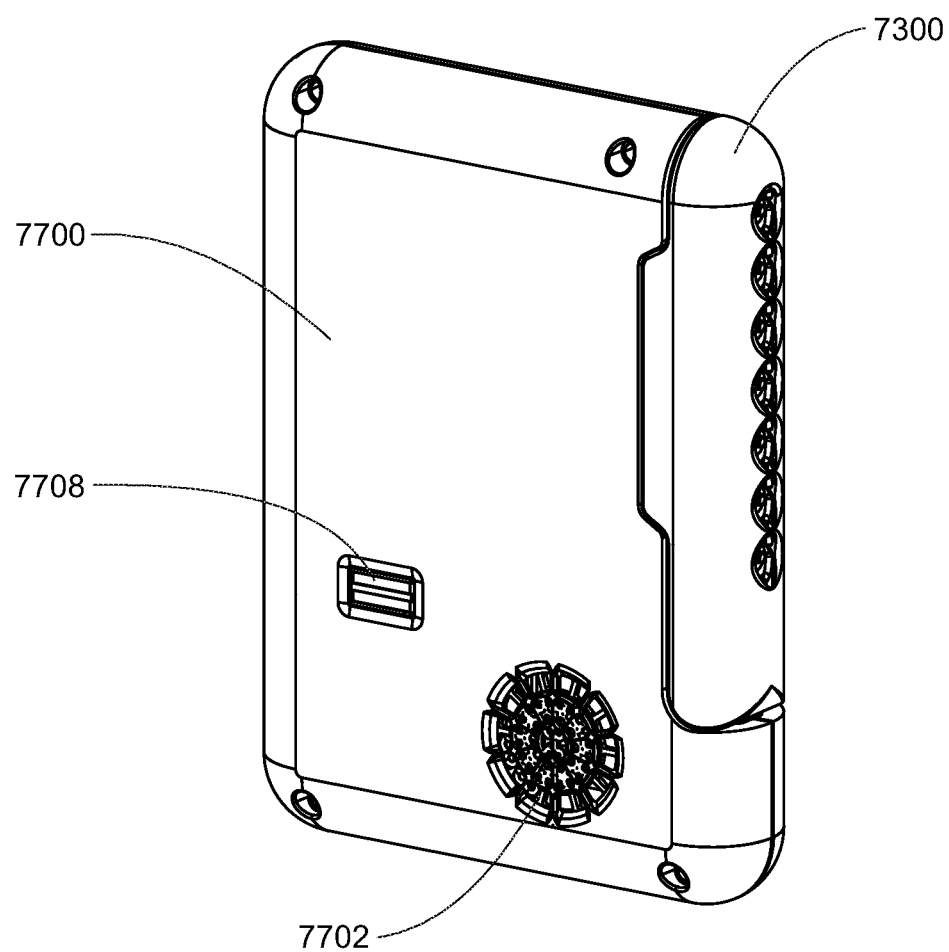
FIG. 77C shows a back view of one embodiment of a control unit housing and detachable manifold.
Figure 77D:
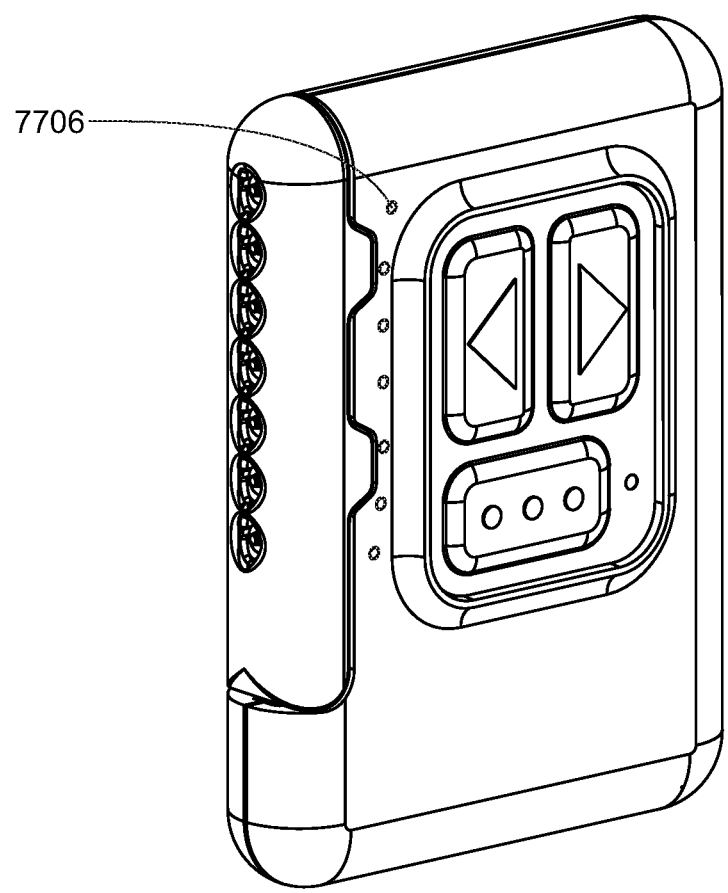
FIG. 77D shows a front view of an embodiments of a control unit housing and detachable manifold.
Figure 77G:
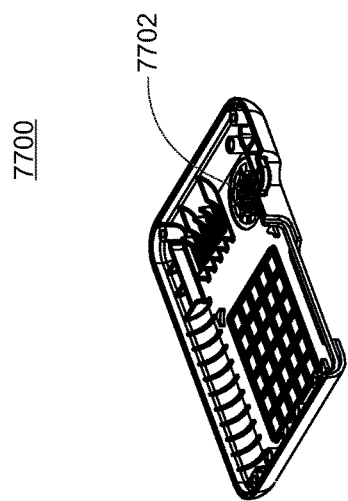
FIGS. 77E-77H shows various views of one embodiment of a lower housing of the control unit housing.
Figure 77H:
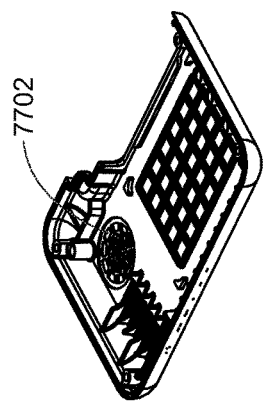
Figure 77E:
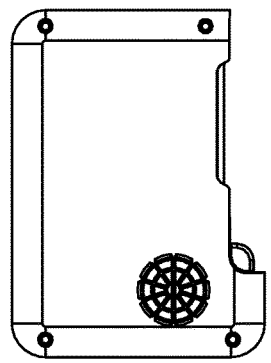
Figure 77F:
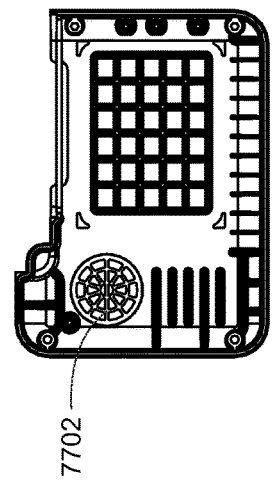
Figure 79A:
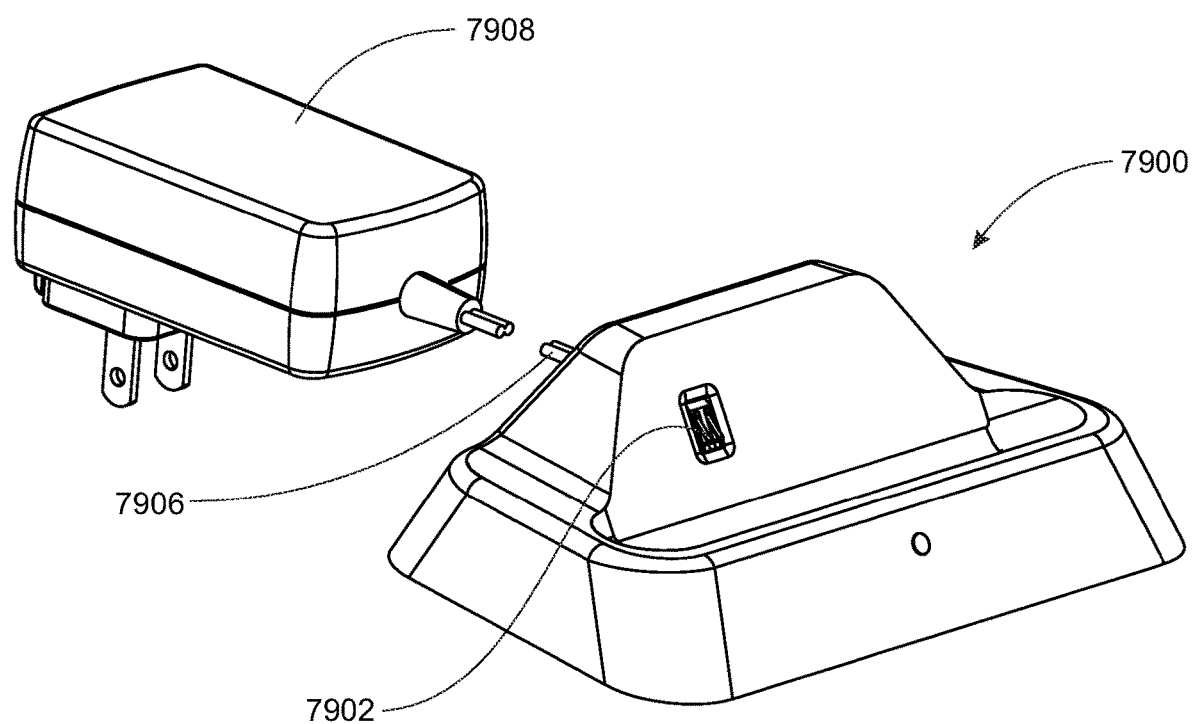
FIG. 79A is an isometric view of a recharging base station according to one embodiment.
Figure 79B:
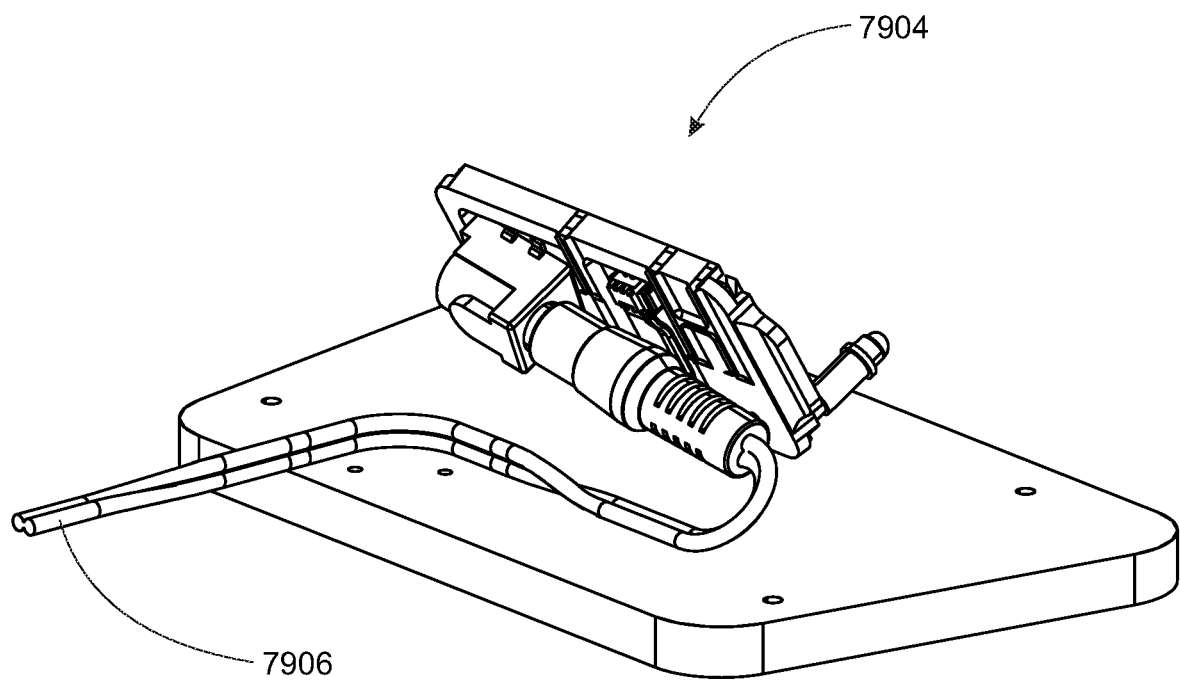
FIG. 79B is a view of the inside of one embodiment of the recharging base station.

Referring now also to FIGS. 79A-79B, in some embodiments, the control unit may be recharged using a recharging base station 7900, which, in some embodiments may be a charging cradle including a charging station interface 7902 to the control unit charging interface 7708 (shown in FIG. 77C). In some embodiments, the charging station interface 7902 includes contacts and spring pins which interact with the control unit charging interface 7708. In some embodiments, the charging cradle 7900 includes a reed switch 7904 connected to wires 7906. The control unit includes at least one magnet (not shown) in proximity to the control unit charging interface 7708 which activates the reed switch to complete a circuit/close the reed switch. Thus, the reed switch acts also as a proximity switch. Thus, the reed switch and the contacts in the charging station interface 7902 are inactive until and unless the control unit charging interface 7708 is in close proximity to the charging station interface 7902. In some embodiments, a metal-oxide-semiconductor field-effect transistor (MOSFET) may be used together with a reed switch.

In some embodiments the shape and/or size of the recharging base station 7900 may vary. In some embodiments, the recharging base station 7900 may include wires 7906 connects to a charging adapter 7908, which, in some embodiments, may be an AC adapter, which may plug into an outlet to receive a charge and communicate the charge to the recharging base station 7900.

Figure 82:
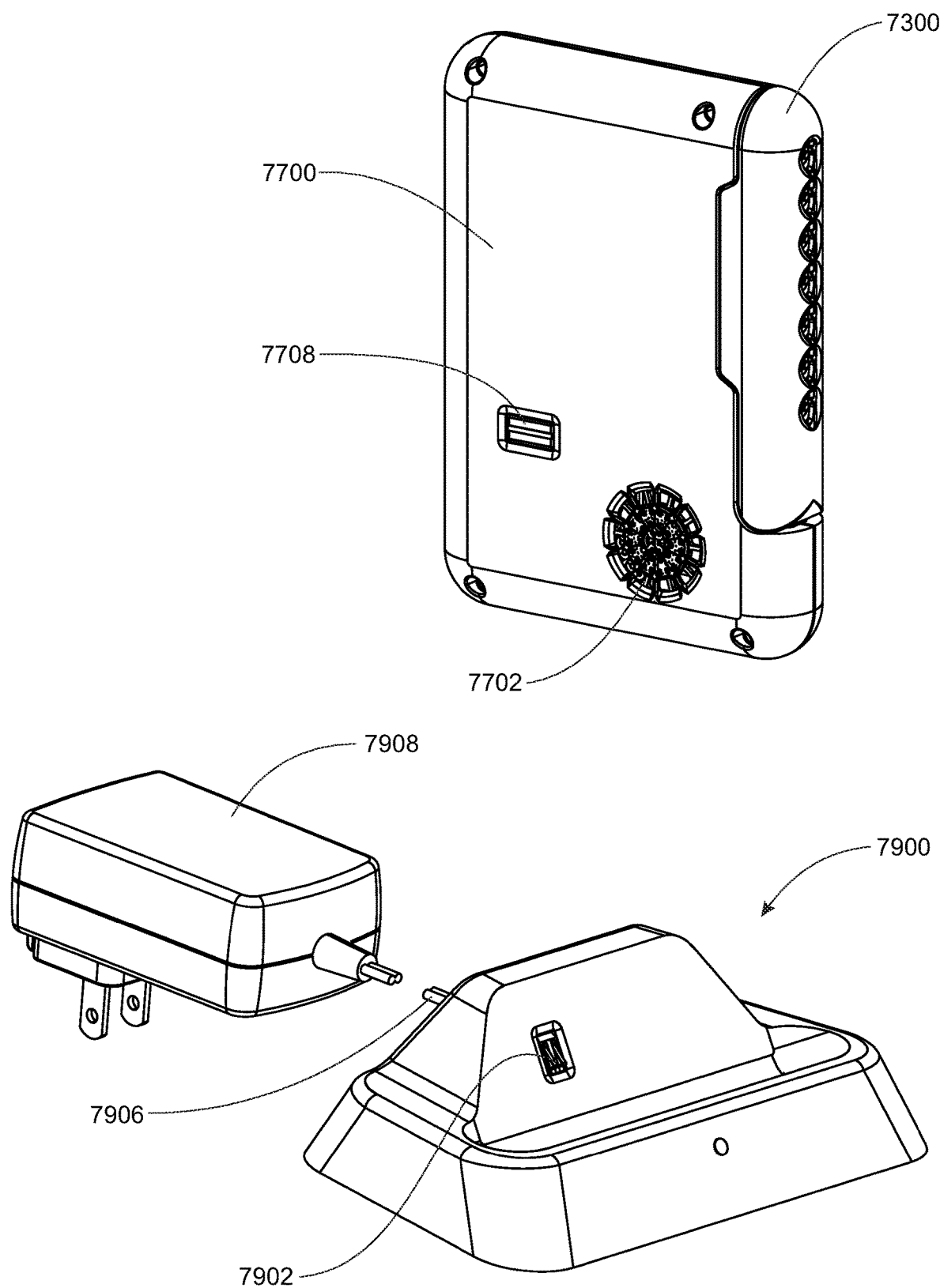
FIG. 82 shows one embodiment of a system for recharging a control unit.

Referring now also to FIG. 82, a system for recharging a control unit is shown. In this embodiment, the system includes a recharging base station 7900, a charging adapter 7908 and a control unit 7700. The recharging base station 7900 is configured to receive the control unit 7700.

The dynamic support apparatus is advantageous for many reasons, including, but not limited to, because it is able to compensate for shape changes of the residuum and/or loading from a prosthetic device by actuating the actuators. Additionally, when the actuators actuate, compliant tissue surrounding the bone within the residuum is displaced, thereby minimizing the amount of soft compliant tissue between the dynamic support apparatus and the bone within the residuum. This advantageously provides for a more stable and responsive interface between the dynamic support apparatus and the residuum. The dynamic support apparatus is also advantageous because various actuators may be actuated and unactuated at different times to improve blood flow within the residuum, without losing the overall stability of the dynamic support apparatus.

It should be understood that the various embodiments described herein are examples and that other embodiments are contemplated. Also, values given in the various examples serve as one example and the various systems and methods described herein are not limited to the values given. Further, in use, various methods and systems may vary based on the user.

The dynamic support apparatus is also able to advantageously detect the pressure and/or force provided by each actuator and to compensate for changes in the detected pressure and/or force. Thus, the dynamic support apparatus is able to self-compensate for pressure and/or force changes to provide increased securing forces and tighten the dynamic support apparatus only when necessary and to loosen the dynamic support apparatus when the prosthetic device is under lower load. This minimizes the perceived weight of the prosthetic device, which may allow the user to adorn the prosthetic device and dynamic support apparatus for a greater time than with a conventional prosthesis.

Although the dynamic support apparatus is illustrated for use with an upper-limb prosthesis, the support apparatus is adaptable to other body appliances such as ski boots, shoes, backpacks, helmets, lower-limb prostheses, braces worn around a body part, or anything designed to be worn around a body part.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. A system for providing support to a user, the system comprising:
   at least two groups of at least one bladder;
   a control unit comprising:
      at least one valve;
      a detachable manifold comprising at least one magnet, fluidly coupling the at least two groups of at least one bladder to the at least one valve;
      a pump connected to the at least one valve for causing actuation thereof;
      a user interface for receiving user inputs; and
      a control system for controlling the pump, wherein the control system has a first mode having a predetermined first pressure for each of said groups, and a second mode having predetermined second pressure for each of said groups, wherein at least one group has pressures different in the first mode and in the second mode and the control system controls the pump to actuate the at least one valve at least in response to a signal indicating the first mode or the second mode received by the control system from the user interface.

2. The system of claim 1, wherein the detachable manifold fluidly couples a plurality of bladders to the pump through a plurality of interior channels.

3. The system of claim 2, further comprising the valve in fluid communication with each interior channel for controlling flow therethrough.

4. The system of claim 3, wherein the control system controls activation of the valve.

5. The system of claim 1, further comprising a sensor to sense the pressure of at least one bladder, wherein the control system commands the pump to increase the pressure of the at least one actuator if the pressure detected by a sensor drops below a current pressure setpoint by more than a prescribed deadband.

6. The system of claim 5, wherein the control system commands venting of the at least one bladder if the pressure detected by the sensor exceeds the current pressure setpoint by more than the prescribed deadband.

7. The system of claim 5, wherein the control system commands the pump at a fixed time interval.

8. The system of claim 1, further comprising a switch configured to toggle the pump actuation between a first group and a second group of at least one bladder.

9. The system of claim 1 further comprising a third mode wherein the third mode is a pressure different from the pressures of the first mode or second mode.

10. The system of claim 1 wherein the controller further includes a third mode whereby the controller inflates the groups from no pressure to a predetermined initial pressure.

* * * * *